(12) United States Patent
Shillingburg

(10) Patent No.: US 7,395,214 B2
(45) Date of Patent: Jul. 1, 2008

(54) APPARATUS, DEVICE AND METHOD FOR PRESCRIBING, ADMINISTERING AND MONITORING A TREATMENT REGIMEN FOR A PATIENT

(76) Inventor: Craig P Shillingburg, 1513 East St., Golden, CO (US) 80401

( * ) Notice: Subject to any disclaimer, the term of this patent is extended or adjusted under 35 U.S.C. 154(b) by 1086 days.

(21) Appl. No.: 10/142,310

(22) Filed: May 8, 2002

(65) Prior Publication Data

US 2002/0169635 A1    Nov. 14, 2002

Related U.S. Application Data

(60) Provisional application No. 60/290,271, filed on May 11, 2001.

(51) Int. Cl.
*G06Q 50/00*    (2006.01)
(52) U.S. Cl. .......................................................... 705/2
(58) Field of Classification Search .................. 705/2–3; 128/897–906
See application file for complete search history.

(56) References Cited

U.S. PATENT DOCUMENTS

| | | | |
|---|---|---|---|
| 4,504,153 A | | 3/1985 | Schollmeyer et al. ......... 368/10 |
| 4,695,954 A | * | 9/1987 | Rose et al. ..................... 221/15 |
| 4,725,997 A | | 2/1988 | Urquhart et al. .............. 368/10 |
| 4,766,542 A | * | 8/1988 | Pilarczyk ........................ 705/3 |
| 4,768,176 A | * | 8/1988 | Kehr et al. .................... 368/10 |
| 4,768,177 A | * | 8/1988 | Kehr et al. .................... 368/10 |
| 4,939,705 A | | 7/1990 | Hamilton et al. ............. 368/10 |
| 5,020,037 A | | 5/1991 | Raven .......................... 368/10 |
| 5,108,006 A | | 4/1992 | Tieke et al. .................. 221/152 |
| 5,390,238 A | * | 2/1995 | Kirk et al. .............. 379/106.02 |
| 5,408,443 A | * | 4/1995 | Weinberger .................. 368/10 |
| 5,495,961 A | | 3/1996 | Maestre .......................... 221/3 |
| 5,706,257 A | | 1/1998 | Rothman et al. ............. 368/10 |
| 5,751,661 A | | 5/1998 | Walters ........................ 368/10 |
| 5,805,051 A | | 9/1998 | Herrmann et al. ......... 340/309.4 |
| 5,822,544 A | * | 10/1998 | Chaco et al. ..................... 705/2 |
| 5,826,217 A | * | 10/1998 | Lerner ......................... 702/177 |

(Continued)

OTHER PUBLICATIONS http://www.naturalvoices.att.com/news/fact_sheet.html; "Text-to-Speech Fact Sheet", Feb. 6, 2002.

(Continued)

*Primary Examiner*—C Luke Gilligan
*Assistant Examiner*—Russell Shay Glass
(74) *Attorney, Agent, or Firm*—Dorsey & Whitney LLP

(57) ABSTRACT

A treatment Device is provided which enables a Doctor/Pharmacist to provide patient specific instructions in a textual format to a patient. The instructions are converted by a speech synthesizer provided in the Device into an audibly perceptible format. When configured as a hand-held unit, the Device may store a plurality of medications. Upon activation or automatically, instructions saved in the device are communicated to a patient/user via various audible, visual and/or tactile indicators. The instructions are provided to the device via a Platform which enables Doctors and Pharmacists input instructions into the Platform, which, via a Platform interface, are saved into a storage device provided in the Device. In an additional embodiment, a removable medication dispensing cartridge is provided which facilitates the controlled and automatic dispensing of a medication to a patient based upon a treatment schedule. Patient compliance information with a treatment schedule may be provided by the Device.

33 Claims, 63 Drawing Sheets

U.S. PATENT DOCUMENTS

| | | | | |
|---|---|---|---|---|
| 5,845,255 | A * | 12/1998 | Mayaud | 705/3 |
| 5,950,632 | A | 9/1999 | Reber et al. | |
| 5,954,641 | A * | 9/1999 | Kehr et al. | 600/300 |
| 6,112,502 | A * | 9/2000 | Frederick et al. | 53/411 |
| 6,305,377 | B1 * | 10/2001 | Portwood et al. | 128/897 |
| 6,334,778 | B1 * | 1/2002 | Brown | 434/258 |
| 6,356,873 | B1 | 3/2002 | Teagarden et al. | |
| 6,383,136 | B1 | 5/2002 | Jordan | |
| 6,421,650 | B1 | 7/2002 | Goetz et al. | |
| 6,564,121 | B1 * | 5/2003 | Wallace et al. | 700/231 |
| 6,832,200 | B2 * | 12/2004 | Greeven et al. | 705/3 |
| 2003/0036683 | A1 * | 2/2003 | Kehr et al. | 600/300 |

OTHER PUBLICATIONS http://www.naturalvoices.att.com/products/tts_data.html; "Text-to-Speech Engine Data Sheet"; Feb. 6, 2002.

http://www.naturalvoices.att.com/products/speech.html; "Product Brochure"; Feb. 6, 2002.

* cited by examiner

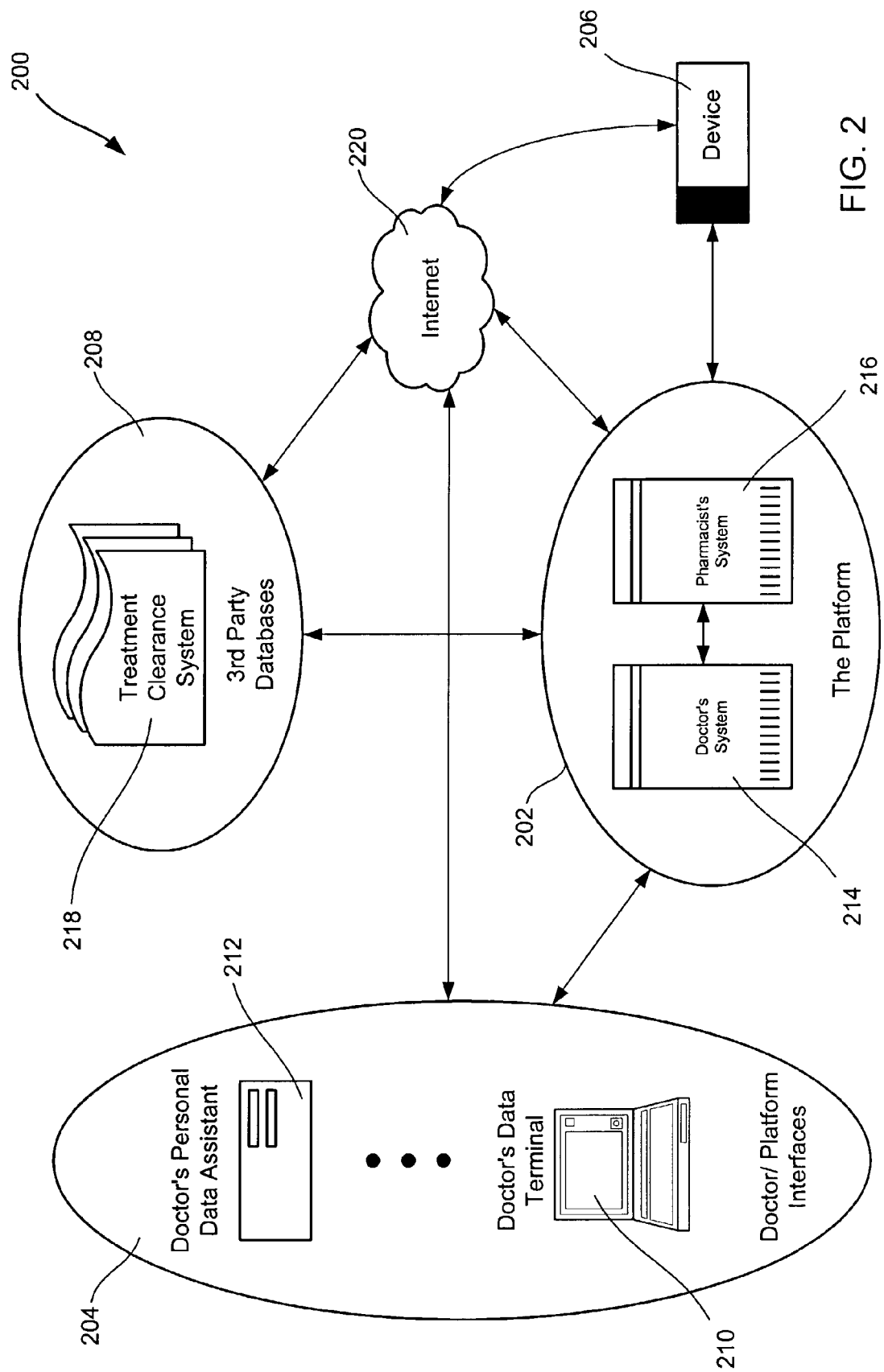

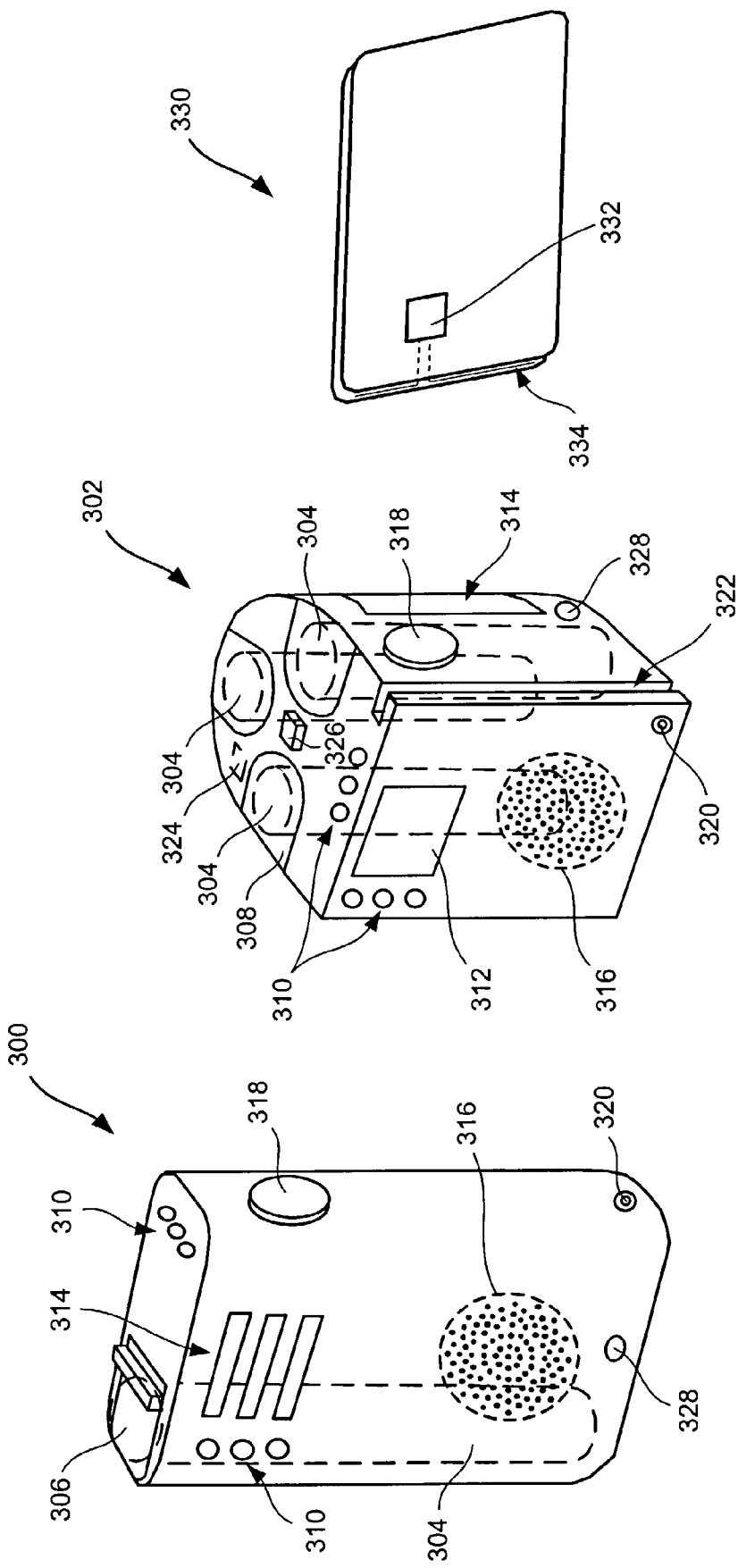

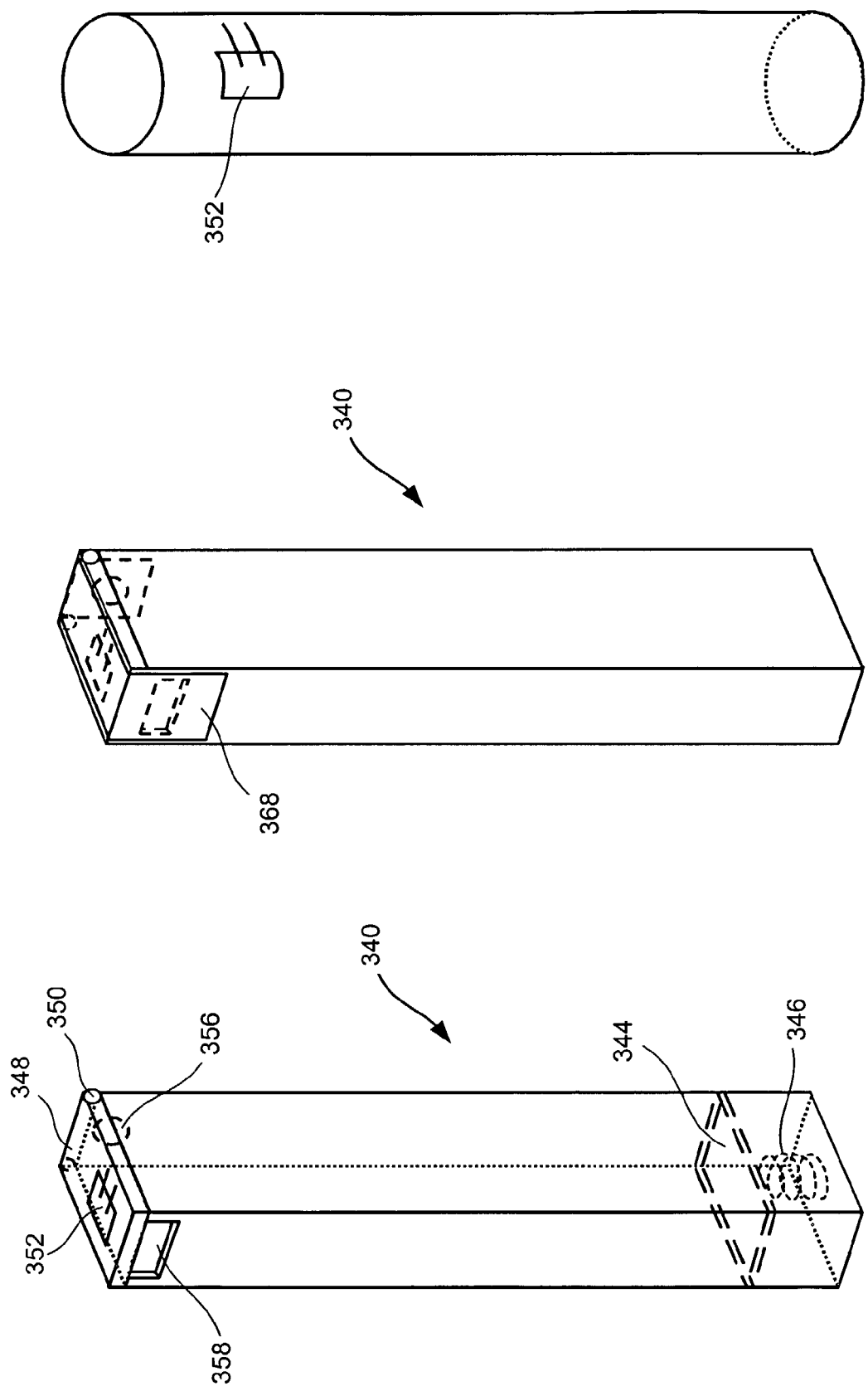

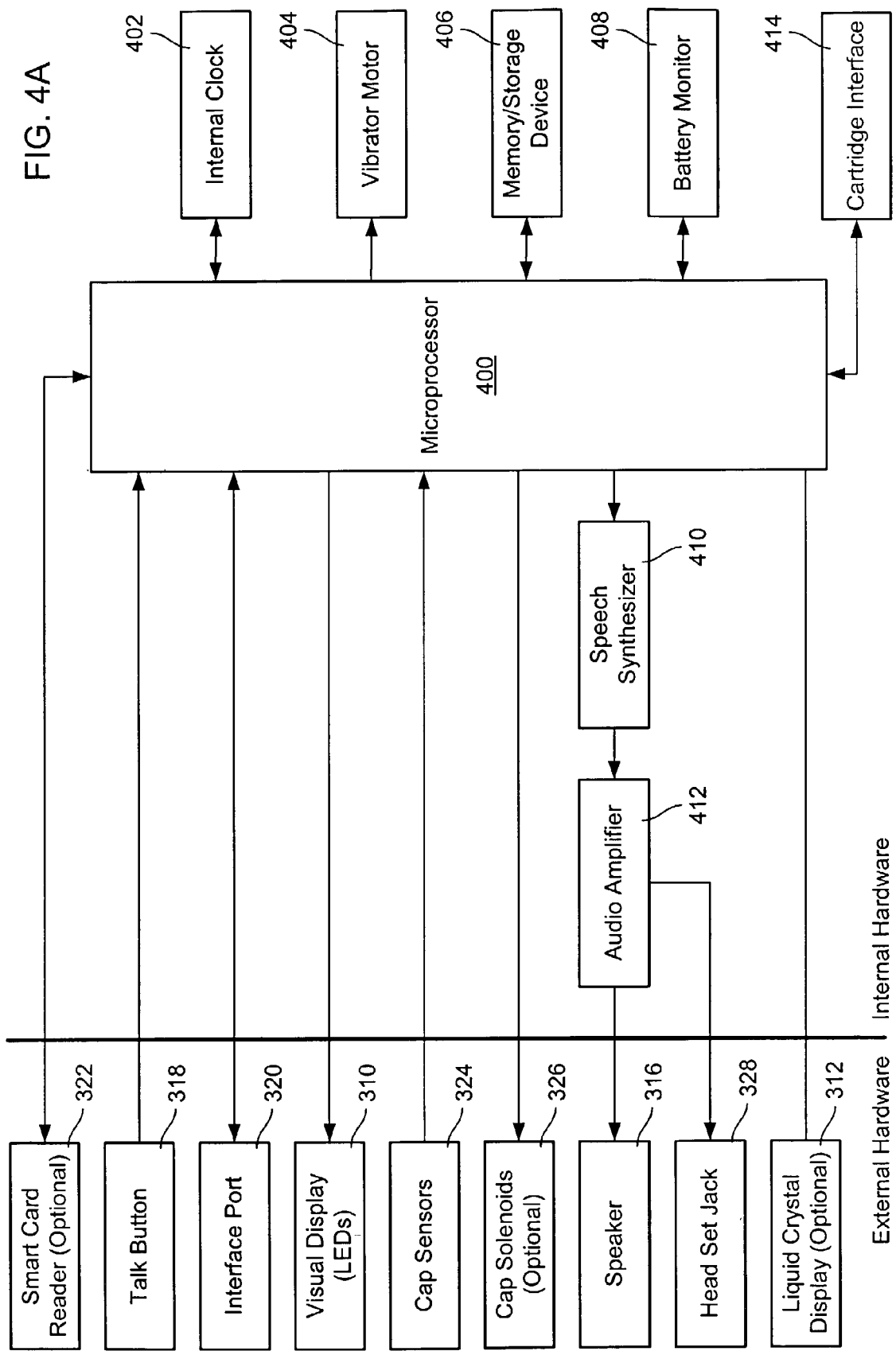

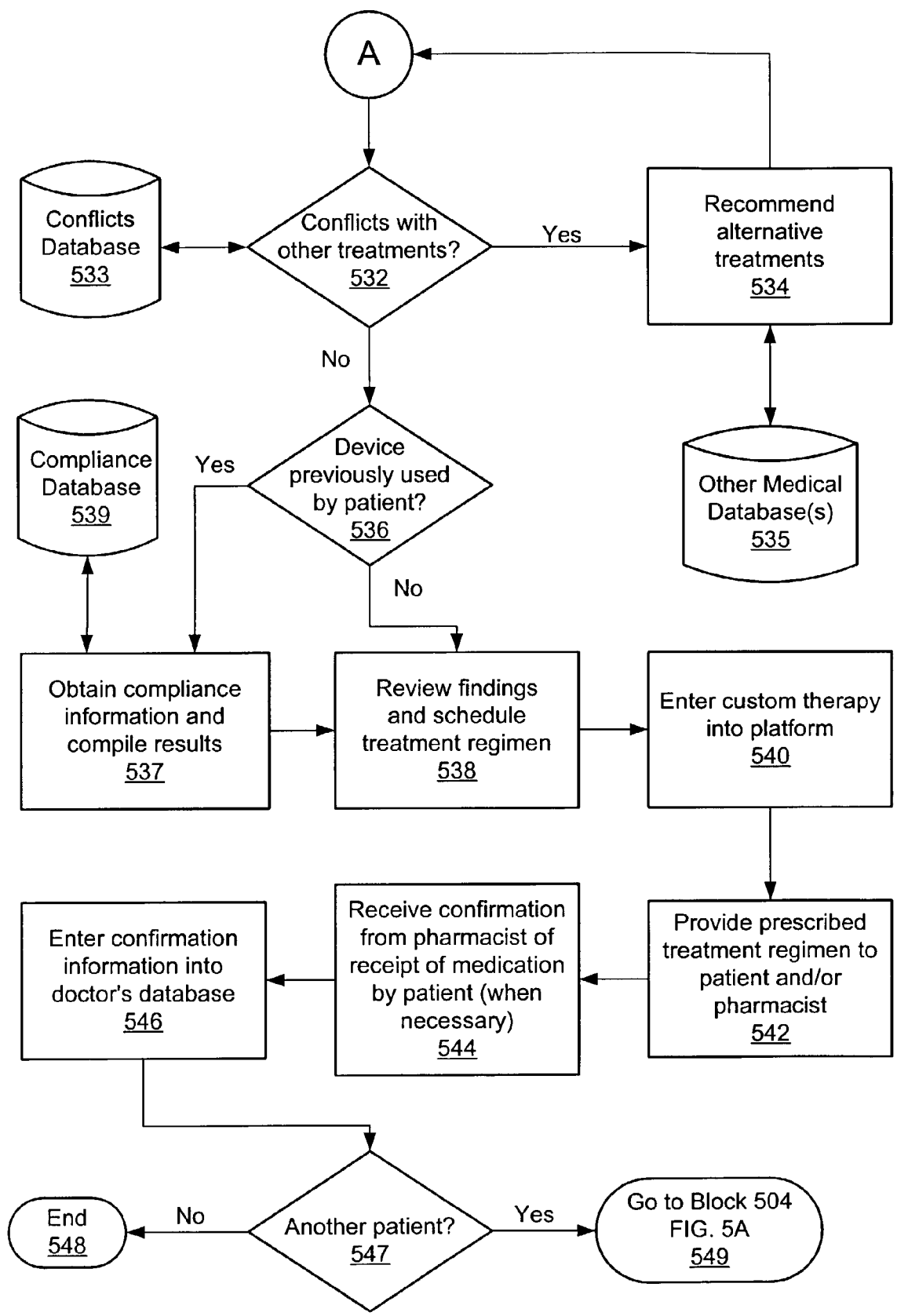
FIG. 5B1

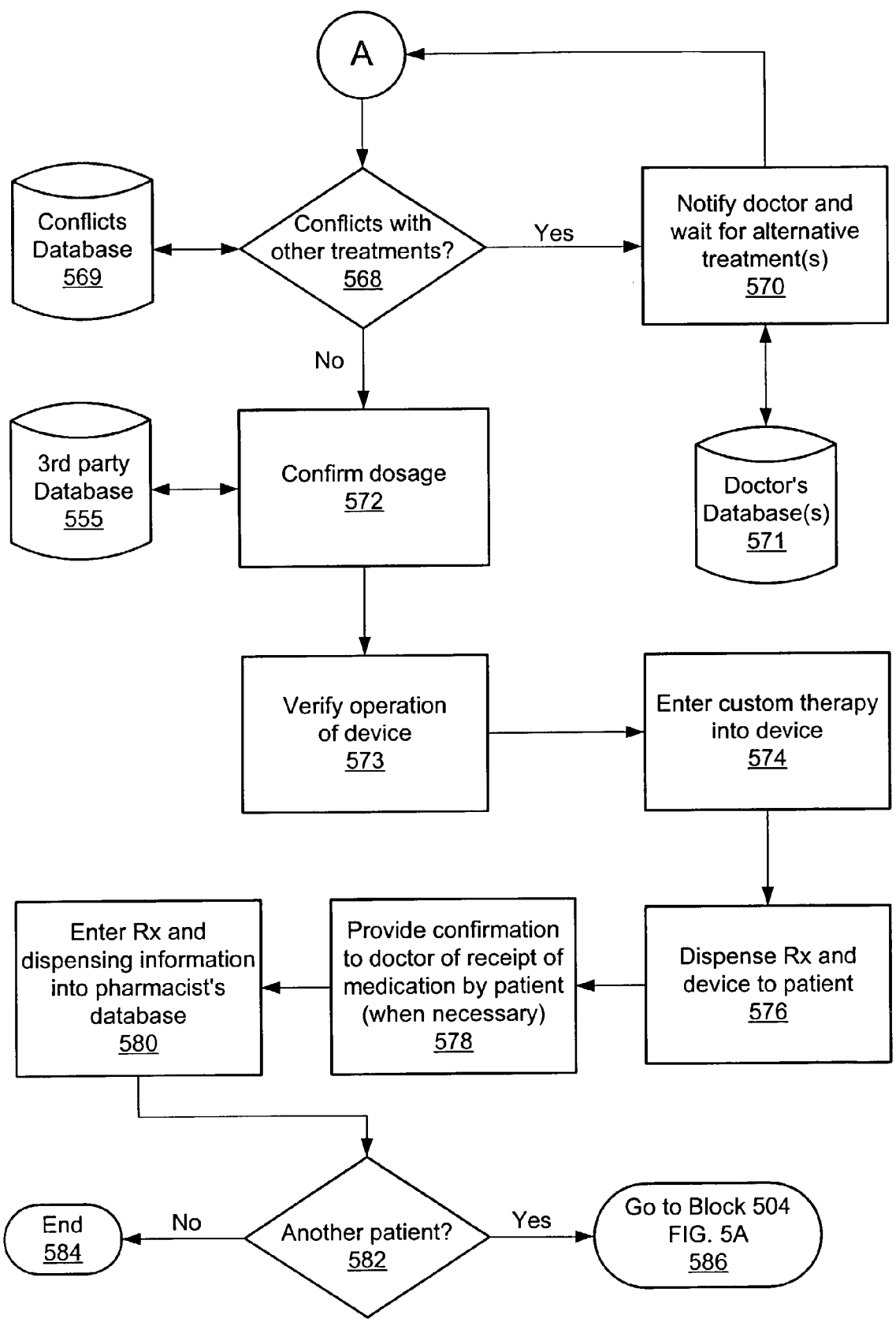
FIG. 5C1

FIG. 6B

Person Search

620

| Full Name | Patient # | Birth Date | Doctor |
|---|---|---|---|
| Amiscar, Bob | 5 | 9/1/1977 | Dr. Michael Smith |
| Craig, Jack | 8 | 10/12/1969 | Dr. Paul Plus |
| Garcia, Victor | 7 | 6/4/1978 | Dr. Tom Jones |
| Hamlin, Mark | 6 | 4/5/1972 | Dr. Susan Thomas |
| Riley, John | 9 | 1/3/1952 | Dr. Jack Geerhard |
| Sawyer, Diane | 3 | 7/21/1978 | Dr. Dick Simmons |
| Mickey, Joe | 2 | 10/19/1992 | Dr. Terry Downing |
| Jackson, Jay | 1 | 4/4/1977 | Dr. Ellen Caprianni |
| Zulu, Chang | 4 | 7/10/1959 | Dr. Michael Jordan |

Filtered: D    Total Cases: 9

Simple Find

A B C D E F G H I J K L M N O P Q R S T U V W X Y Z   All   — 624

Search Criteria

The search criteria you enter will determine what cases are shown.

| Search Field: | How to Search: | Search Criteria: |
|---|---|---|
| Last Name | Begins With | |
| First Name | Begins With | |
| Birth Date | Is Exactly | |
| Doctor Name | Begins With | |

Go to Selected Person — 626
New Patient — 614
Find Now — 630
Enter Search Criteria and Press [ENTER]
Close — 632

RxSure
File  Edit  Patient  Admin

Issue Date: 3/21/2000
Last Name: Rairigh
First Name - MI: Jay   L

[Find Patient] [New Patient]

Patient's Medical Record #:
From Doctor: DC3454
From Hospital: HPS34562A1
From Pharm: P23EF5412

[View Calendar]
[View Summary]
[Send Instructions]

Tabs: Patient Info | Care Providers | Medication | Rx Schedule | Notification | Case Management | Insurance | Notes

Patient's Primary Care Physician:
Physician Name:
Clinic (Optional):
Address:
City:
State - Zip
Phone:
Cell Phone:
Pager:
Emergency Phone:
E-mail:

Pharmacist:
Pharmacist Name:
Pharmacy:
Address:
City:
State - Zip
Phone:
Cell Phone:
Pager:
E-mail:

Hospital Admission Information:
Hospital Admitted To:
Admission Date:  mm/dd/yyyy
Hospital Phone:
Why Admitted:

Transfer to Another Doctor:
Clinic / Doctor Name:  [Search for Doctor]
Date of Transfer:  mm/dd/yyyy
Office Phone:

[Consent to Release]

Patient Consent

I hereby authorize my Primary Care Physician to disclose any such history, diagnostic and treatment information from my medical records (including information relating to the diagnosis, treatment or other therapy for the conditions of substance abuse, alcoholism or alcohol abuse, sickle cell anemia, or testing for or infection with human immunodeficiency virus) to the contractor of any health plan contract under which I am apparently eligible for medical care or payment of the expense of care or to any other party against whom liability is asserted. I understand that I may revoke this authorization at any time except to the extent that action has already been taken in reliance on it. Without my express revocation, this consent will automatically expire when all actions arising from the Primary Care Physician's claim for reimbursement for my medical care has been completed. I authorize payment of my medical benefits to the Primary Care Physician for any services for which payment is accepted.

Please Select:

Close Form

LOGO

Patient Information

Mr. Jason Smith
1222 Hoppy Drive
Snowflake, IL 60612
630-824-8866

Prescription Summary

Today's Date : 3/15/2002

Pharmacist

Physician Information

Dr. Harley Jacksobn
345 South Main
Snowflake, IL 60612
630-862-1221

Ms. Jackie Wren
134 N. Broadway
Snowflake, IL 60612
630-912-4397

Prescriptions

B6

| | |
|---|---|
| Dose Amount: | 150 mg |
| Pill Count: | 6 |
| Color: | Yellow |
| Form: | Two-tone Tablet |
| Refills Allowed: | 0 |
| Date Last Filled: | 1/23/2000 |
| Date of Next Refill: | 2/23/2000 |
| Meal Instructions: | Before Meal |
| Special Instructions: | |

Aspirin

| | |
|---|---|
| Dose Amount: | 150 mg |
| Pill Count: | 6 |
| Color: | White |
| Form: | Tablet |
| Refills Allowed: | 0 |
| Date Last Filled: | 1/23/2000 |
| Date of Next Refill | 2/23/2000 |
| Meal Instructions: | Before Meal |
| Special Instructions: | |

Tylenol

| | |
|---|---|
| Dose Amount: | 100 mg |
| Pill Count: | 6 |
| Color: | White |
| Form: | Tablet |
| Refills Allowed: | 0 |
| Date Last Filled: | 1/23/2000 |
| Date of Next Refill | 2/23/2000 |
| Meal Instructions: | Before Meal |
| Special Instructions: | |

Person's Name

A.M.

| A.M. | SUN | MON | TUE | WED | THR | FRI | SAT |
|---|---|---|---|---|---|---|---|
| 1:00 | | | | | | | |
| 2:00 | | | | | | | |
| 3:00 | | | | | | | |
| 4:00 | | | | | | | |
| 5:00 | | | | | | | |
| 6:00 | | | | | | | |
| 7:00 | B6 | | B6 | | B6 | | B6 |
| 8:00 | | Aspirin | | Aspirin | | Aspirin | |
| 9:00 | | | | | | | |
| 10:00 | | | | | | | |
| 11:00 | | | | | | | |
| Noon | | | | | | | |

P.M.

| A.M. | SUN | MON | TUE | WED | THR | FRI | SAT |
|---|---|---|---|---|---|---|---|
| 1:00 | | | | | | | |
| 2:00 | | | | | | | |
| 3:00 | | | | | | | |
| 4:00 | | | | | | | |
| 5:00 | | | | | | | |
| 6:00 | Tylenol | Tylenol | Tylenol | Tylenol | Tylenol | Tylenol | Tylenol |
| 7:00 | | | | | | | |
| 8:00 | | | | | | | |
| 9:00 | | | | | | | |
| 10:00 | | | | | | | |
| 11:00 | | | | | | | |
| Noon | | | | | | | |

| ASCII - Summary | | | | | | Rx Taken | | | | |
|---|---|---|---|---|---|---|---|---|---|---|
| | | | | | | | Segment | | | |
| Date | Time(Military) | I.D.No#. | Prescription | | TTL Count | 1-9 | 9-5 | 5-1 | Latency | Complications |
| 5/10/00 | 13:30 | 0213 | A | | 3 | 1 | 1 | 1 | 1 | 0 |
| 5/11/00 | 8:18 | 0213 | A | | 2 | 0 | 1 | 1 | 0 | 0 |
| 5/12/00 | 10:04 | 0213 | B | | 4 | 2 | 0 | 2 | 0 | 0 |
| 12/7/01 | 11:12 | 0213 | D | | 1 | 1 | 0 | 0 | 1 | 1 |
| 3/10/02 | 8:07 | 0213 | B | | 4 | 2 | 2 | 0 | 0 | 0 |
| 5/19/02 | 17:42 | 0213 | A | | 4 | 1 | 2 | 1 | 0 | 0 |

FIG. 60

ASCII - Functions (Openings & Instructions)

| | | Segment | | Message Requested | | | |
|---|---|---|---|---|---|---|---|
| Date | Time(Military) | Opened | Closed | Contents | Instructions | Contact | Function |
| 5/10/00 | 13:30 | 1 | 1 | 0 | 1 | 0 | 0 |
| 5/11/00 | 8:18 | 1 | 0 | 1 | 1 | 0 | 0 |
| 5/12/00 | 10:04 | 0 | 0 | 0 | 0 | 1 | 0 |
| 12/7/01 | 11:12 | 1 | 1 | 0 | 0 | 0 | 0 |
| 3/10/02 | 8:07 | 0 | 0 | 0 | 0 | 0 | 1 |
| 5/19/02 | 17:42 | 1 | 1 | 0 | 1 | 0 | 0 |

FIG. 6P

ASCII - Complication Notes

| | | Doc/Pharm | |
|---|---|---|---|
| Date | Time(Military) | I.D.No#. | Notes |
| 5/10/00 | 13:30 | 450574 | Patient had allergic reaction... |
| 5/11/00 | 8:18 | 000215 | Patient was drowsy... |
| 5/12/00 | 10:04 | 013288 | Patient did not take required amounts on schedule... |
| 5/15/00 | 11:12 | 450574 | Medication had no effect... |

FIG. 6Q

Threshold Rx Counts — 684

Patient
- Name:
- I.D. Number:

Prescription
- ☐ All
- Select:

Threshold Values
- Best Count — Expected Openings in 24 hours
- Best Count — Expected Openings in 1 week
- Best Count — Expected Openings in 30 days
- Serious ☐ Notify if 75% of Any Best Value
- Critical ☐ Notify if 50% of Any Best Value

| Export |
|---|

Save as ASCII file to: [C:\ID No#.ext (all, sum, bot, ins, cmp, etc.)]

Period Covered: From: [DD/MM/YY] To: [DD/MM/YY]

Separator: [(; , tab, space, etc.) ▶]

[Download]
[Cancel]
[Help]

Patient
Name: [____▶]
I.D. Number: [____▶]

Prescription
☐ All
Select: [____▶]

Content
☐ All
☐ Summary
☐ Complications
☐ Device Openings
☐ Message Instructions

Issue Date:

First Name - MI:

Last Name:

[Find Patient]  [New Patient]

Patient's Medical Record #

From Doctor:

From Hospital:

From Pharm:

[View Calendar]

[View Summary]

[Send Instructions]

Device Controls

1247

1249

Select Desired Default Settings
- ☐ Use Security Access Codes
- ☐ Perform System Checks
- ☐ Track Adherence
- ☐ Track Message Requests
- ☐ Check for Rx Conflicts
- ☐ Check for Rx Alerts
- ☐ Signal Low Battery
- ☐ Allow for Downloading
- ☐ Allow Message Exchange
- ☐ Print Rx Regimen

[Device Threshold Parameters]

Notifications:

Classification of Rx Use ▶
Sound Pitch ▶
Sound Volume ▶
Voice Gender ▶
Turn Off Reminders After: ▶

1248

— Device Alerts —

| Sensory-based Method | Use Signal | Linked to Deficiency | Desired Action |
|---|---|---|---|
| Vibrating Pulse | ☐ | ☐ | ▶ |
| Audio Signals | ☐ | ☐ | ▶ |
| Flashing Lights (LEDs) | ☐ | ☐ | ▶ |

Issue Date:

First Name - MI:

Last Name:

[ Find Patient ]  [ New Patient ]  ← 1273

Patient's Medical Record #

From Doctor:
From Hospital:
From Pharm:

[ View Calendar ]
[ View Summary ]
[ Send Instructions ]

↑ 1272

Linkage ← 1274

Dispenser Tracking:
- ☐ Opening and closing of slide
- ☐ Pressing of Notification Button
- ☐ Pressing of Confirmation Button
- ☐ Time Between Button Presses
- ☐ Time of Button Presses & Openings
- ☐ Repeated Message Request

Locking Features for Rx Access:
- ☐ The sliding opener remains unlocked during the entire scheduled medication time.
- ☐ The sliding opener will lock out after a valid opening, even if additional time is scheduled for Rx access.

Recorded History:

Check Desired Items for Permanent Record

- ☐ Notations
  - ○ Changes to Global Messages
  - ○ Changes to Specific Messages
  - ○ Medical Condition Notes
  - ○ Symptoms
  - ○ Reason for Discontinuing Rx Use
  - ○ Exchanged Messages
  - ○ Surveys
- ☐ Downloaded Information
  - ○ Adherence Statistics
  - ○ Message Statistics
  - ○ Threshold Statistics
  - ○ Database Access

- ☐ Initial Settings Upon Access
- ☐ Final Settings Upon Closure
- ☐ Consent Information
- ☐ Consent Distribution
- ☐ Rx Added
- ☐ Rx Removed
- ☐ Patient Removed
- ☐ Patient Transferred
- ☐ Schedule Changes
- ☐ Dosing Changes
- ☐ Status Changes
- ☐ Change in Access Codes
- ☐ Default Settings

Issue Date:
First Name - MI:
Last Name:

Find Patient    New Patient

Patient's Medical Record #
From Doctor:
From Hospital:
From Pharm:

View Calendar
View Summary
Send Instructions

Archive

Notations:

Date/Time:

Search Specific Date    On: mm/dd/yyyy
Search Date Range      From: mm/dd/yyyy   To: mm/dd/yyyy
Keyword or Phrase:

Search History

RxSure - Administration

| Drugs | Pharmacists | Doctors | Speech | General Messages | Rx Messages | Red Button Messages | Green Button Messages |
|---|---|---|---|---|---|---|---|
| General Message 1: | | | | | | Edit | Voice Record |
| General Message 2: | | | | | | Edit | Voice Record |
| General Message 3: | | | | | | Edit | Voice Record |
| General Message 4: | | | | | | Edit | Voice Record |
| General Message 5: | | | | | | Edit | Voice Record |
| General Message 6: | | | | | | Edit | Voice Record |
| General Message 7: | | | | | | Edit | Voice Record |
| General Message 8: | | | | | | Edit | Voice Record |
| General Message 9: | | | | | | Edit | Voice Record |
| General Message 10: | | | | | | Edit | Voice Record |
| General Message 11: | | | | | | Edit | Voice Record |
| General Message 12: | | | | | | Edit | Voice Record |
| General Message 13: | | | | | | Edit | Voice Record |
| General Message 14: | | | | | | Edit | Voice Record |
| General Message 15: | | | | | | Edit | Voice Record |
| General Message 16: | | | | | | Edit | Voice Record |
| General Message 17: | | | | | | Edit | Voice Record |
| General Message 18: | | | | | | Edit | Voice Record |
| General Message 19: | | | | | | Edit | Voice Record |
| General Message 20: | | | | | | Edit | Voice Record |
| General Message 21: | | | | | | Edit | Voice Record |

RxSure - Administration

| Drugs | Pharmacists | Doctors | Speech | General Messages | Rx Messages | Red Button Messages | Green Button Messages |

Red "Talk" Button

| Select | Press Method: | Message: |
|---|---|---|
| ● | Press Once and Release (Announce Regimen) | (Gen. Msg for #0 -8) medications are due at this time. Your first prescription is ___(Auto Get Name)___ . Please (Auto Get Rx Instructions) ___Auto Get Rx___ Your second prescription is ___(Auto Get Name)___ . Please ___Instructions___ > >> etc. For more information about each prescription due, press & hold the red button for 2 clicks. |
| ● | Press and Release Twice (Contact Information) | Your doctor's name is ___(Auto)___ and the phone number is ___(Auto)___. The doctor's office is located at ___(Auto)___ ___(Auto)___. Your pharmacist's name is ___(Auto)___. For customer service and the nearest location, please call ___(Auto)___. |
| ● | Press and Hold for 2 Seconds (User Instructions/Warnings) | (Gen. Msg for #0 -8) medications are being tracked by this device. The first prescription due at this time is(Auto Get Name) ___ . >>> etc. This drug is used for (Enter purpose and instructions) ___. Press the Green and Red buttons at the same time to cancel. |
| ● | Press and Hold for 4 Seconds (System Check) | System test, Version ___ (Use Gen. Msg to insert number) for the period dated from(Enter Date) (Enter Date) ___ to ___ . If this system is working properly, you will notice the following: the red, yellow and green lights will flash; the device will vibrate, and a beep will sound. Please contact your Pharmacist if problems occur. |

Medication Status
● Rx Due   ○ Rx Not Due

[ Voice Record ]   [ Edit ]   [ Clear ]   Message ● On  ○ Off  (Enter Date)

RxSure - Administration

| Drugs | Pharmacists | Doctors | Speech | General Messages | Rx Messages | Red Button Messages | Green Button Messages |

Green "Confirm" Button

Questions  ● On   ○ Off

Select   Question #:   Text

● 1
○ 2
○ 3
○ 4
○ 5
○ 6
○ 7
○ 8
○ 9
○ etc.

[Voice Record]  [Edit]  [Clear]

APPARATUS, DEVICE AND METHOD FOR PRESCRIBING, ADMINISTERING AND MONITORING A TREATMENT REGIMEN FOR A PATIENT

CROSS REFERENCE TO RELATED APPLICATIONS

The present application claims priority to U.S. Provisional Application Ser. No. 60/290,271 filed on May 11, 2001 by Craig Shillingburg and titled "Process and System for Prescribing, Administering, Administering and Monitoring a Treatment Regimen for a Patient", the contents of which are incorporated herein by reference in their entirety.

TECHNICAL FIELD

The technical field in which various embodiments of the present invention are described relates generally to the field of medical treatment compliance programs and more specifically to the field of systems and methodologies for determining and monitoring treatment regimens for patients. Additionally, the technical field includes systems and/or processes for monitoring the compliance of patients with treatment regimens, which may include prescribed medications.

BACKGROUND OF THE INVENTION

It is well documented in clinical studies that approximately 50% of the ambulatory patients in the United States have difficulty remembering how and when to take their medications or comply with various treatment regimens (for example, fasting, exercise and dietary constraints). Complex treatment regimens, chronic diseases, physical or mental impairments, discipline problems, lack of pain, busy schedules, and age all contribute to noncompliance with prescribed therapies in homes and offices. In group settings, such as long-term care facilities, hospitals and nursing homes, additional compliance problems are caused by dosage errors, accurate and timely distribution of medications, and adherence to the particular regimen instructions. These occur because shortages of qualified nurses or caregivers are faced with an ever larger group of patients and an increasing count of corresponding medications and treatment regimens. Further, with the aging of the baby boom and the shortage of caregivers, it is anticipated that efforts to monitor the compliance of patients with treatment regimens will become ever more problematic.

Additionally, it is commonly known and appreciated that many prescription drugs or health aids, such as vitamins and health supplements, have specific ingestion requirements to ensure their effectiveness or minimize unnecessary side effects. These include, but are not limited to, taking the medication before or after a meal, with or without liquids, not in conjunction with certain drugs or alcohol usage, if pregnant, before or after menopause, and whether dependent upon a status of injury or presence of a chronic disease. The need to communicate accurate instructions for each specific medication becomes even more important when the patient is required to take more than one medication, vitamin, supplement, meal, or treatment regimen multiple times each day with a varying schedule and changes in dosage, frequency, and other variables.

Also, patients are often provided instructions for treatment regimens by various medical professionals and caregivers. Such professionals and caregivers include, but are not limited to, doctors, nurses, medical technicians, physical therapists, and dieticians. Throughout this disclosure (for purposes of simplicity) such professionals and caregivers are commonly referred to as "Doctors". Those skilled in the art appreciate the various legal and regulatory limitations placed upon individual caregivers, and the use of the term "Doctors" is not to be construed as limiting the present invention to persons holding advanced degrees in medicine or any other level of certification or licensing. Similarly, those responsible for dispensing or providing controlled medications commonly are pharmacists. However, doctors and nurse practitioners often provide samples to patients which are not dispensed through a pharmacy. For purposes of simplicity, a person dispensing a medication to a patient which the patient may administer to themselves or have administered to them (for example, with the aid of a nurse or other assistant) shall herein be collectively referred to as a "Pharmacist".

Currently, two standard methods are often used by Doctors to instruct patients on treatment regimens and specifically on how to take medications properly. One of these methods utilizes written and/or verbal instructions which pertain to a specific treatment regimen and are communicated by the Doctor directly or indirectly to the patient. Such instructions are often communicated in person, at a Doctor's office, however, remote instructions (including those via telephone, video links, facsimile, e-mail and other communications links) are also utilized. As is well known in the art, patients often misconstrue the instructions communicated by a Doctor because the patient is in pain during the visit, gets confused by the technical explanations, have comprehension difficulties, can not remember the precise instructions, are unable to read the Doctor's handwriting, and/or for various other reasons. Further, many medication and treatment regimens are time and/or sequence specific and/or require non-medication treatment regimens to be performed in order for the medication to be effective. In such circumstances, medication and/or treatment regimens may not be readily available to the patient at the preferred treatment time(s). Additionally, those assisting a patient in taking medications (for example, a son or daughter of an elderly person) are often not present when the Doctor communicates the treatment instructions and thus may not be fully informed of the recommended treatment regimen.

Further complicating the prescribing, administering and monitoring of treatment regimens for a patient is the fact that Doctors and Pharmacists often utilize inefficient and ineffective communication methods. Many persons are familiar with the practically illegible scripts Doctors commonly utilize to prescribe medications. In fact, it is commonly appreciated that there is a need for effective communication links between Doctors, patients, attendees, Pharmacists and others associated with treating patients.

Further, provided that proper consent and authorization has been provided, Doctors, Pharmacists and others often need to safely and securely share pertinent and secure information about a patient. Doctors, Pharmacists and others often need to also exchange current medical research data on diseases, impairments, medications or therapies and other information. Under current practices, Doctors and Pharmacists often must rely on the patient to furnish accurate and complete information regarding their medications, health supplements, and compliance history. Patients have to often provide this information (often collected in the form of a checklist followed by oral questions) because the means for a common electronic transfer system are not in place. The reasons often cited for this lack of a common electronic transfer systems include the lack of a unified software platform, equipment compatibility, and costly subscriptions fees. Consequently, Doctors and Pharmacists often are not fully appraised of a patient's condition. Referred Doctors (e.g., an orthopedic specialist), who may not be approved by the patient's insurance carrier or practices outside a specified health maintenance or preferred provider organization, often will not receive a complete patient profile which is needed to make an informed diagnosis and prescribe an effective and safe (when possible) treatment regimen.

A similar need exists to link medical professionals with current research information on diseases, impairments, medications or therapies from independent companies at an affordable cost. Many Doctors and Pharmacists rely on medical journals, independent research, paid subscriptions and promotional materials supplied by manufacturer representatives to stay current with the ever-changing medical field. This is a timely and expensive process that can become overwhelming given the increasing patient load commonly being seen and cared for by today's Doctors.

Further, the number of medications taken by a patient can vary from none to several dozen or more depending on age, the type or stage of a particular disease, physical or mental impairments, and the occurrence of a new injury or accident. Each medication typically has its own specific regimen (which should be followed to avoid unnecessary complications and/or undesired side effects) and comes in a variety of sizes, shapes and unit counts. Consequently, the need exists for a base-operating platform that can be used, in one or more devices sized to accommodate the different dispensing needs, to assist in the administration of a given treatment regimen. Some individual patients may require a small, portable device or a table-top version for home use, whereas a long-term care facility may require a larger unit or a surface-mounted station to handle the needs of many patients.

It is also commonly appreciated in the medical community that medications can be extremely dangerous if taken improperly. Thus, a need exists for a device that is easy to use, is capable of providing instructions for the treatment regimen, and contains a series of redundant safety features that enables a patient, caregiver or third-party individual to administer the taking of the medication in pre-selected doses at pre-determined times without having to receive separate instructions from a Doctor or Pharmacist. From the medical professional's perspective, the interfacing software used to program the device is preferably easy to use and facilitates the efficient entry of data and instructions and the retrieval of compliance information. Further, such a device is desirably capable of being interactively programmed from a remote source.

Therefore, there is a need for a system and process which enables a Doctor to communicate patient information with other Doctors and/or Pharmacists. Such a system also desirably enables the attending Doctor to efficiently determine whether a treatment regimen may be contra-indicated for a specific patient based upon patient information, general medical information, medication interaction information, and other information. The system also desirably enables a Doctor or Pharmacist to monitor the patient's compliance with the prescribed treatment regimen.

As mentioned previously, two methods are often used to communicate a treatment regimen to a patient. A second method often utilizes prescription labels attached to a pill-box or medication container (a "Container") by a Pharmacist. Due to the limited space on a Container, these instructions are typically very brief or abbreviated. More complete instructions, including warnings, side effects and instructions for taking the medication, may be provided in the retail or wholesale packaging but are often printed in a very small font and discarded after the package is opened. Since patients often require the assistance of others to take their medications, the Container and associated packaging materials are often ineffective in properly and routinely notifying a patient or their caregiver about a treatment regimen. Further, such Containers commonly do not provide a reliable mechanism for monitoring compliance by the patient with a treatment regimen.

Currently, there are several electronic alarm devices available which are designed to help patients determine when medications should be taken. While such devices are generally effective at providing audible notification signals, such devices do not provide the before mentioned and desired features and functions and generally have many shortcomings. For example, such devices usually do not properly address the problem of instructing a patient on how to take their medications. Nor do such devices enable Doctors and/or Pharmacists to program the device with customized instructions and related warnings which are automatically converted into verbalized speech (when necessary) for communication to the client. As such, commonly available devices hinder the accommodation of changing medications and treatment regimens. These devices also do not provide a system and process which verifies whether a treatment regimen (which may include activities such as diet and exercise in addition to medications) is appropriate for a patient and do not monitor the compliance by the patient with such a regimen.

Another problem with current devices is the fact that third-party assistance is often necessary to open a prescription container or organize a patient's medications for a particular day, week or month, especially if a physical or mental impairment exists. This process can be costly, inaccurate and time-consuming depending on the competency of the patient's caregiver. Presently, Pharmacists do not directly fill medication organizers (i.e., containers for storing multiple medications taken by a patient on a regular basis) and, by law, are required to use only pre-approved containers with childproof caps, unless granted permission by the primary care physician for an easy-open cap. In nursing homes, long-term care facilities, and similar locations, only a registered nurse is allowed to sort the medications for dispensing to the patients.

Existing childproof caps for prescription, non-prescription and health supplement containers commonly function by either a press-turn motion or a press-squeeze-turn motion. These caps can be extremely difficult to open for the elderly and those with arthritis and coordination impairments. In moments of crisis, the problem is compounded by the tension and anxiety experienced by the patient. In addition, none of the caps supplied by the Pharmacist can monitor the opening or closing of the container to determine if the patient is in compliance with the prescribed treatment regimen. Therefore, a device is needed which allows patients to access medications with preferably little if any assistance while also allowing Doctors and/or Pharmacists to monitor compliance by the patient with a treatment regimen.

SUMMARY

One embodiment of the present invention provides a system and process which facilitates the provisioning of specific and individualized instructions to a patient (or care provider thereof) for a treatment regimen. Additionally, the system provides for the verification that the treatment regimen is safe and desirable for the patient, based upon the patient's medical history and other information, while providing Doctors and Pharmacists with patient compliance information which may be used to modify and design the patient's current and future treatment regimen. Further, in this embodiment, a software program and/or a hardware device may be jointly or separately utilized to prescribe, verify, dispense and/or monitor compliance by a patient with a treatment regimen which may include prescription medications.

More specifically, this embodiment of the present invention includes a software platform (hereafter, the "Platform") which may be accessed by the Doctors and Pharmacists to provide instructions on a treatment regiment to the patient. The Platform may be utilized with a system compatible hardware device (hereinafter, the "Device") which desirably contains input/output elements for communicating information to a patient and others (such input/output elements may include, for example, lights, speakers and communications ports) and associated software codes/programs which are used in controlling the various features and functions of the Device.

Further, in this embodiment, the Platform may be configured with an interface which enables the Doctors/Pharmacists to program the system-integrated Device with a customizable treatment regimen. The treatment regimen may include, for example, verbalized instructions for a wide variety of patients and medical conditions over an extended treatment period. The Platform also may include interfaces which enable Doctors and Pharmacists to communicate over secure communication links. Such communications may include confidential patient information that should only be shared amongst authorized users. Examples of communications links over which information may be communicated and exchanged between Doctors, Pharmacists and others include e-mail messages, facsimile, instant messages or other communications link which utilize secure network connections or secure information (e.g., encrypted information) over non-secure network connections. Further, such information may be entered and transmitted via the Platform utilizing a menu-driven format that accepts typed, touch screen, stylist (for example, on a Palm® or similar Personal Data Assistant (PDA)), spoken or other modes for entering and/or transmitting information. This embodiment may also utilize customized or standardized input screens by which Doctors and Pharmacists may input communications or other information. Such input screens desirably are easy to use and utilize creative time saving actions, links, input fields and the like.

In order to maintain, update, program and refine the operation of the Platform, other professionals besides Doctors and Pharmacists may be utilized. Such professionals include, but are not limited to, system programmers, software and/or hardware engineers, and medical-related and/or insurance-related administrators. Throughout this disclosure (for purposes of simplicity) such other professionals are commonly referred to as "Administrators". The designation as Administrator may further be defined based on security clearance to information stored on the Platform or in associated databases. Such security clearance is created using methods including, but not limited to, access codes, account numbers, and user passwords that allow certain, pre-defined, segments of the Platform to be reviewed or modified. A low level security clearance to stored information may refer to an Administrator such as an office assistant, technical aid, nurse or caregiver who is responsible to enter basic information about a given patient onto the Platform and may be allowed access to a limited number of screens or menus allowing a specific function to be accomplished. A high level security clearance, which may include Doctors and Pharmacists, may provide full access to the entire contents of the Platform including, but not limited to, the source programming code.

Additionally, the Platform, in this embodiment and in other embodiments, may be configured to access external research data from third-party medical information providers using commonly available communication links, such as the Internet. Via such communications links, Doctors and Pharmacists may receive automated program updates and access third-party medical databases, which may contain the latest and/or recommended treatment regimens for almost any and all ailments and conditions. Such information may be utilized by Doctors and Pharmacists in diagnosing and recommending a treatment regimen, which may include prescription medications.

Verbalized or typed data entries and menu keystrokes may also be used to interface with the Platform and/or program the Device. One embodiment of the Platform may convert spoken or typed inputs into serially formatted data that may be transmitted to a Device and/or stored in a location accessible by the Device. Additionally, at a plurality of predetermined times specified by the treatment regimen, the controller in the Device may utilize internal software code to convert the digitized instructions into audible speech for playback over a loudspeaker. Alternatively, in another embodiment, pre-recorded speech or other synthesized speech patterns may be presented by the Device. The speech is preferably presented in the order specified by a predetermined sequence, however, real-time determined speech patterns may also be presented. For example, for a given treatment regimen, a real time speech pattern (or other communication) may be presented to a patient. Such real-time speech patterns may be based upon current conditions, compliance history and/or other variables.

Further, for at least one embodiment, the Platform provides the capability of remotely programming the Device. When there is a need or desire to change prescription dosages, the timing of medication or treatment regimens or other configurations of a Device, Doctors and Pharmacists can update the controls and operation of the Device via a telephone, the Internet or other communications links. Additionally, the initial programming of the Device, for a specific patient, may also be accomplished via a remote communications link or a direct communications link.

For at least one embodiment, the Device may also be configured to generate sensory-based indicators which are designed to notify a patient when a treatment is needed, as specified by a given treatment regimen. The overlapping use, as desired, of visual, audio and tactile (e.g. vibration) alert mechanisms provide sensory output options which may be tailored to patients, especially patients who suffer from physical impairments or cognitive deficiencies and who need an adaptable reminder system. Additionally, the Device can be programmed to track each of a plurality of specific medications, the uniquely scheduled regimen for such medications, and the patient's compliance with such regimen. Further, the Device may be configured, as desired, to remind patients to perform certain other actions which may or may not be associated with a given treatment regimen and which may or may not involve the taking of a prescribed medication. For example, the Device may be configured to remind a patient to drink a glass of milk one hour before taking a required medication.

The Device may also be uniquely programmed by Doctors and Pharmacists such that those sensor indicators most effective for a particular patient are utilized (for example, a deaf person might receive a visual and a tactile indication, whereas a blind person might receive an audible and a tactile indication signal). The intensity, type and duration of such indication signals may also be suitably configured uniquely for each patient.

As such, various embodiments of the present invention fulfill the need for a system and process which monitors compliance by a patient with a prescribed treatment regimen. The systems and processes discussed herein combine an alert/ notification system with corresponding instructions on what actions need to be taken at a specific time. Verbalized instructions (or written instructions, for example, when utilized by the hearing impaired) are preferably included in various embodiments of the system because such instructions provide patients with complete information about accomplishing their treatment regimen and provide additional support in terms of time-sensitive reminders, reinforcement of the specific directions, patient encouragement, and related contact information.

These and other various embodiments of a process and system for prescribing, administering and monitoring a treatment regimen for a patient are further described herein with reference to the drawing figures, the detailed description and the claims.

BRIEF DESCRIPTION OF THE DRAWING FIGURES

FIG. 2 is a schematic diagram depicting the various hardware components utilized in a system embodiment of the present invention.

DETAILED DESCRIPTION

As mentioned previously, various embodiments of the present invention provide at least one process and/or system for diagnosing, prescribing and monitoring a patient's compliance with a treatment regimen. More specifically, in a first embodiment, a Doctor diagnosing a treatment regimen to a patient may utilize the systems and processes described herein to more accurately determine whether a diagnosis and contemplated treatment regimen is not contra-indicated for a specific patient based upon a medical history, prior or current medications taken, how the patient is presented, and/or other information and factors. Additionally, the Doctor may tailor the treatment regimen specifically to the patient by providing verbal or visual instructions via a Device to the patient regardless of the time, date, or location of the patient (provided the Device is accessible to the patient at such times). Similarly, various embodiments of the present invention enable Pharmacists to more accurately determine whether specific medications should be safe to administer to a specific patient while also enabling the Pharmacists to provide tailored instructions to such patients in lieu of, or in addition to, those instructions and/or information provided by a Doctor.

Figure 1A:
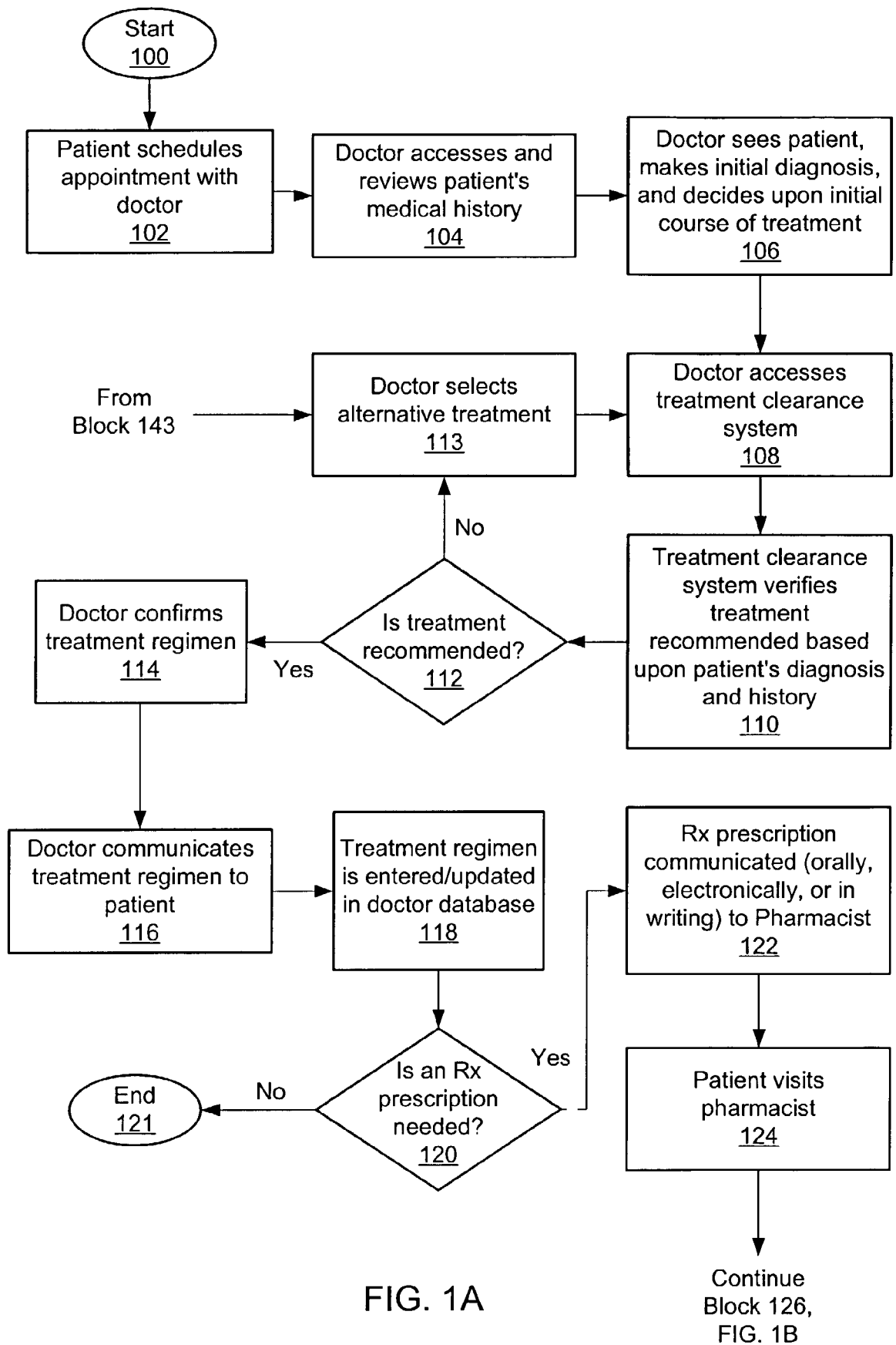
FIG. 1 is a flow chart depicting the overall process flow by which one system embodiment of the present invention is utilized by a Doctor, Pharmacist, and/or patient to prescribe and monitor a treatment regimen.
Figure 1B:
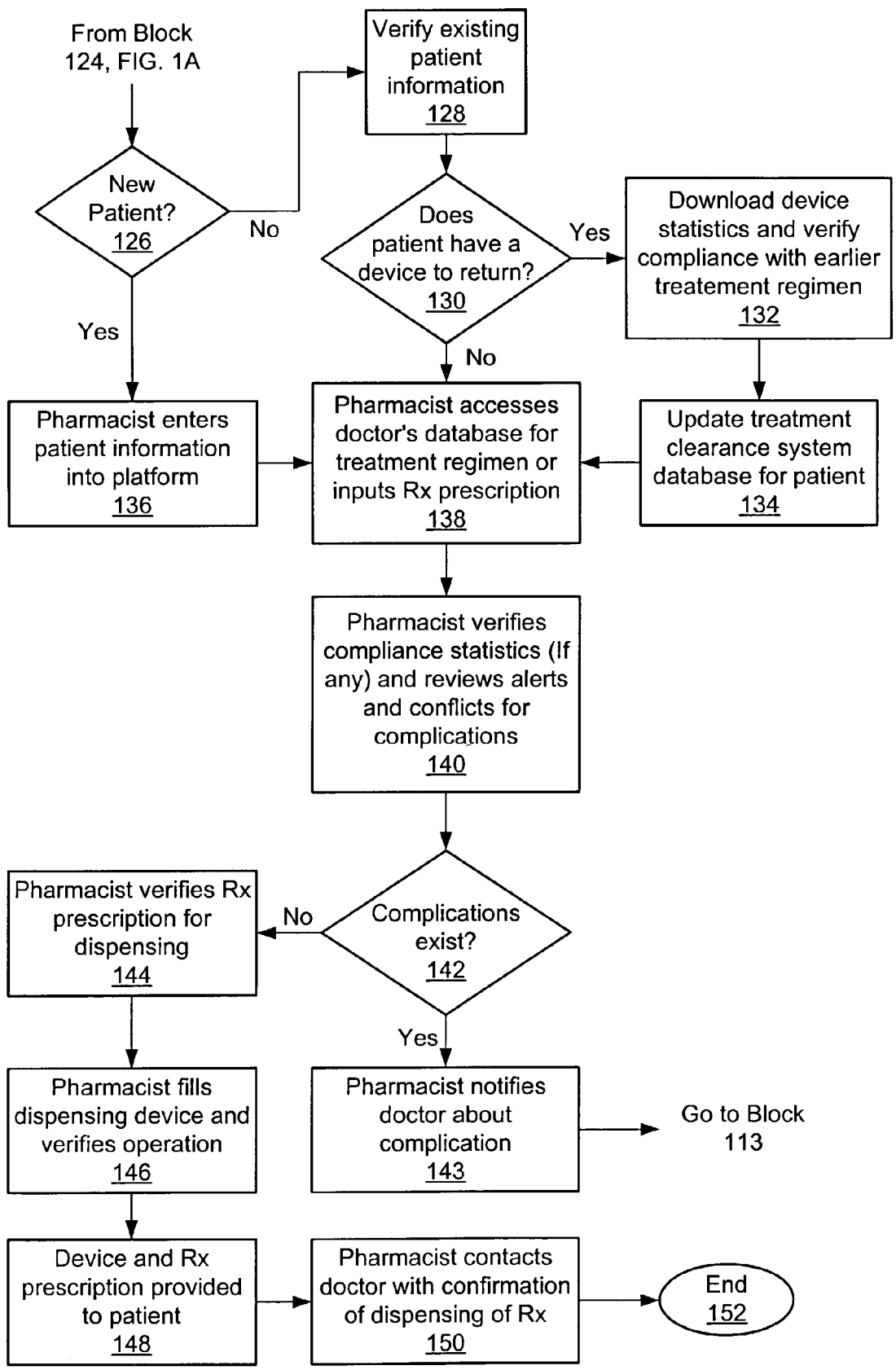

Referring now to FIGS. 1A and 1B, one embodiment of a process flow of the present invention is depicted. In this embodiment of the process flow, assistance is provided to the Doctor which enhances the Doctor's ability to quickly, efficiently, and/or accurately, diagnose a patient's condition, prescribe a course of treatment, assess any risks associated with a prescribed treatment regimen (i.e., is a specific medication safe for a patient, and if not safe what risks or side-effects are associated with the contemplated treatment regimen). The process flow also enables Doctors to generate instructions for the patient wherein the instructions may be generic, semi-generic and/or uniquely tailored to the patient and may be designed to assist the patient with complying with a treatment regimen. Such instructions may also specify how and when to monitor the patient's compliance with a given treatment regimen and/or provide other information to the patient, caregivers and others.

The role of Pharmacists, for one embodiment of the processes of the present invention, is also identified in the process flow of FIGS. 1A and 1B. However, it is to be appreciated that, in certain situations, a Pharmacist may not be involved in providing a treatment regimen to a patient. As such, FIGS. 1A and 1B encompass an omnibus view of the features and functions of one embodiment of the present invention. It is to be appreciated, however, that various embodiments of the present invention may be simplified into its individual elements or combinations of elements, as desired, without departing from the spirit or scope of the present invention.

As shown in FIGS. 1A and 1B, the present embodiment provides a process for diagnosing a medical condition, prescribing a treatment regimen (which may or may not include a prescription medication regimen), and monitoring the compliance by the patient with such treatment regimen preferably. The process generally begins when a patient schedules an appointment with a Doctor (Block 102). At an appropriate time thereafter, the Doctor then conducts a review of the patient's medical history and current condition, if any (Block 104). As is commonly known, the patient may or may not desire to share with the Doctor's assistants the purpose of the patient's visit. Additionally, for new patients, a medical history may not be available or accessible by the Doctor. As such, this embodiment of the process enables the Doctor to access and review the patient's medical history and current needs, when available, but does not require such a review to occur prior to the Doctor visiting with the patient.

Further, in certain situations (for example, a hospital emergency room), the scheduling of the appointment and the review of the patient's medical history may occur real-time. In such situations, the Doctor attending to the patient may access the patient's medical information. Such access desirably occurs regardless of where the patient's medical records are maintained and who is the patient's primary care physician.

Further, while patient's medical records are generally not kept in a data file that is accessible from a remote location, it is anticipated that such practices will become more common in the future. Additionally, while this embodiment of the present invention looks to the future for electronically accessible medical records, it does not depend thereon for its current or future application. As such, for this embodiment and other embodiments, it is envisioned that a process may be utilized by which Doctors are provided immediate access to patient's medical records, when authorized. Further, such access may be accomplished via shared network databases, as explained further hereinbelow.

Referring still to FIG. 1A, the process continues with the Doctor "seeing" the patient, making an initial diagnosis, and deciding upon an initial course of treatment (Block 106). It is commonly appreciated that a Doctor may "see" a patient in a multitude of ways including, but not limited to: in person, via a videoconference link (or similar remote links), through an assistant, via a series of laboratory reports (for example, a specialist who views recorded and/or real-time scans of the patient but does not actually see the patient), and in other manners. Thus, the process is not limited by any specific temporal, procedural, or other requirements by which a Doctor "sees" or attends to a patient. Similarly, the diagnosis of a patient's medical condition and/or the recommendation of a treatment regimen may occur after one or more laboratory tests, scans, patient visits, and other interactions by the patient with the Doctor or other caregivers. As such, the process may involve numerous repetitive instances of the Doctor "seeing" the patient (i.e., Block 106 may be repeated as necessary). Regardless of the type, number or frequency of visits, at some point the Doctor makes an initial diagnosis of the patient's condition (as it is presented by the patient at a relevant time) and decides upon an initial course of treatment (which may include, for example, prescribing a medication and/or recommending a treatment regimen).

A Doctor implementing this and other embodiments of the present invention may access a treatment clearance system. Access to the treatment clearance system may be via any communications connection. The Doctor may provide the patient's condition (i.e., how the patient "presents"), initial diagnosis, initial course of treatment and/or other information to the treatment clearance system (Block 108). Such information may also be provided by the Platform to a third party database via customized pages and menu options provided by the Platform, as explained in greater detail herein.

The treatment clearance system provides those features, functions and expert systems necessary to review a patient's medical history, current condition, and/or any other information provided by the Doctor. The treatment clearance system uses such information to confirm whether a treatment regimen is desirable for a given patient and/or to recommend an alternative treatment regimen. An example of a treatment clearance system which this embodiment utilizes, in whole or in part, is the UltiMedex® program provided by Micromedex®. The features, functions, capabilities, and interactivity of the UltiMedex® program are well known in the art and are not described further herein. This embodiment of the present invention may utilize any and/or all of such features provided by the UltiMedex® program, or other programs, as desired.

Further, various expert systems exists, which are designed to assist Doctors in diagnosing medical conditions, recommending courses of treatment for such conditions, recommending medications, and/or providing information on side-effects, dosages, contra-indicators, and other information related to prescription medications, over-the-counter medications, alternative treatments, herbal treatments, and various other forms of caring for a patient, may also be utilized, as desired. Using the present embodiment Doctors may utilize such programs alone or in conjunction with the UltiMedex® program. Also, Doctors may access other third party databases, applications or programs as necessary. Further, the various system embodiments are not limited to any specific system components or configurations for verifying: whether a particular treatment regimen is indicated or is contraindicated for a specific patient; determining dosages or treatment regimens; or performing other treatment related activities.

When utilized in a given embodiment and upon receiving the necessary information (as dictated by the specific clearance program utilized and the level of assistance requested by the Doctor), the treatment clearance system provides an indication of whether a treatment is contra-indicated or otherwise recommended for a patient, as identified to the system by the Platform and/or the Doctor (Blocks 110, 112 and 113). When the treatment regimen is contra-indicated or otherwise not desirable for the patient, the system suitably notifies the Doctor, who may make any necessary or desired changes to the treatment regimen. Depending upon the desired levels of interaction provided by the treatment clearance system, particular system embodiment capabilities and/or the Doctor's preferences, the clearance system may also be configured to recommend alternative treatment regimens. Such alternative treatments may be recommended automatically, in all instances, only when a treatment is contra-indicated and/or in other situations (for example, when a medication preferred by the Doctor is not covered by the patient's insurance provider, but a generic alternative is available). Further, a Doctor utilizing the Platform may also desire, in certain situations, to bypass the treatment clearance system and rely upon their own expertise and judgment. Various embodiments of the present invention readily support such desired and/or alternative practices.

At some point of the process, the Doctor desirably reaches a decision as to a recommended course of treatment for the patient. Such decision may be reached with or without the assistance of the treatment clearance system. The Doctor confirms the treatment regimen to the Platform (Block 114). At this instant, depending upon specific system embodiments and/or the level of interactivity desired and/or specified between the treating Doctor and other Doctors and/or Pharmacists, those Doctors and Pharmacists who have access to the patient's medical records (either in their entirety or in part) may obtain and/or be notified of the latest diagnosis and treatment regimen for the patient. Such information may be extremely useful in providing the proper care to a patient, for example, by denying refill requests for medications earlier prescribed to the patient.

Eventually, the Doctor communicates the treatment regimen to the patient (Block 116). The treatment regimen may include information and instructions to the patient which go beyond the basic administering of a prescription medication. For example, an athlete who has undergone knee surgery may be prescribed anti-inflammatory medications while also being placed on a strict physical therapy regimen. At least one embodiment of the present invention enables the Doctor to prescribe a treatment regimen to the patient in any of numerous methods, including verbally, in writing, on a PDA or similar device, or even the Device, as described further herein below. While the processes and systems discussed herein are primarily directed to the administering and monitoring of the compliance of a patient with a prescription medication treatment regimen, it is to be appreciated that the Device (or a comparable device) may be suitably configured to encompass instructions and information on a non-prescription treatment regimen, such as, one involving exercise, supplements, herbal remedies, and diet regimens.

Additionally, such treatment regimens may be updated in the Doctor's database for future reference by Doctors and/or Pharmacists as needed (Block 118). Thus, the systems and processes of the present invention provide the Doctors and Pharmacist with access to historical and/or currently prescribed treatment regimen(s) for a given patient (Block 120). If a prescription is not part of the treatment regimen, the process may end (Block 121).

When the treatment regimen includes a prescription for a medication (Block 120), the process generally continues with the Doctor communicating the prescription to a Pharmacist (Block 122). Any current or future methods for communicating a prescription to a Pharmacist may be utilized including, but not limited to, written scrips, telephone instructions, facsimile, e-mail, the Internet, and direct wireless connections (for example, a Doctor may enter a prescription into a PDA which suitably communicates the prescription to a Pharmacist over a wireless network). Preferably, the prescription communicated by the Doctor to the Pharmacist includes that information commonly provided in a written scrip including a designation of a type of medication, a dosage, and a frequency. Additionally, the prescription message may also include a message containing customized instructions for the patient. Such customized instructions may be provided to the patient, via the Device, at designated times and/or when desired, as discussed further hereinbelow.

When the patient receives a treatment regimen that includes a prescription for a medication, the patient may visit a Pharmacist to receive the medication and/or a Device (Block 124). Since U.S. Food and Drug Administration regulations currently require many prescription medications to be received in person by the patient or their representative, the process generally requires the patient/or their representative to actually travel to a pharmacy to receive the prescription medication. However, since foreign and/or U.S. laws and regulations often vary (or may vary in the future) on the dispensing of prescription medications and other controlled substances, the various embodiments of the present invention discussed herein are not to be construed as requiring the patient/representative to travel to a pharmacy to receive a prescribed medication. As such, any current or future method for providing medications to a patient may be utilized.

As shown in FIG. 1B, when the medication/treatment regimen is provided by a Pharmacist, upon the patient arriving at the pharmacy the Pharmacist may determine, preferably via a Pharmacist tailored version of the Platform, whether the patient is a new patient (Block 126). For a new patient, the Pharmacist may enter patient identifying information into the Platform (Block 136). The Platform utilizes such information to obtain a patient's medical records from an accessible database (Block 138) and/or to create a new patient record. In fully integrated systems (wherein the Doctors and Pharmacist utilize shared or commonly accessible databases) such patient information may include the mere entry of a patient identifier. In other applications, the patient information may include demographic information, medical information, and other information. Regardless of the precise implementation, it is to be appreciated that various methodologies exist by which a Pharmacist can receive patient information. Such information can generally be obtained either directly from the patient or others, or via telecommunications links with other systems and databases containing such patient information. For example, a database maintained by the patient's primary care provider or insurance company (which is accessible via the Internet) may be utilized, in one embodiment of the present invention, by an authorized Pharmacist upon entry of a unique patient identifier and a password. Thus, the various embodiments of the present invention may not be limited to any specific methodology for receiving patient information and/or to any specific level of detail regarding such patient information.

Similarly, when the patient is not a new patient for the Pharmacist, the patient's information may be verified by the Pharmacist using the Platform (Block 128). The Platform may also be configured to query the Pharmacist as to whether the patient has a Device to return (Block 130). This process step is generally performed whenever the patient is requesting a refill. However, this step may also be performed whenever the patient has a new prescription.

If the patient has a Device to return, the Pharmacist accepts the device and may download statistics stored and/or compiled by the Device (Block 132). These statistics may include compliance information for a given treatment regimen. The downloaded information may be utilized for various purposes, for example, updating a patient's file that is maintained in a database (Block 134). Such a file may be suitably used by the treatment clearance system, when desired, to determine conflicts, contra-indicators and other tasks. More specifically, the Device may be configured, as desired, to compile various statistics on the patient's compliance with a treatment regimen. In the first embodiment, such statistics are accessed when a refill or new prescription or treatment regimen is to be fulfilled. However, the compliance information may also be accessed at any time, provided the Device is equipped with a wireless or remote communications capability. Further, the first embodiment may utilize the device compliance information in order to provide indications as to whether a medication or treatment regiment may be contra-indicated for a patient. Recommended dosage levels and other information may also be provided.

Additionally, the compliance information may be used to generate statistical information for a single or a plurality of users. For example, during a clinical study on the effectiveness of an anti-migraine medication, the Device may be utilized to determine how often, how many, and at what times a patient taking the new medication is compelled to take another pill. Such information may be valuable, for example, in determining future dosing regimes, the effectiveness of the medication, and other information.

As mentioned previously, the Pharmacist may access the Doctor's database to obtain the prescribed treatment regimen and/or verify the written prescription's validity (Block 138). In the first embodiment, such verifications may be performed automatically, however, they may also be performed verbally, via fax with the Doctor's office, and in other manners. Further, when a Device is returned by the patient, the Pharmacist may also provide the previously downloaded patient compliance information to the Doctor's database while also reviewing the record for any warnings on prescriptions or other treatment regimens (Block 140). This feature is basically designed to prevent or discourage a patient from "shopping" for a Doctor that will prescribe a medication that is contra-indicated for the patient, but may also be used, for example, to reduce the occurrence of an emergency room or other Doctor prescribing a medication that is contra-indicated for the patient.

Further, the process may determine whether any complications exist (Block 142). The Pharmacist may also be provided with sufficient information about the new treatment regimen, contra-indicators (if any), and other variables to make a determination real-time as to whether it is safe and/or recommended to provide a medication to a patient. In unclear situations, a consultation with the prescribing Doctor and/or the patient's primary care physician may be necessary. Further, since the prescribing Doctor may not have been fully or accurately appraised by the patient about a current or past treatment regimen or medical condition, this process preferably provides a second check and enables the Pharmacist and/or the Doctor to verify the parameters for the new course of treatment. This process may also be configured to provide notifications and/or warnings to the Pharmacist about compliance problems, drug or treatment contra-indicators, and/or other patient specific information.

For example, utilizing at least one embodiment of the present invention, when a patient is diagnosed with a bacterial infection it is common course of treatment to prescribe a first anti-biotic. When the patient fails to take the first anti-biotic to completion and ends up visiting the Doctor with a worse infection, the Device enables the Doctor and/or the Pharmacist to verify that the patient actually opened the Device (and presumptively took a pill) in accordance with the prescribed treatment program. Further, when the desired level of compliance is not achieved, the Doctor and Pharmacist may be appraised of the fact that the patient had difficultly complying with the treatment regiment and did not take all of the medications per the designated schedule. Based upon this and/or other information, the Doctor may decide to prescribe a higher dosage, a shorter treatment cycle or perform other actions, such as creating a reminder message to the patient, which is delivered via the Device, about the importance of taking anti-biotics according to a prescribed treatment regimen. Thus, at this point of the process, the Pharmacist may be appraised of the new treatment regimen and, when a Device is returned, past compliance with previous treatment regimens.

Further, when a new treatment regimen or the patient's compliance with a previous treatment regimen are problematic, for whatever reasons (for example, adverse drug interactions or the patient's failure to complete a required first drug regimen before commencing on a second drug regimen), the Pharmacists and/or the Platform may be configured to notify the Doctor of the conflict and/or complications (Block 143). These notifications may occur automatically or upon the Pharmacist's direction, via any desired means of communication including, but not limited to, an electronic message over a shared system or database, an e-mail, a telephone call, and a page. The process then continues, for this embodiment, with the Doctor selecting an alternative treatment regimen, when so desired (Block 113).

When complications are not found, the Pharmacist may verify the prescribed treatment regimen is correct (Block 144) and may dispense the medication/treatment regimen to the patient. Such dispensing may include providing medications via the Device. More specifically, the Pharmacist may fill or insert medications into the dispensing Device. Verification that the Device will operate in accordance with the prescribed treatment regimen (Block 146) may also be accomplished. Further, since the Device, in certain embodiments, may be configured to receive and present customized audible instructions (and in certain embodiments with visual instructions) and/or automatically dispense medications (as provided for in an alternative embodiment discussed below), the Pharmacist also preferably verifies that the dispensing Device operates correctly before providing the Device to the patient (Block 148). The Pharmacist may also provide an update to the Doctor's database or the patient's information file that the patient has received the prescribed medication and/or treatment regimen information (Block 150). The process suitably ends (Block 152).

At this stage of the process, the patient has been provided with a Device for dispensing a medication. Various embodiments of the Device may provide, for example, upon the pushing of a button, information and/or instructions relating to a treatment regimen. Compliance with such instructions and treatment regimen may be monitored by the Device. Further, in certain wireless embodiments, verifications of Device operation and compliance information may be obtained via remote communications links.

As shown in FIG. 2, an embodiment of a system 200 for implementing the present invention includes the Platform 202, a Doctor/Platform interface 204, a patient Device 206, and a third party database 208. Each of these elements may be connected, for example, via the Internet 220, direct connections, or via any other communications link. Various types and configurations of communications link and/or systems may be utilized including, but not limited to, fiber optics, twisted pair wire, telephone circuits, Ethernets, intranet, wide area network connections, local area network connections, cable, satellite, and wireless connections.

Also, the data throughput may be provided at any data rates available. For the present embodiment, such communications links preferably utilize Digital Subscriber Links, T-1 links, or other high data throughput communications links, in order to minimize the amount of time necessary to communicate information between the Platform 202, the Doctor/Platform Interfaces 204, and the $3^{rd}$ party databases 208. Similarly, the client device 206 may be configured with a high speed data port, but as configured for the present embodiment, such data throughput capabilities are not needed nor the communications interfaces desired.

As mentioned previously, the Platform 202 may be further subdivided, as desired, into a Doctor's system 214 and a Pharmacist's system 216. Such systems 214 and 216 may be implemented on any suitable device including a network server, a computer workstation, a distributed system, a self-contained system, a personal computer, a micro-computer, a main frame computer, a PDA with wired or wireless communication capabilities, or any other similarly capable system or device. Further, while depicted in FIG. 2 as encompassing a single Platform containing both the Doctor's system 214 and the Pharmacists system 216, either system (Doctor's or Pharmacists) may be implemented independently of the other. However, in the preferred embodiment, a single Platform that is accessible by numerous Doctors and Pharmacists may be utilized, thereby minimizing data file sharing conflicts, communications delays and other constraints. Regardless of the specific implementation, the Platform is system and device indiscriminate and may be implemented, as desired and as particular needs dictate, on any device or system capable of performing the features and functions identified herein.

The Doctor/Platform interface 204, as shown, may also be provided on any of a variety of devices, provided such devices are capable of accessing the Platform and communicating the necessary information between the Doctor and the Platform. Various communication networks may be utilized to connect the Doctor with the Platform, the Device (via, for example, an Internet connection), and/or $3^{rd}$ party database(s) 208. One example of such an interface 204 is a lap top computer 210 (or desk top computer) utilized as a Doctor's data terminal. It is to be appreciated that a plurality of computers (lap top and/or desk top) may be suitably interconnected via wired and/or wireless networks. As such, a Doctor's office, hospital, or other facility may contain a sufficient number of readily accessible terminals (for example, one at each nursing station) via which the systems and processes of the present invention may be utilized. Similarly, a PDA 212 with a remote communications capability may be utilized to communicate information between the Doctor, the Platform, the Device, and/or the $3^{rd}$ party databases 208. In the preferred embodiment, wireless equipped PDA's 212 may be utilized by the Doctor to interface with the Platform 202. Further, the PDAs 212 may be voice activated and, thereby, enable the Doctor to communicate with the Platform 202 as if the Doctor is dictating or providing directions to a nurse or other assistant.

Similarly, the $3^{rd}$ party databases 208 may be suitably configured as system complexities and individual applications of various embodiments of the present invention dictate. As such, the $3^{rd}$ party database 208 may include a comprehensive treatment clearance system 218, such as the UltiMedex® system, and/or may include individual elements, which may perform specific tasks. Further, the $3^{rd}$ party databases 208 may include information provided by any source including, for example, the Food and Drug Administration, the American Medical Association, drug companies (e.g., Pfizer®, Merck®, and Glaxco-Wellcom®D), independent laboratories, chemical manufacturers, and any other treatment related information accessible over the Internet or any other communications link and provided in a format accessible by the Platform 202. Preferably, such information may be provided in an electronic format, however, other data formats may also be used, especially data formats used or supported by advanced computing systems and especially by artificial intelligence or expert systems.

Various embodiments of the Device 206 are further explained with reference to FIG. 3A, FIG. 3B, and FIG. 3D. As discussed previously, the Device 260 may be provided in a portable, pager sized, configuration such that a patient may easily transport the Device, for example, in a coat or pants pocket. However, larger versions of the Device 206 may also be utilized including devices capable of dispensing numerous medications and/or standalone devices utilized, for example, by a nurse to administer to a person on bed rest. Therefore, the Device 206 is not limited to any specific application, size, shape or configuration and may be utilized in various embodiments and configurations.

Referring now to FIG. 3A and FIG. 3B, two embodiments of the Device 300 and 302 are shown. For a first embodiment, a smaller, pager sized Device 300, as shown in FIG. 3A, may be utilized. It is anticipated that a Device 300 of such size and configuration is convenient to use and transport, while also being capable of storing a sufficient quantity of a given medication. While the embodiment shown in FIG. 3A is preferably configured to dispense a single medication. Another embodiment of the Device 302, which may be used and configured to dispense multiple medications, is shown in FIG. 3B.

Regardless of the size, shape, configuration or number of medications dispensed, the Device may include at least one internal chamber 304 for storing the medication. In the single medication dispensing embodiment, as shown in FIG. 3A, only a single chamber 304 is provided. In the multiple medication dispensing embodiment, as shown in FIG. 3B, three chambers 304 are provided. Further, it is to be appreciated that a chamber may be configured in any size and shape and is not limited to a vertical, tubular configuration, as shown in FIG. 3A and FIG. 3B. Additionally, any number of chambers may be provided in the Device with appropriate tradeoffs occurring in the size, shape and weight of the Device. Further, alternative embodiments of the Device may not include any chambers. Such a configuration may be utilized when non-medication based treatment regimens are prescribed or medications cannot be safely or effectively stored in the Device.

In general, the FDA currently allows medications to only be dispensed in approved pill containers which can not be recycled. To accommodate these and other regulations, the chamber 304 may be configured such that it accepts and suitably retains a disposable sleeve or other approved pill container (not shown) for storing the medications. In such an embodiment, the sleeve may be slid into the chamber 304 by the Pharmacist at the time of dispensing the medication and may be removed upon subsequent use or refilling of the Device. For medications which do not require a prescription (for example, aspirin), a generic and/or disposable sleeve may also be used as needed and/or desired. Additionally, in the multi-medication per chamber embodiment, the sleeves may be configured to hold multiple medications as needed.

Further, the Device may be configured with various opening caps which restrict and allow access to the medication in the chamber 304. As shown in FIG. 3A, one embodiment of a cap utilizes a sliding top opener 306 and may include an internal locking mechanism which prevents accidental spilling of the medication and/or non-timely access to the medication. Another embodiment is shown in FIG. 3B wherein a tab opener 308 is provided in the cap. Additionally, sensors 324 may be provided in order to determine when the cap (e.g., the sliding top opener 306 or the tab opener 308) is opened. These sensors may also be used to facilitate the collection of compliance information for a treatment regimen. Further, a solenoid locking mechanism 326 may be included in the Device in order to prevent non-timely and/or unauthorized access to the medications contained within a chamber 304. While the embodiments of FIG. 3A and/or FIG. 3B, include a sliding opener 306 and a tab opener, respectively, it is to be appreciated that various other caps/openers including, for example, a pop-top, a twist top, a child proof top or other caps/openers may be utilized in the Device. Further such caps may be equipped with cap sensors 324 and/or cap solenoids 326. Additionally, in the multiple sleeve per chamber embodiment, additional opening tabs (both internal and external) may be provided. Such tabs may also be configured to allow access to only specific medications at specific times, for example, as dictated by a treatment regimen.

The Device 300 may also include Light Emitting Diodes (LEDs) 310, which may provide visual indicators of the various operating states of the Device. While the embodiment shown in FIG. 3A includes LEDs 310, in alternative embodiment a Liquid Crystal Display (LCD) 312 (as shown in FIG. 3B) or similar displays may be utilized. Such similar displays may include incandescent, fluorescent, neon or other visual display devices. Further, certain embodiments of the Device may not include any visual display capabilities. The Device 300/302 may also include a slot 314 into which a Pharmacist may insert a name of the medication(s) and/or the prescription treatment regimen(s). In at least one alternative embodiment, such information may also be suitably presented to the patient via a label which may be adhesively attached to the Device.

The Device may also include a speaker 316 by which audible messages and indicator signals may be presented to the patient. Such messages and indicator signals may be presented in accordance with a treatment regimen programmed by the Doctor and/or the Pharmacist and/or based upon other variables (some of which may be set by the patient). While a speaker is preferably utilized, head-phones may also be utilized via a head-phone jack 328. As is discussed further below, such messages and status indicators may be retrieved by the patient at any time by selection of the appropriate buttons. Further, the Device 300/302 may also include a "Talk" button 318, which by using the appropriate selecting sequence (as described below), enables the patient to direct the Device to provide various status and treatment messages. For a first embodiment, a single Talk button 318 is provided. However, other embodiments may utilize other user input interfaces including, but not limited to, volume controls, alphanumeric keypads, voice command systems and/or additional buttons.

Further, the Device may also include a Platform interface. The Platform interface allows the Pharmacist and/or the Doctor to receive compliance information and/or program the Device via a docking station or other interface with the Platform. For one embodiment, a data port 320 functions as the Platform interface in order to facilitate bi-directional communications between the Platform and the Device. For other embodiments, other adaptors and/or ports may also be utilized as a Platform interface, such interfaces include, but are not limited to, a serial port, a parallel port, infrared, RF, IrDA, Blue Tooth, wireless, a Universal Serial Bus (USB) port, an Ethernet port, an RS-232 port, and a telephone data port. Thus, for various embodiments of the present invention, interconnectivity between the Device and the Platform may be provided via a wired or wireless communications system. Examples of wireless communications systems include, but are not limited to, paging systems, digital or PCS systems, cellular systems, infrared systems, and/or radio frequency systems.

Similarly, a smart card reader 322 (FIG. 3B) may also be utilized as an alternative Platform interface port. FIG. 3C provides on example of a smart card 330 which may be utilized in conjunction with various embodiments of the present invention to provide a portable and secure device for transporting prescription or other treatment information from a Doctor to a Pharmacist and/or another Doctor. As shown, the smart card 330 includes an embedded computer chip 332 which contains those desired processing and data storage capabilities. The computer chip 332 may be connected to a series of leads 334 by which the smart card 330 communicates with a reader. The card 330 may be made out of a lightweight, yet durable materials, such as plastic, and may be configured such that it is easy to transport and utilize, for example, by including a magnetic strip or stamp (not shown). The smart card 330 may be programmed by a smart card programmer or similar apparatus.

In another embodiment, the Device may also be configured with an automatic medication (pill) dispensing device. As shown in the cross-sectional view of FIG. 3D, this embodiment of the Device 336 includes locations for mounting a printed circuit card 338 which holds the processor and other components which control the features and functions of the present invention and are described in greater detail below and with reference to FIG. 4A and FIG. 4B. Additionally, this Device 336 may include at least one internal chamber 304 into which a medication dispensing cartridge 340 may be inserted.

Figure 3D:
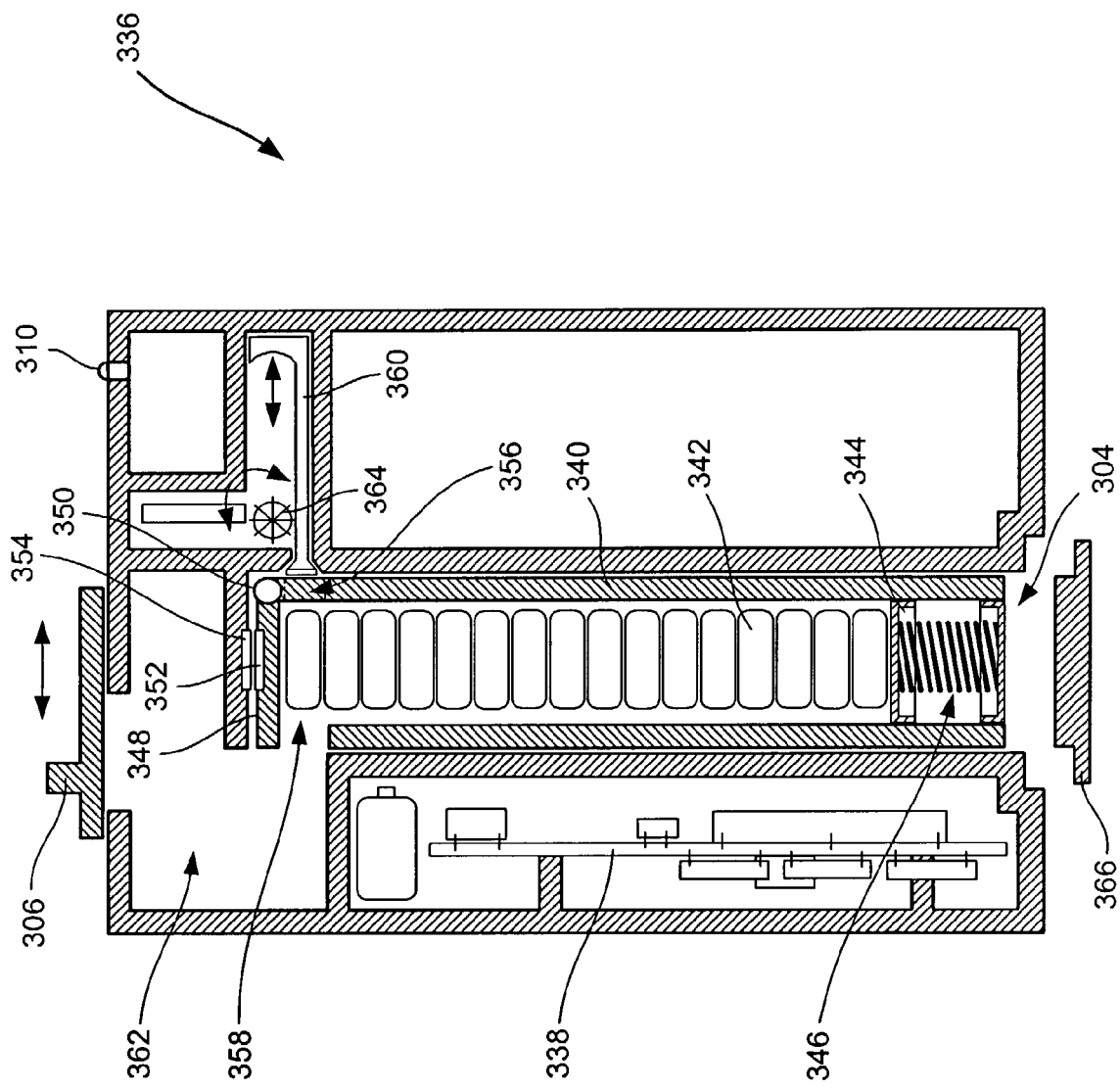
FIG. 3 is a pictorial illustration of two configurations of a Device which may be utilized in conjunction with various embodiments of the present invention.
Figure 4B:
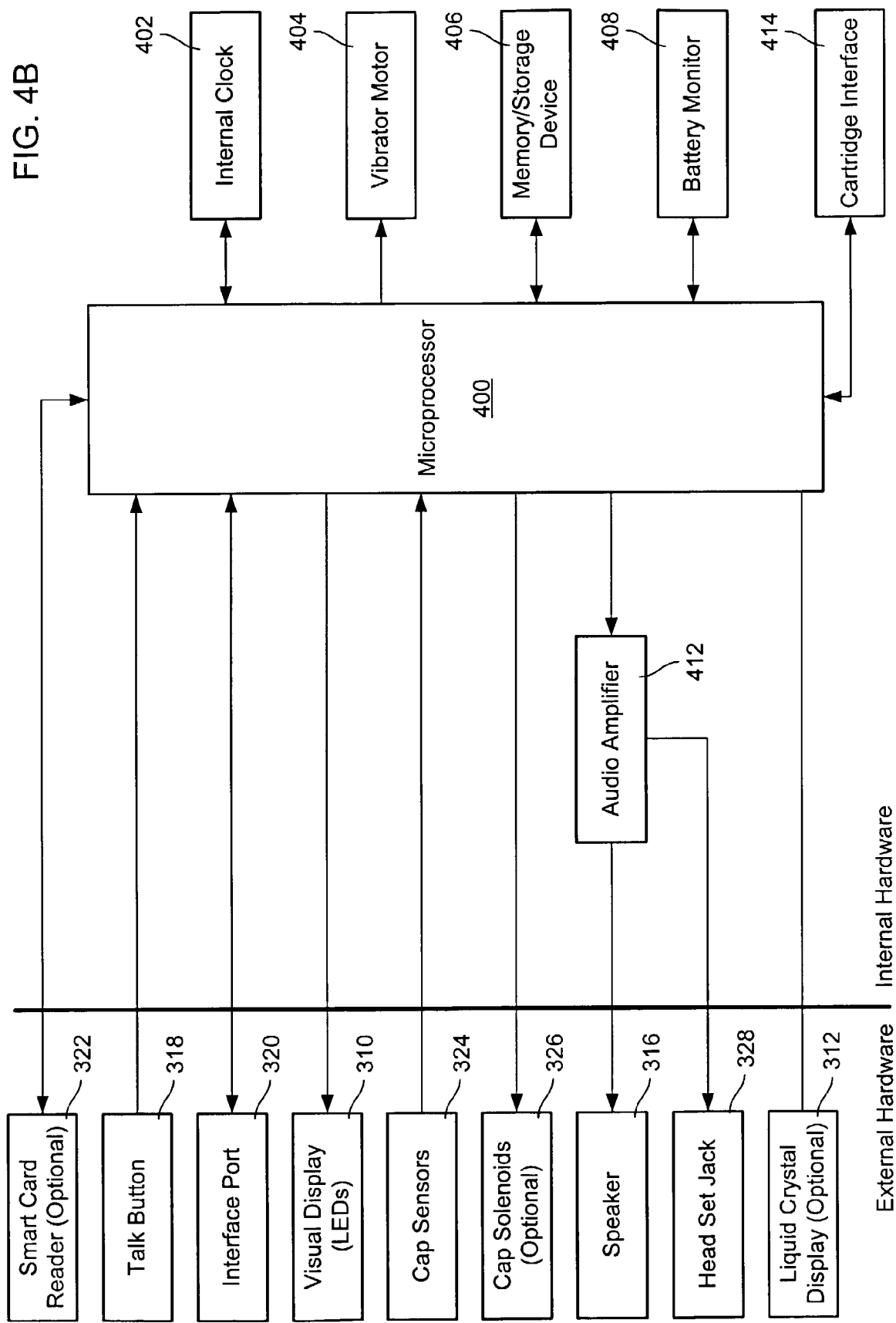
FIG. 4 is a schematic block diagram of the functional components utilized in one embodiment of a Device.

Various embodiments of a medication dispensing cartridge 340 are shown in FIGS. 3E, 3F, and 3G. With particular reference to FIG. 3D and 3E, the cartridge 340 may contain sufficient space to store multiple instances of a pill 342 (not shown in FIG. 3E). A platform 344 resting on a spring 346 is provided at one end of the cartridge 340 so as to provide an upward force upon any medications inserted into the cartridge 340. The cartridge 340 may also include a top lid 348 which may be attached to the sides of the cartridge 340, for example, via a hinge 350 or may be otherwise suitably connected. It is to be appreciated, however, that the top lid 348 and hinge 350 may be removed or repositioned on the cartridge as desired. For example, in the round embodiment of a cartridge, as shown in FIG. 3G, a top lid and hinge are not provided. Instead of a screw mount, pressure seal mount or other type of mount may be utilized to secure the cartridge after pills have been inserted.

Referring again to FIG. 3D and 3E, the cartridge 340 may also include an electrical connector 352. The electrical connector 352 may be positioned on the cartridge 340 such that an opposite connector 354 on the Device 336 may establish an electrical connection between the cartridge 340 and the Device 336. Information concerning the medication contained by the cartridge 340 is preferably communicated to the Device 336 via the electrical connectors 352 and 354.

A first opening 356 and a second opening 358 may also be positioned near the top of the cartridge 340 so that a medication transferring device, for example, a probe 360 or other member, may be inserted through the first opening 356 (thereby making contact with a pill 342) and the pill is pushed through the second opening 358 into the holding chamber 362. The probe 360, for one embodiment, is activated by a motor and gear 364. The motor and gear 364 may also be utilized to provide a tactile indication to a patient that a time for receiving a treatment has occurred. The cartridge 340 may be suitably secured into the Device 336, for example, by a screw top 366 situated at the bottom of the Device 336. As such, the operation of this alternative embodiment of a Device 336 may utilize a spring loaded cartridge 340 and a probe 360 to dispense a pill 342 from the cartridge 340 into a holding chamber 362 from which the pill 342 may then be consumed by the patient. The holding chamber 362 may be secured from the patient by a tab opener 306 or other opening. Similarly, the cartridge 342 may be secured into the Device 336 by a locking screw top 366 or other fastening means.

Additionally, the cartridge in certain embodiments 340 may be provided to the Pharmacist in a pre-loaded condition or an unloaded condition by a manufacturer of the medication to the Pharmacist. As shown in FIG. 3F, a safety seal 368 may be suitably attached to the cartridge 340 and removed by the Pharmacist prior to insertion into the device. Alternative embodiments of a cartridge and automatic dispensing mechanism may also be provided including a gravity fed cartridge (instead of spring fed cartridge) and various other forms of removing a pill from a cartridge.

Figure 3H:
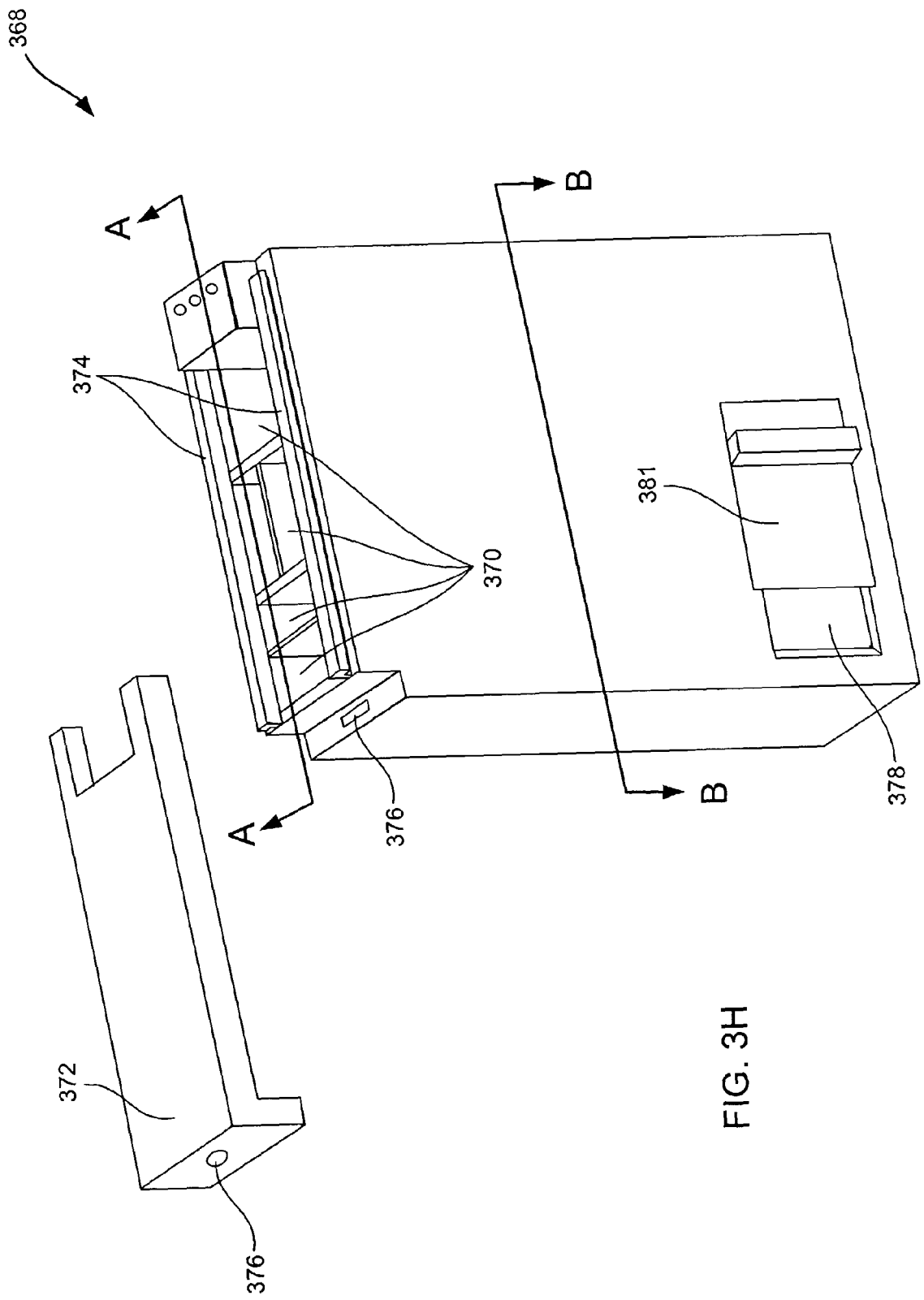

Another embodiment of the Device of the present invention is shown in FIGS. 3H-3K. As shown in FIG. 3H, this embodiment of a Device 368 provides multiple chambers 370 into which medications of various sizes and shapes may be inserted. Such medications may be suitably loaded into the Device 368 by a Pharmacist upon removal of a top lid 372 which may slide above, under and/or upon two rails 374 situated at the top of the Device 368. When sliding the top lid 372 on the rails 374, the top lid 372 may be secured into place via locking mechanism 376. The Device 368 may also include a lower holding chamber 378 which may be suitably accessed by a patient or other user, for example, via sliding side opener 381. The sliding side opener 381 may also include a locking mechanism (not shown) which may prevent or limit patient access to the patient accessible chamber 378 at improper times.

Figure 3J:
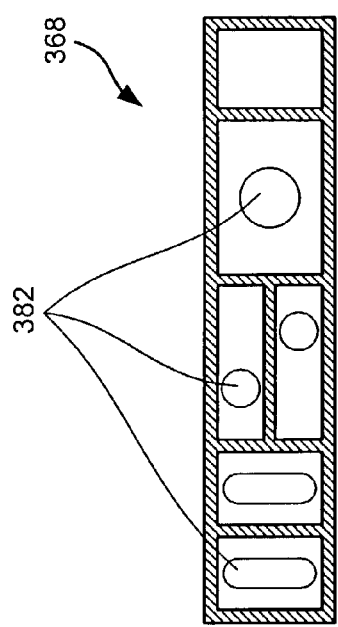
Figure 3K:
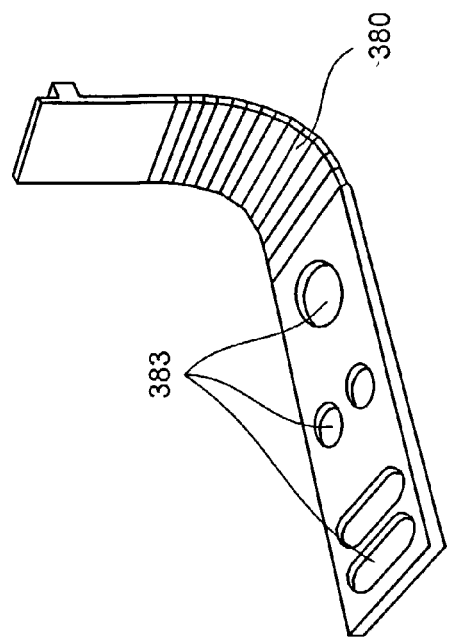
Figure 3I:
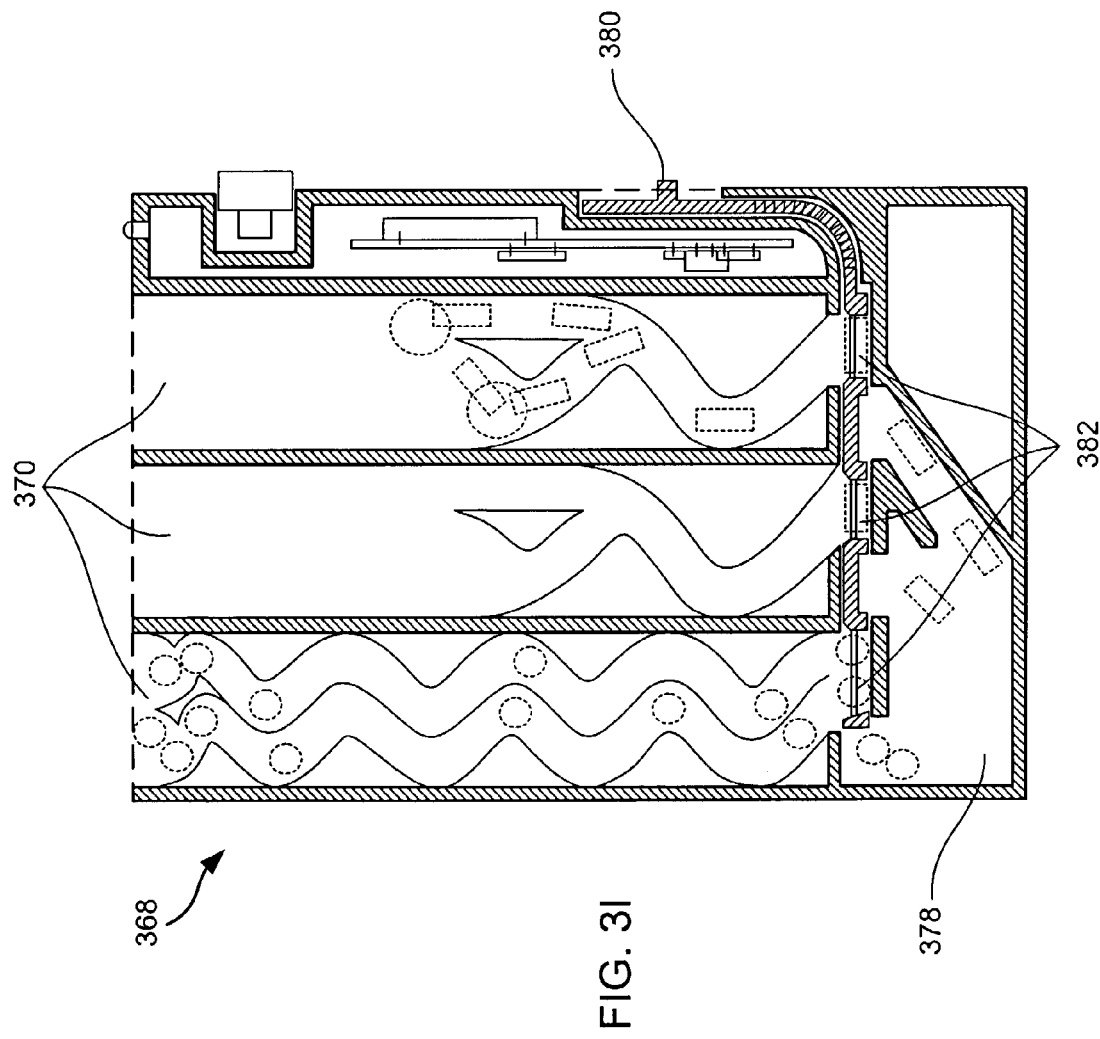

As shown in FIG. 3I, which provides a cross-sectional view of the Device 368 taken along the lines of A-A (of FIG. 3H) each of the chambers 370 may be uniquely configured (based upon the size and configuration of a given medication) to filter pills through the device and into the patient accessible chamber 378. Additionally, each of the chambers 370 may be configured without any filtering mechanisms and may instead utilize customized sleeves that are inserted into the chambers 370. In order to control the dispensing of medications from the chambers 370 and into the lower holding chamber 378, the Device may utilize, as a medication transferring device, a slide tray 380 (as shown in greater detail in FIG. 3K). The slide tray 380 may include preset openings 383 that line up with openings 382 in the bottom of the chambers 370 (as shown in FIG. 3J, which is a cross-sectional view taken along the lines of B-B in FIG. 3) such that only a given quantity of pills are dispensed from the chambers 370 and into the lower holding chamber 378 at a given time. The slide tray 380 may be manually or automatically operated. As such, this alternative embodiment provides a filtering mechanism and controlled dispensing mechanism for a multiple pill embodiment. It is anticipated that such an embodiment may be desirable for patients who consume numerous pills on a regular interval. The lower holding chamber 378 may be utilized in various embodiments to limit patient access to medications. Further, in certain embodiments, patients may not be allowed access the chambers 370 and may only have access to medication that has been dispensed into the lower holding chamber 378 in accordance with a prescribed treatment regimen. It is to be appreciated, that such access control features may be highly desirable for limiting access to medications when patients are incapable, for whatever reason, of responsibly dispensing medication. Examples of such patients may include, but are not limited to, children, addicts, those patients suffering from various stages of dementia, and others.

Referring now to FIG. 4, a block diagram of the internal hardware components utilized to provide the features and functions of the Device, for at least one embodiment, is shown in conjunction with the external hardware interfaces and components previously mentioned herein with reference to FIG. 3A and FIG. 3B. The internal hardware components may also be suitably utilized, in whole or in part, with the various alternative embodiments shown in FIGS. 3C-3K or other embodiments not shown or discussed herein.

The operation and control of the Device may be accomplished utilizing a microprocessor controller 400, for example a MicroChip Corporation 16C63 controller. The controller 400 desirably provides on-chip input/output and memory capacity, a local Universal Asynchronous Receiver Transmitter, and flexible interface related instructions. However, other controllers and/or combinations of components may be utilized to control the operation of the Device.

The controller 400 may be suitably connected to the various, previously identified, external hardware devices, such as the smart card reader 322, Talk button 318, interface port 320, LEDs 310, cap sensors 324, cap solenoids 326 (when provided), and LCD 312. Such external hardware devices may be individually connected to the processor, connected via a data bus, via a multiplexed data signal, and in various other configurations. Thus, various embodiments of the present invention may utilize various techniques and components for connecting internal and/or external hardware devices to the controller 400.

The controller 400 may also be suitably connected to an internal clock 402, which is preferably a Dallas DS 1205 time keeper chip. The Dallas DS 1205 chip provides crystal based time keeping of seconds, minutes, hours, days and months. Other clocks or oscillators may also be utilized by the controller 400 to control its internal timing and other operations.

In order to provide tactile sensory inputs, the Device may include a vibrator motor 404. Preferably, a vibrator motor may be selected which minimizes the space and energy needed for its operation, thereby allowing a reduction in the size of the Device and longer periods of operation without a recharge of the batteries or connection to an external power source.

A memory/storage device 406 may also be utilized by the controller 400 to store operating instructions, program routines, textual instructions from the Doctor and/or Pharmacists, patient compliance data, Device operating data, and other data. In one embodiment, a Microchip 24L64 32 Kbyte EEPROM memory chip is utilized to provide nonvolatile memory. However, other volatile and non-volatile memory may be utilized including, but not limited to, other types of ROM, RAM, PROM, EEPROM, and EPROM. Additionally, data storage devices such as hard disc drives, micro-cassettes, digital tape, magnetic storage devices, optical storage devices, memory sticks, memory cards, and various other devices may be utilized to provide data storage and retrieval capabilities.

Additionally, a Double Talk® RC8650 speech synthesizer 410 (from RC Systems®) may be provided with the Device. The Double Talk® speech synthesizer may be utilized to provide direct translations of text to high quality voice speech synthesis. Such voice speech synthesis capabilities enable the Device to be configured such that messages are presented in a language native to the patient and/or an assistant to the patient, while also being presentable in English. The Double Talk® chip set also provides numerous features including pitch and audio output rate control and includes an internal memory for storing up to 130 seconds of pre-recorded speech and sound effects. Additionally, the Double Talk® chip set allows the processor 400 to send text based messages directly using simple handshake status controls to pace message requests over a 3-wire serial interface. Such text based messages may also be suitably converted into visually displayed messages, for example messages displayed on an LCD 312. While the Double Talk chip set is preferred, it is to be appreciated that various other voice synthesis chip sets or codes or text to speech offline and playback systems may be utilized to provide the desired text to speech translations.

Similarly, recent advances in software based text-to-speech systems, such as AT&T's® Natural Voices™ Text to Speech engine, have made it possible to utilize software based applications and hardware based applications, to provide text-to-speech capabilities. As such, in various embodiments, the Device may utilize speech synthesizers 410 that utilize specific hardware, software and/or combinations thereof in order to provide the beforementioned text-to-speech translation and communication capabilities.

Further, an audio amplifier 412 may be provided in the Device. When provided, the audio amplifier 412 amplifies the output signal from the speech synthesizer 410 and outputs a human renderable audio signal to the speaker 316 and/or a head set (not shown) via the head set jack 328.

The Device may further include a battery monitor 408 which provides power monitoring and management functions. Based upon the power drain and utilization of the Device at any time, coded synthesizer based messaging may be provided in order to notify the patient (or other user of the Device) of service requirements such as replacing and/or recharging a battery. The battery monitor may also utilize resources on the controller to minimize the power consumption. Such power saving techniques include powering down the speech synthesizer 410 and the audio amplifier 412, as well the timekeeper chips 402. Further, the controller 400 can be configured to operate in a periodic power on mode and/or operate in a reduced power mode for the majority of the time (i.e., when the controller 400 is not called upon by the treatment regimen to notify a patient that a medication is to be taken and/or a treatment regimen is to be performed).

As mentioned previously, in those embodiments in which a cartridge may be utilized, the Device may also be equipped with a cartridge interface 414. The interface 414 enables the Device to obtain information from a compatible cartridge including the type of medication contained in the cartridge and other information. In an alternative embodiment, the cartridge itself may be programmed with some or all of the desired treatment regimen information which may be provided to the Device via the cartridge interface 414. It is anticipated that in various embodiments prescription specific information may be pre-loaded into a suitable storage device on a cartridge. Such information may then accessed by the patient via the Device and the interface 414.

Figure 5A:
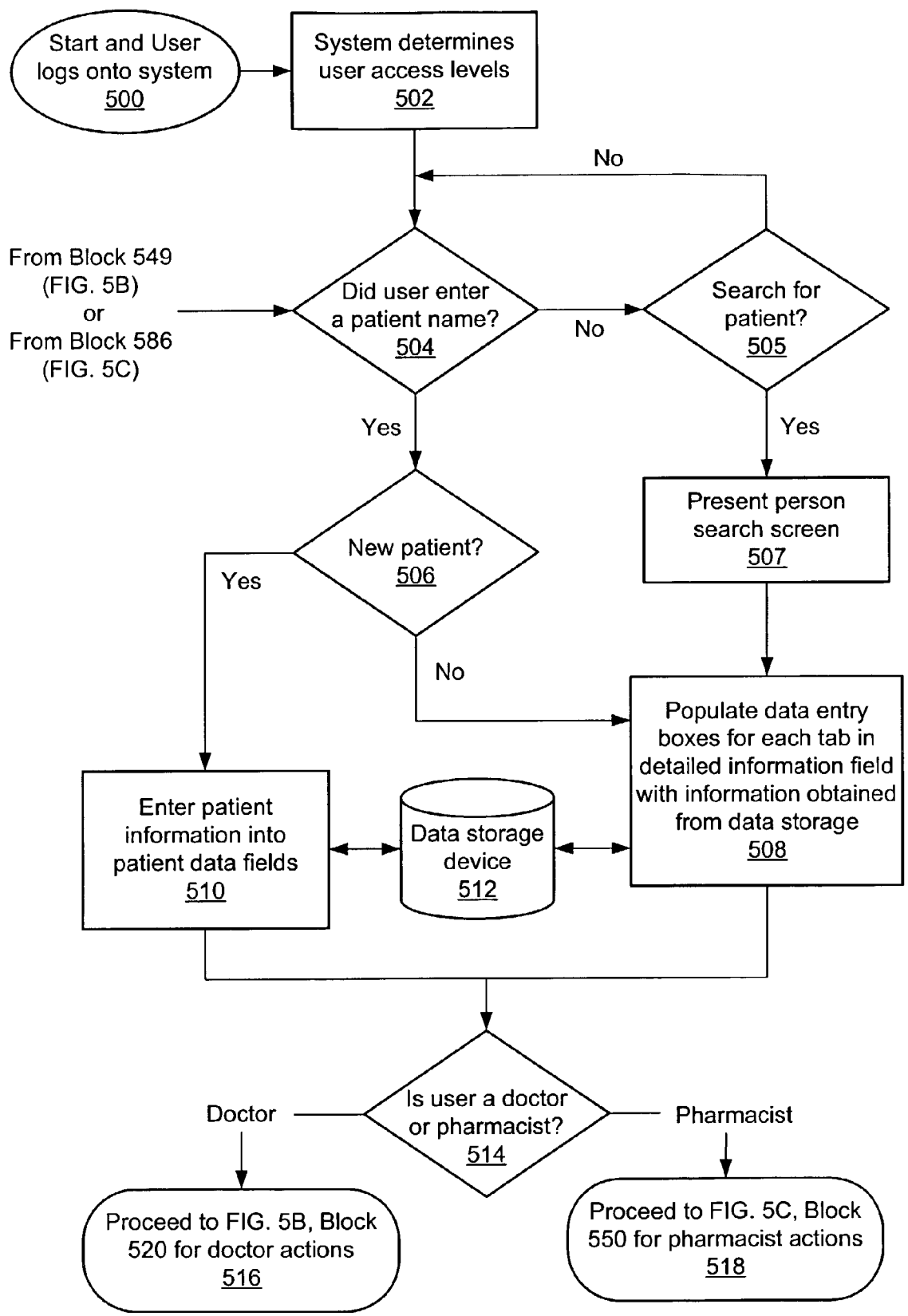
FIG. 5 is a flow chart illustrating one embodiment of a process flow by which a Doctor and a Pharmacist may utilize the Platform and the Device to provide a treatment regimen to a patient and monitor the compliance by the patient with the treatment regimen.
Figure 5B:
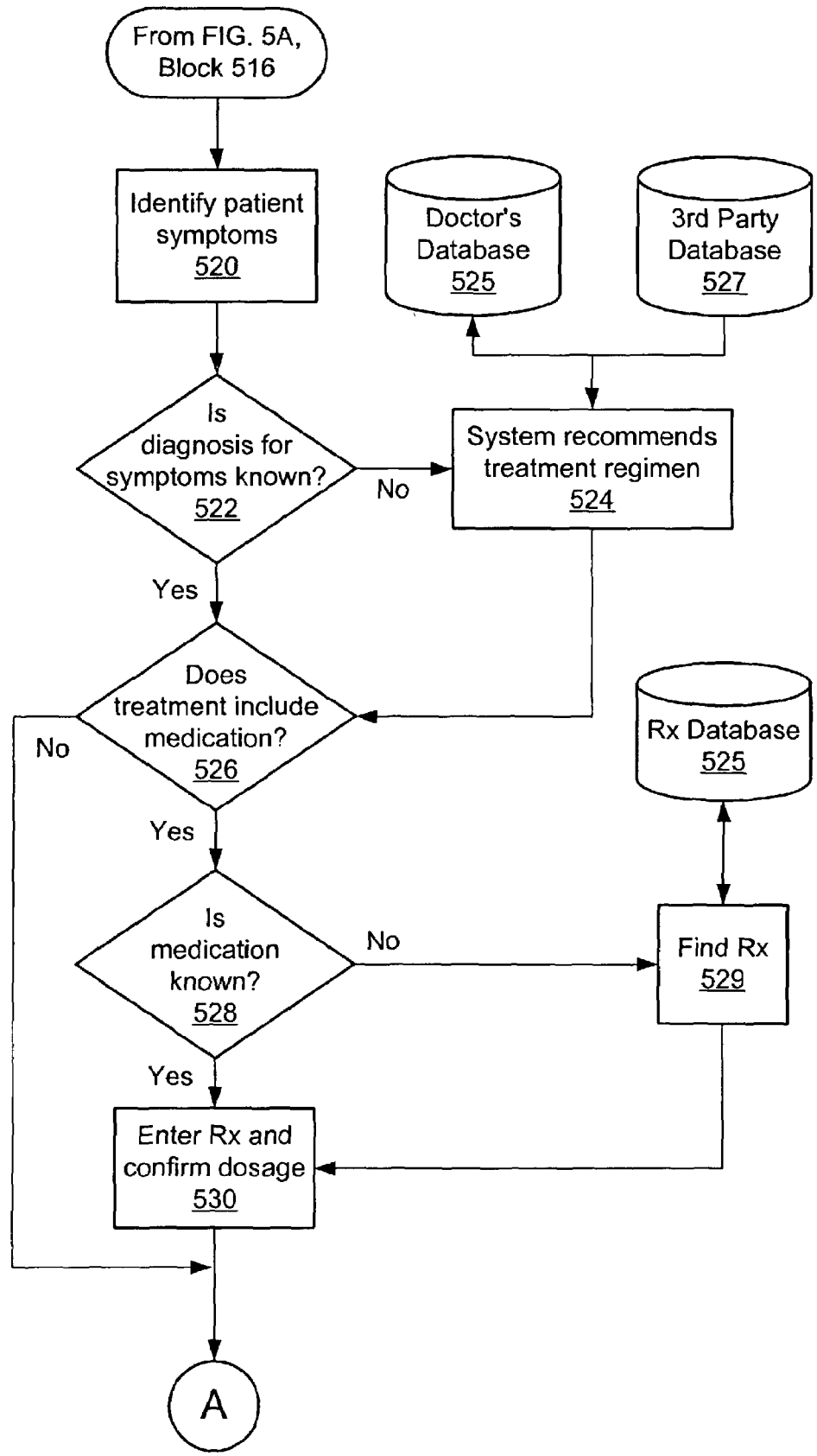
Figure 5C:
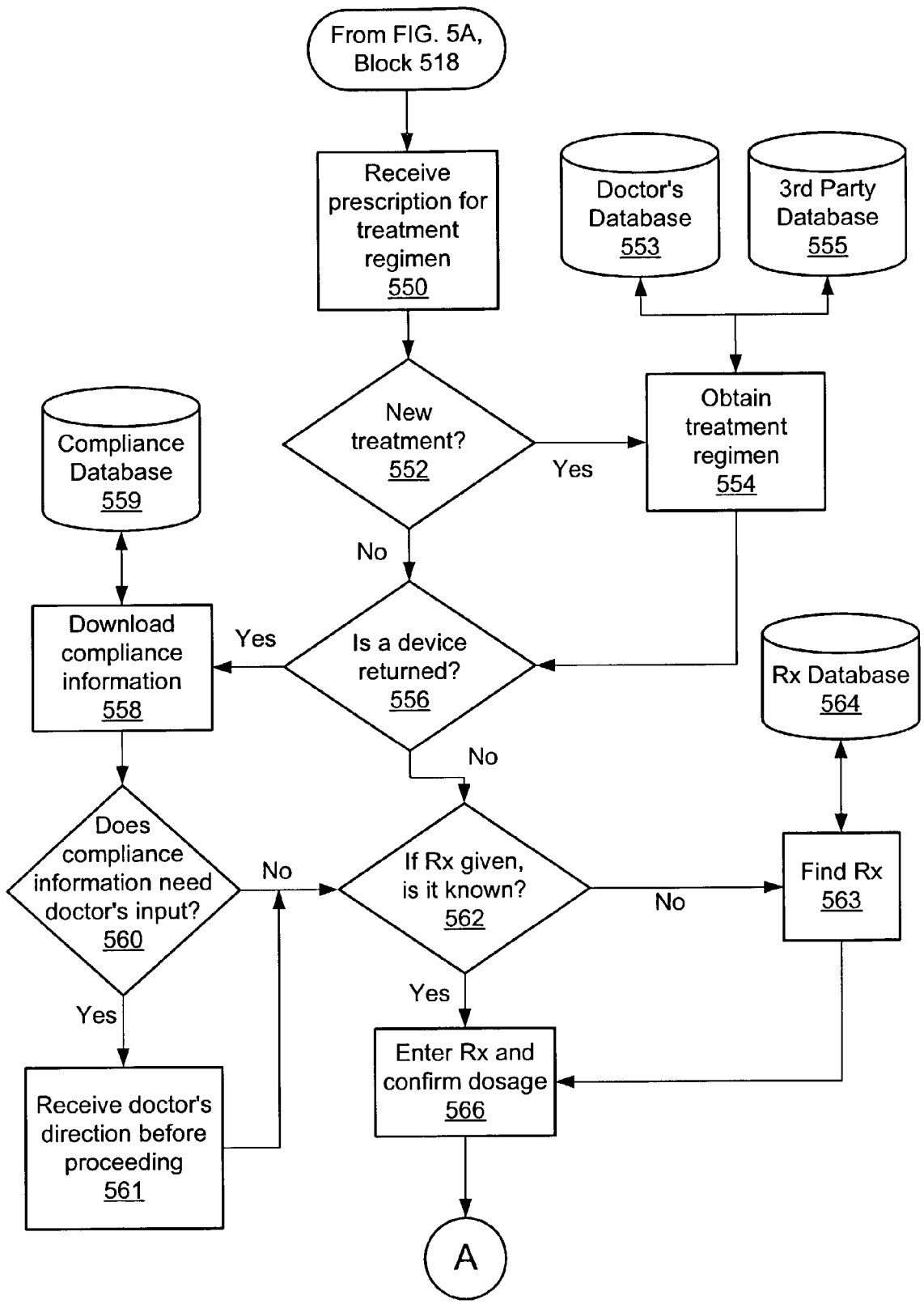
Figure 6A:
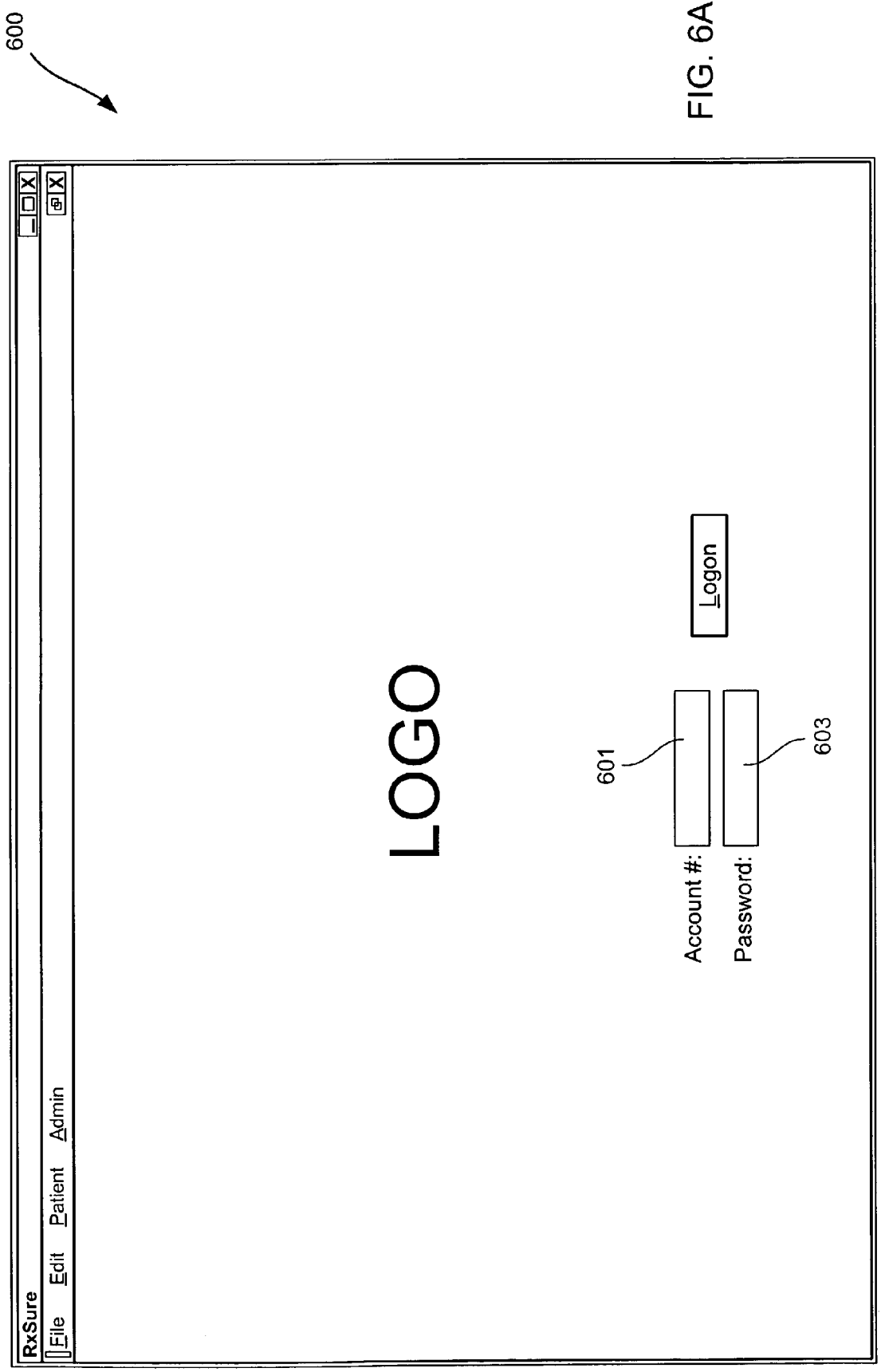
FIG. 6 is a series of screen shots illustrating the interfaces provided by the Platform for one embodiment of the present invention.

Referring now to FIG. 5 and FIGS. 6A-6T, a process flow chart and an exemplary series of screen shots are provided which illustrate how a Doctor and/or a Pharmacist interfaces with a first embodiment of the Platform in order to prescribe a treatment regimen and verify the prescribed treatment is not contra-indicated for the patient. As shown, the exemplary series of screen shots are provided by the RxSure™ program. However, other programs, screen shots, and process flows may be utilized without departing from the spirit or scope of the present invention.

As shown in FIG. 6A, the process by which a Doctor and/or a Pharmacists (and possibly a patient desiring to review their medical records) utilizes a Platform to prescribe and monitor compliance by a patient with a treatment regimen suitably begins when a Doctor or Pharmacist accesses the Logon Screen 600 (as shown in FIG. 6A). As shown in FIG. 5, this first operation is illustrated by the Start and Logon System operation (Block 500). For at least one embodiment, the Platform interfaces provided to Doctors and Pharmacists are substantially the same, with access to the various features, functions, and information being controlled by account numbers and passwords. It is anticipated that by providing a common interface, the Platform enhances communications and interaction between Doctors and Pharmacists. However, in various other embodiments, custom tailored interfaces may be utilized by Doctors and/or Pharmacists. Such custom interfaces may be provided on a collective, group, or individual basis.

Referring again to FIG. 6A, the Logon Screen 600 may include an account number field 601 and a password field 603. It is anticipated, in certain embodiments, that the Platform may be hosted on a networked server, a local server, or similar configuration wherein numerous Doctors and/or Pharmacists may access a centralized database to obtain patient and treatment information. The account number and password may be used to restrict access by authorized users to the various features and functions of the Platform, as well as the databases utilized to store patient information. Further, various other security systems may be utilized in conjunction with the Platform to control and restrict access to patient information, medication information, and other features and functions provided by the Platform or accessible from various databases accessible via the Platform. Such security systems include, but are not limited to, biomedical systems such as retinal scanners and voice or fingerprint recognition systems.

Figure 6B:
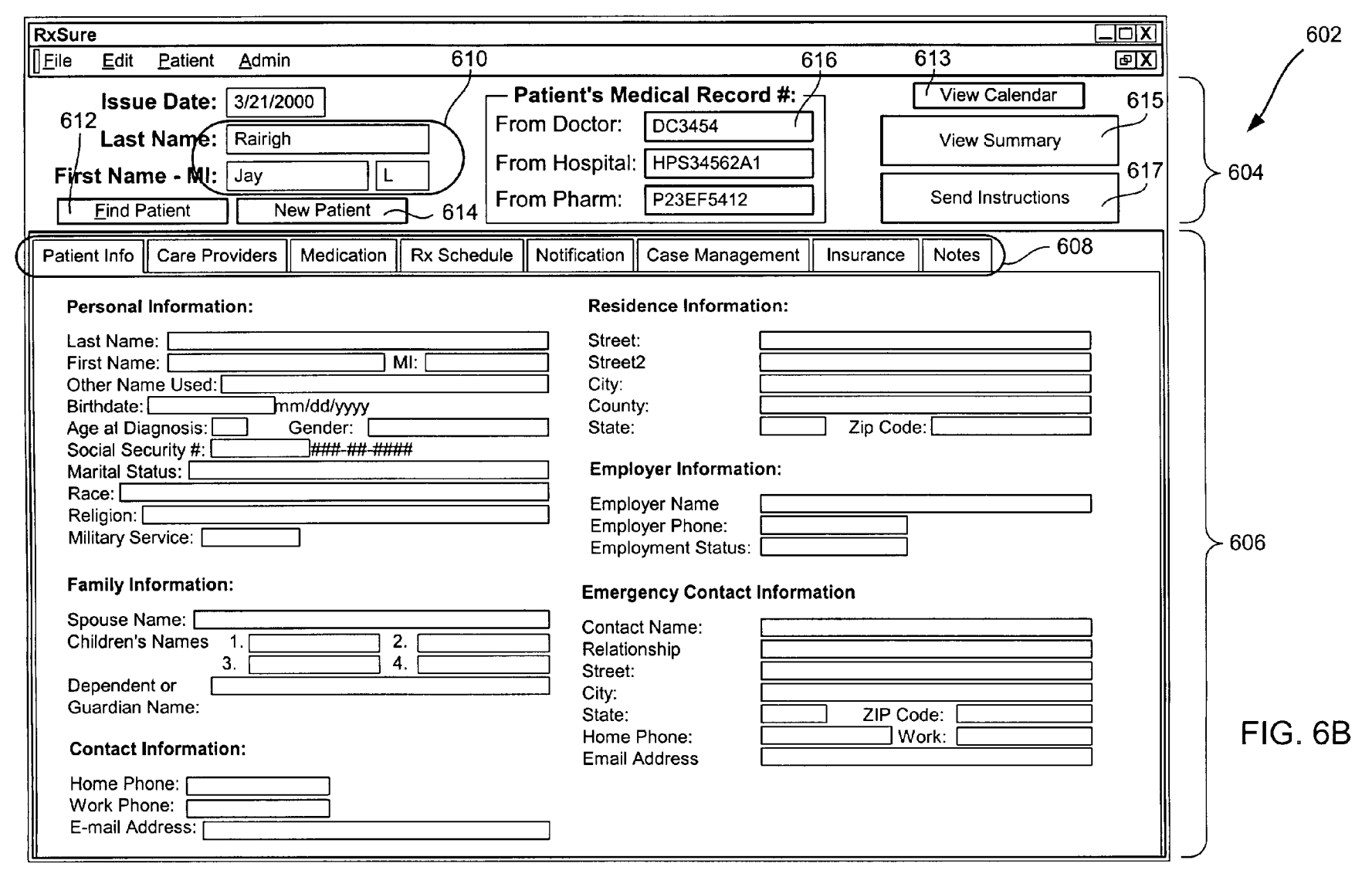

When the appropriate account number and password have been entered on the Logon Screen 600 (when required), the Platform may determine whether the user is a Doctor or a Pharmacist (Block 502, FIG. 5) and provides the appropriate levels of access to the databases, features and functions of the Platform based upon the type of user and/or the user's identity. Regardless of whether the user is a Doctor or a Pharmacist, the Platform, for this embodiment, is configured to present the Patient Information screen 602 as shown in FIG. 6B. This screen 602 provides a summary field 604 and a detailed information field 606. The detailed information field 606 enables a user to access various screens by selecting one of the corresponding tabs 608, the functions of each tab are discussed further below.

Further, the summary field 604 may be configured to contain a set of data entry boxes 610 in which a patient's name may be suitably entered. In the preferred embodiment, existing patients are suitably identified by typing in the patient's name and then depressing an enter button or "clicking" with a mouse. Existing patients may also be identified by selecting the Find Patient button 612. Similarly, new patients may be entered into the system by typing the patient's name into the data entry boxes 610 and selecting the New Patient button 614. The summary field 604 also contains data entry boxes 616 in which the user may identify a patient by a Doctor's medical record number, a hospital identification number, and/or a Pharmacies identification number. Thus, the Platform enables a user to identify a patient using various mechanisms and preferably utilizes coded numbers to help Doctors/Pharmacists find specific records more efficiently.

Referring now to FIG. 5, the Platform suitably waits or cycles until either an existing patient's name is entered or a new patient's name is entered into the data entry boxes 610, 616 as shown in operations 504 and 505, respectively. More specifically, in operation 504, the Platform queries whether the user has entered a patient name. If no patient name is entered, the Platform proceeds to operation 505 and queries whether a search for a patient has been requested by the user (preferably via the Find patient button 612) and presents the person search screen (Block 507). Further, when a patient's name is entered (i.e., the answer to the query in operation 504 is "yes"), the Platform determines whether the entered name is a new patient, as shown in operation 506.

When a user enters an existing patient's name into the data entry boxes 610 (FIG. 6B), the Platform proceeds with operation 508 and populates the data entry boxes for each tab in the detailed information field with information obtained from a data storage device 512. Further, for this embodiment, the user is provided information to which they are authorized, as determined based upon the previously entered account number and password information.

Figure 6D:
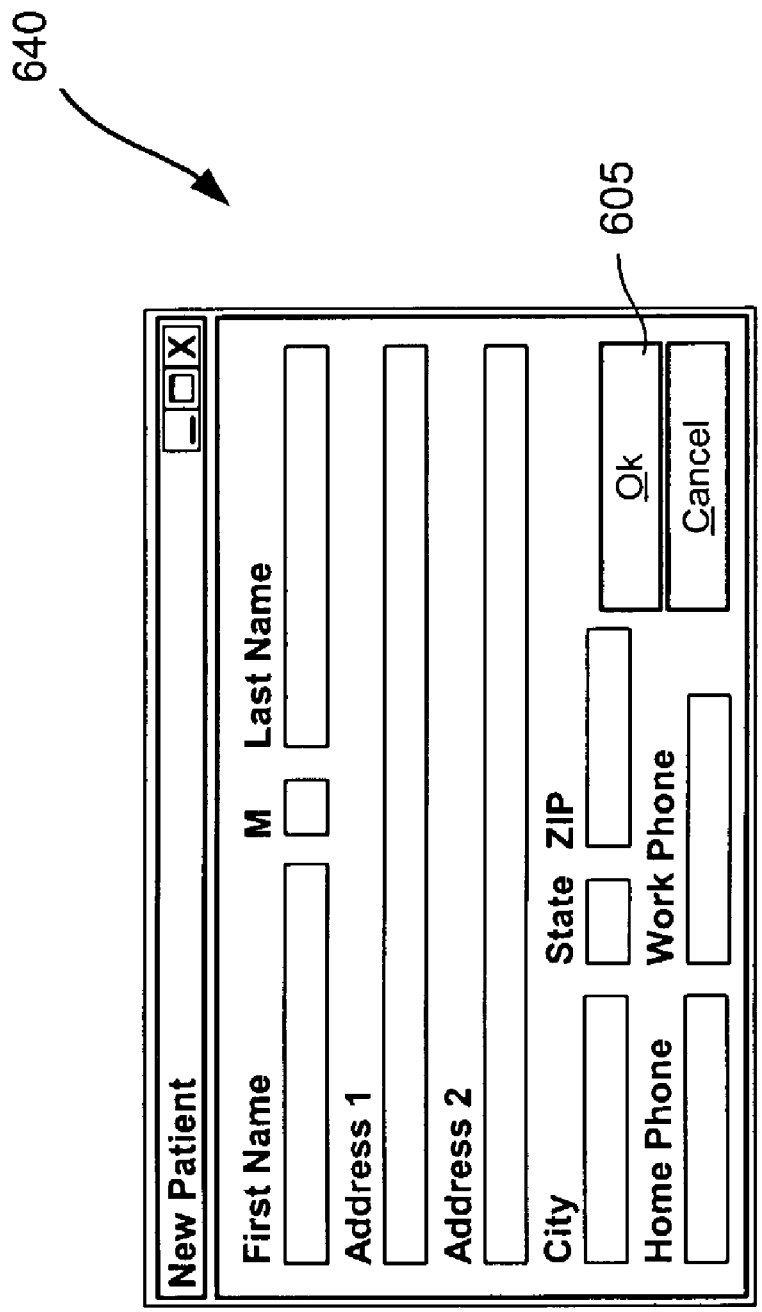

When a new patient is being entered into the Platform, the user may select the New Patient button 614. At this point, the Platform proceeds with presenting the New Patient screen 640, as shown in FIG. 6D. This screen 640 provides various data entry boxes into which the user may enter the new patient's contact information. Such information may be suitably stored in a database. Once the user selects the Ok button 605, the patient's contact information is entered into a database. The process then proceeds in operation 510 with allowing the user to enter patient information into the data boxes provided in the detailed information fields 606 (FIG. 6B) associated with each of respective tabs 608. As discussed previously with relation to existing patients, new patient information may also be entered via voice directions or other techniques (for example, scanning or copying and pasting information).

Further, it is anticipated that new patient information will be entered into the Platform by a Doctor's support staff when a patient first visits the Doctor's office or other medical facility. In one alternative embodiment, a Doctor's device (such as a PDA) may be equipped with a daily appointment schedule, wherein all of the information needed for a Doctor's routine for a given time period or day is pre-loaded into the PDA, thereby simplifying those actions necessary for the Doctor to access patient information and providing immediate access to such information.

Additionally, it is to be appreciated that various other modifications to the Platform may be provided. For example, a hospital ward may provide each nurse with PDAs or similar devices containing preloaded patient medical information for each patient on the ward.

Referring again to FIGS. 5 and 6B, the Platform also allows a user to identify a patient by a patient number. More specifically, when an existing patient is inputted into the data entry boxes 610 and the appropriate button selected, the Platform suitably calls records associated with the patient from a database. Such records are preferably associated with the patient via at least one patient identifier, for example, a Doctor medical record number, a hospital record number, and a pharmacy record number. Such identifier may be displayed in the record field 616, as shown in FIG. 6B. The patient record number identifier(s) enable authorized users to identify a patient and obtain patient information even if the patient is incapacitated and the user does not know the patient's name.

For example, hospital patients generally wear an identifying band around their wrist. These bands generally contain a patient's name and an identification number. Since large hospitals often contain patients with the same name, the medical record number identifier feature enables hospital personnel and others to quickly identify the patient in a computerized data base, for example, by scanning a bar code provided on the wrist band. The Platform may be configured such that it is compatible with bar code readers, retinal scanners, and other identification systems which enable an authorized user to quickly and accurately obtain information related to a patient.

As mentioned previously, the Platform may also be configured to enable a user to search the database for a patient's information by selecting the find patient button 612. As shown in the example of FIG. 6C, the Platform identifies those patients for which the particular user has been given access to the patient's medical records. FIG. 6C illustrates a person search screen 620 which is utilized in the present embodiment to find a patient.

As shown, this screen 620 may include various features for identifying an existing patient including a data field 622 (which presents a patient list to which the user is authorized) and an alphabet bar 624 (which, for example, enables a user to identify users by the first letter of their last name). Each entry in the data field may be selected by highlighting and "clicking" on an entry or by highlighting and selecting the Goto Selected Person button 626. Similarly, in a hands-free or voice activated system, a patient might be identified by merely reciting a patient number, a patient's name, a letter of the alphabet at which to display a listing of patients, or using other similar techniques.

Further, this screen 620 may also include a search criteria field 628 which enables the user to specify how a search for a patient is to be conducted. Drop down menus may be utilized to simplify the specifying of search conditions. A search may be initiated when the user toggles the Find Now button 630. The close button 632 allows the user to exit a search criteria and the Person Search screen 620 at any time.

For the present embodiment, a combination of look up tables, alphabetic listings and search criteria may be utilized to identify an existing patient. However, other identification and look-up techniques may also be utilized including those compatible with voice, touch screen, stylus, and other data entry systems. Thus, it is to be appreciated that the Platform may be configured to utilize various system and methods for identifying a patient and/or providing any other information to and/or from the Platform.

Referring again to FIG. 6B, the Platform may be configured to present the summary field 604 at the top of the page regardless of which of the various tabs 608 is selected by the user. The summary field 604 may contains various buttons, such as buttons for View Calendar 613, View Summary 615, and Send Instructions 617 (which upon selection instruct the Platform to send treatment regimen instructions to the Device). When the View Summary 615 button is selected, the Platform displays the prescribed medication and treatment regiment, as shown in FIG. 6M. This screen provides summary information about when a patient accessed the various features provide by the Device including opening a lid to retrieve a medication and/or accessing instructions programmed into the Device.

When the patient has been identified to the Platform, the process proceeds according to the various needs of the patient, the user, and the system. For example, when a new patient is entered into the system many of the various data fields accessible by the tabs 608 may need to be populated with relevant information. Similarly, when an existing patient (with the system) utilizes a new Doctor or Pharmacist, additional information may need to be entered into the system. Thus, it is to be appreciated that the information illustrated on FIGS. 6B-6L may be accessed and/or modified by an authorized user as needed and in any sequence as desired, provided an account number, password, and patient identifier has been provided to the Platform.

When the user of the Platform selects the Care Provider tab 644, the Platform presents the Care Provider screen 642 (see FIG. 6E) which provides (in the detailed information field 606) information pertaining to the identity of the patient's primary care physician, hospital admission information, referrals or transfers to another Doctor, and Pharmacist information. This data may be populated via various techniques, such as, using the Search for Doctor button 607 to find a Doctor from a listing. Such a listing of Doctors may be configured such that only those Doctors affiliated with the patient's insurance company and subscribing to the system are identified for referrals. Similarly, such listings may be provided for hospitals and/or Pharmacists. However, listings based upon any other criteria may be utilized as desired.

Further, this screen 642 may also provide a Consent to Release button 645 which, when selected, directs the Platform to display the Patient Consent screen 646, as shown in FIG. 6F. This screen 646 provides information, in field 613, relating to privacy provisions of the information provided by the patient with regard to the various users of the system. The Please Select box 609 allows the user (with the client's explicit and/or implicit permission) to select the user to whom access to the patient information is to be provided (for example, a specialist, a hospital, and/or a Pharmacist) and/or to transfer consent to a third party. As such, the Platform may be configured such that it is compliant with various privacy regulations and laws by providing opt-in features for the release and dissemination of personal data.

Figure 6G:
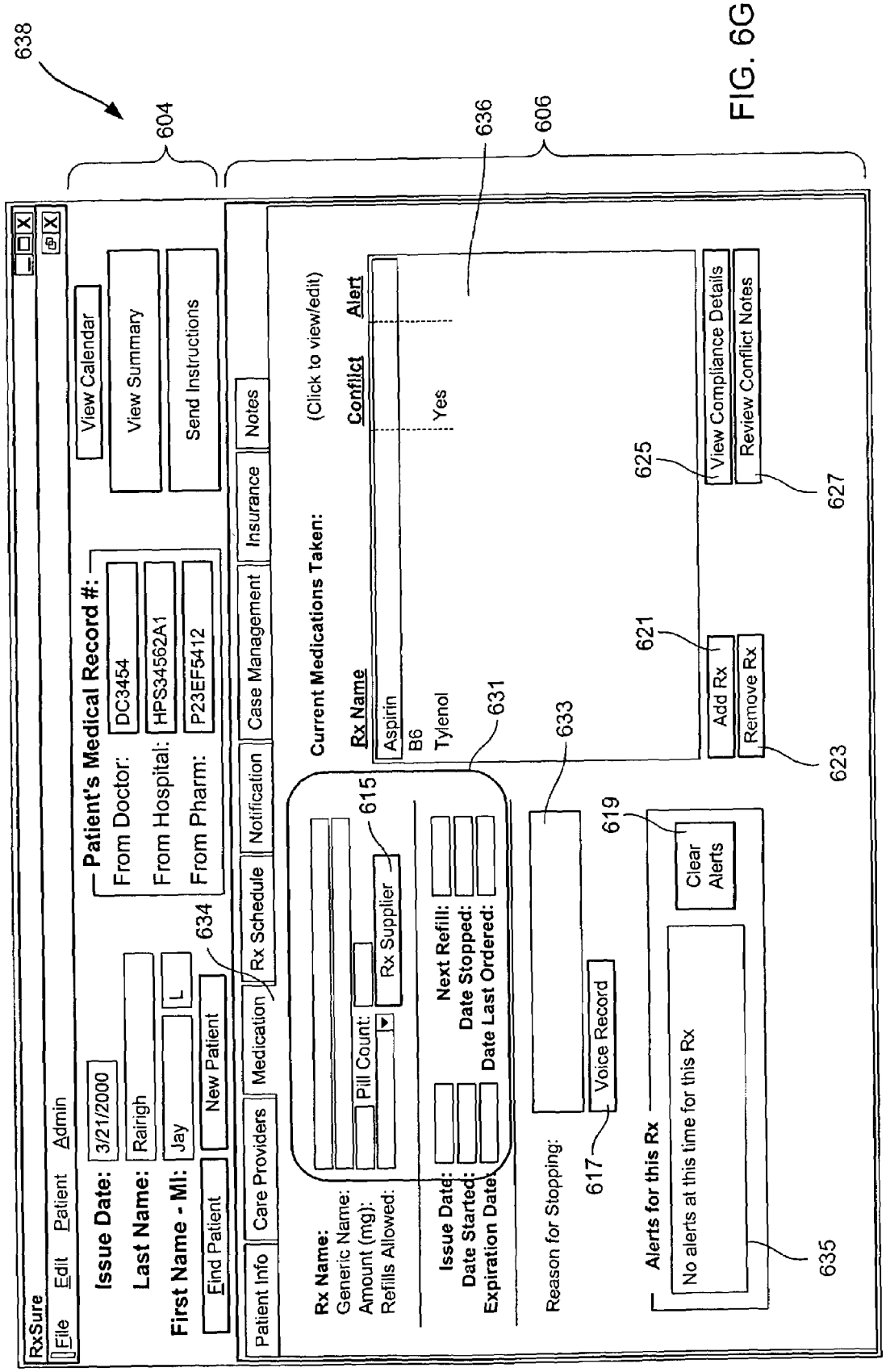

As shown in FIG. 6G, when the Medication tab 634 is selected, the Platform presents the Medication screen 638. This screen 638 may be configured to provide in the detailed information field 606 various fields, boxes and buttons related to prescribing a medication to a patient. However, it may also be utilized to prescribe non-medications to patients and other treatment regimens including vitamins, exercises, and other health related information. More specifically, on this screen 638, the Platform provides a Current Medications field 636 in which current medications/treatments that are prescribed (and have been identified to the system) for the patient may be presented. When a medication identified in the field 636 is selected, the Platform may suitably populate the Rx fields 631 with available prescription information, for example, the Rx name, generic name, dosage, pill count, number of refills allowed, issue date, date started, expiration date, next refill date, date stopped, and the date last ordered. An Rx Supplier button 615 may also be provided. This button 615 enables the user to access information on the medication that is provided by the RX Supplier. Such information, when available, may be accessed, for example, via an Internet connection. A field 633 in which a reason for stopping a medication or treatment regimen may also be provided. Such a field 633 preferably informs subsequent users (specifically, Doctors and/or Pharmacists) as to why a previous prescribed treatment was terminated.

This screen 638 may also include an Add Rx button 621 which, upon selection, enables the user to enter new prescription information into the patient's data files. Similarly, old prescriptions can be removed via the Remove Rx button 623. Lastly, the Voice Record button 617 enables the user to record treatments verbally, utilizing readily available voice recognition software.

As mentioned previously, the system may also include interfaces with at least one medication clearance system to determine whether a treatment/medication is desired for a given patient. The Current Medication field 636 provides both a Conflict and an Alert indication as to whether a treatment is contra-indicated. When such a condition exists, the Platform enables the user to access information indicating why a Conflict or Alert condition exists by selecting the conflicted treatment and the Review Conflict Notes button 627. Further, when an Alert and/or a Conflict condition exists, the user may view the Alert/Conflict in the field 635 and/or clear the Alert/Conflict via the Clear button 619.

Additionally, this screen 638 may be configured so as to allow the user to view compliance details, as determined by the Device, by selecting the View Compliance Details button 625. The Platform may be configured to display such compliance details in a format preferred by the user for example, using tables, graphs, and usage charts. One embodiment of how the Platform includes compliance information is shown in FIG. 6O, on the Compliance Summary Screen 681. As shown, this screen 681 may include a summary of compliance information for the patient on a daily basis.

Figure 6H:
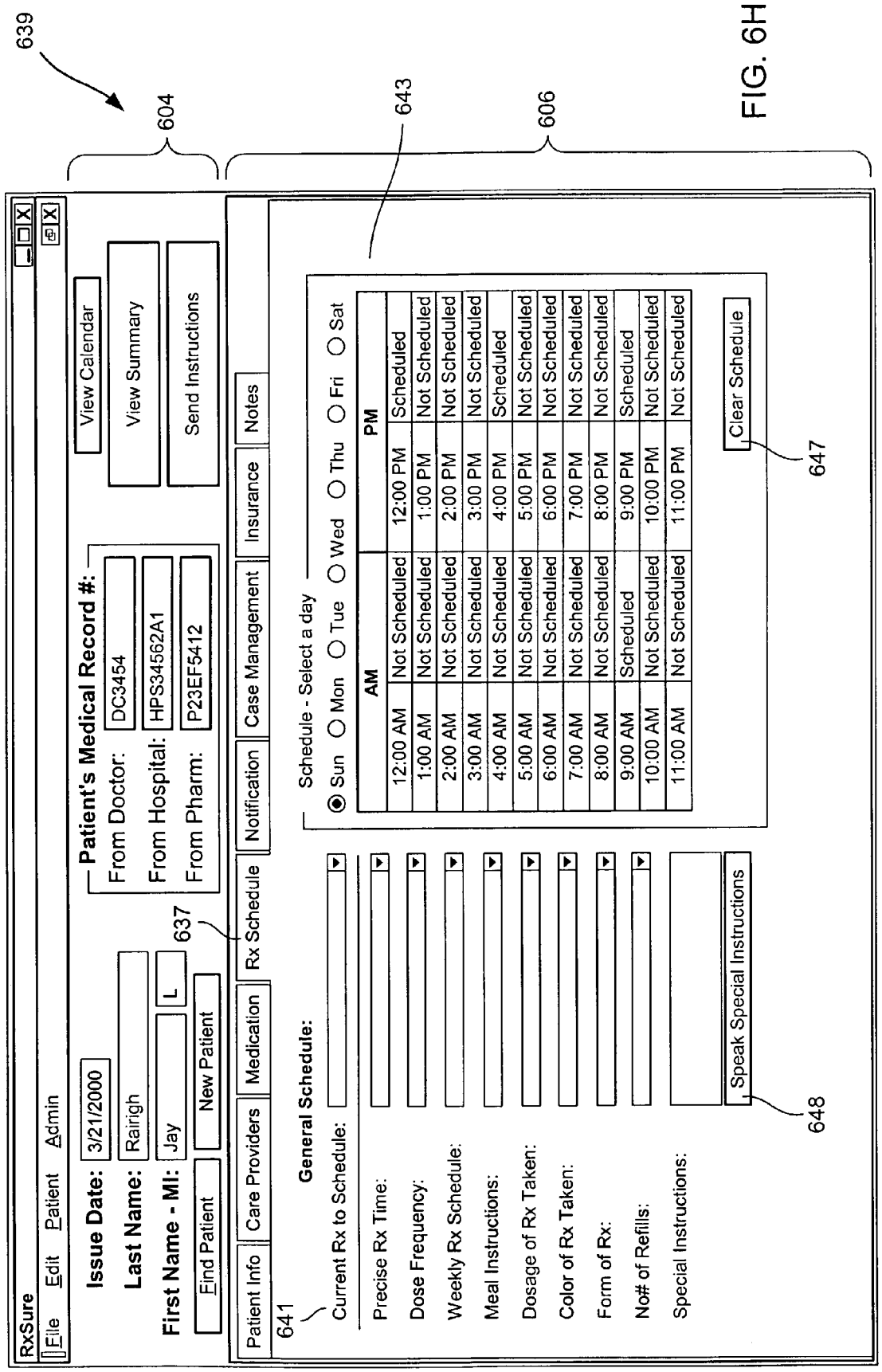

In addition to including an indication of a treatment prescribed to a user, the Platform may include fields in which the timing of the treatment, dosage, and other variables may be specified, as shown in FIG. 6H. As shown, the Rx Schedule screen 639 is preferably presented when the Rx Schedule tab 637 is selected. This screen 639 may include a General Schedule field 641 in which the user may specify the schedule for a patient's treatment regimen. A Speak Special Instructions button 648 may also be provided which enables the user to specify verbal instructions for the patient related to a treatment regimen. As discussed previously and in greater detail below, these verbal instructions may be programmed into the Device for future presentation to the patient. Additionally, this screen 639 provides a Schedule field 643 in which a user may view an entered treatment regimen by day of the week and time of the day. The Clear Schedule button 647 enables the user to quickly reschedule a given treatment regimen.

Figure 61:
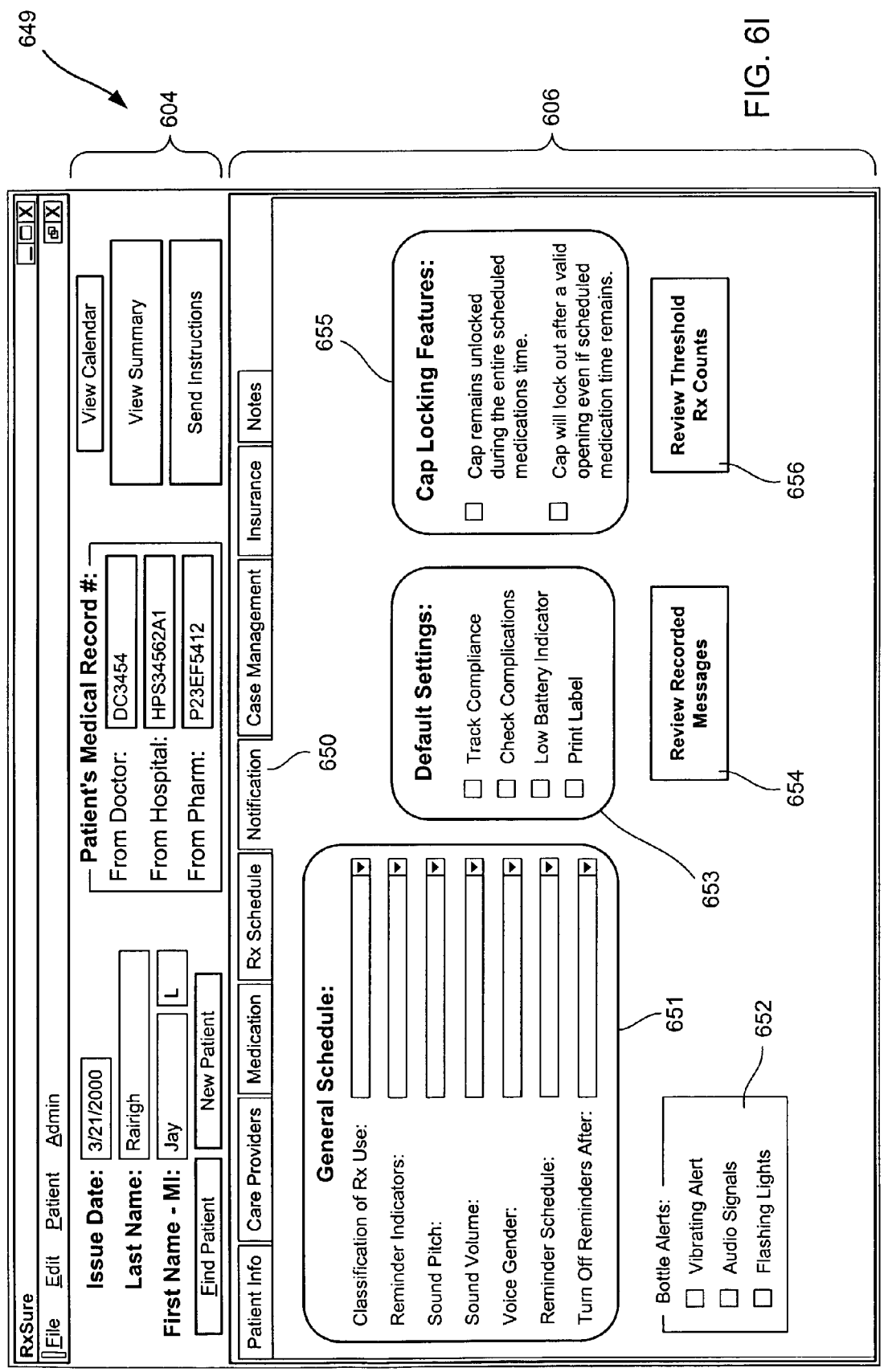

Referring now to FIG. 61, when the user selects the Notification tab 650, the Platform may be configured to present the Notification screen 649. This screen desirably includes in the detailed information field 606, additional fields for specifying Bottle Controls, Bottle Alerts, Default Settings, and Cap Locking Features 651, 652, 653, and 655, respectively. More specifically, the Bottle Controls field 651 may be configured to provide data boxes in which, among other things, the user may specify variables used to control how the Device (a.k.a., the Bottle) functions including: a classification of Rx use; Reminder Indicators; Sound Pitch; Sound Volume; Voice Gender; Reminder Schedule; and Turn Off Reminder After. The precise settings for each of these functions may vary depending upon the particular configuration of Device utilized.

Further, the Bottle Alerts field 652 may include various methods for notifying a patient, via the Device, that it is time for a programmed event, for example, administering a treatment regimen by consuming a prescription medication. These methods of notifying the patient preferably include utilizing a vibrating, audio, or visual signal. However, the Device may also be configured to include other perceptible indicators and is not limited to the preceding indicators.

The Default Settings field 653 enables the user to specify how the Device is to operate in a default mode. Such settings include whether to Track Compliance, Check Complications for treatment regimens, enable the Low Battery Indicator, and whether a Label should be printed.

Further, the Review Recorded Messages button 654 enables the user to review any messages currently recorded for the patient regardless of whether such messages have or have not been programmed into the Device. When this button 654 is selected, the Platform displays the Messages Screen 674, as shown in FIG. 6N. Additionally, this screen 674 can be configured to present both generic messages and messages specifically tailored for a specific patient. FIG. 6S provides an illustration of a scheduling screen utilized to identify when messages are to be presented and also to download Device information by selecting the Download Device Events button 686. When this button 686 is selected, the Platform displays the Download screen 689, as shown in FIG. 6T. As shown, this screen 689 enables the user (Doctor or Pharmacist) to select the download format, time periods, patient, prescription and other information recorded by a Device. Such downloaded information may be utilized to determine compliance, track usage and other functions.

Referring again to FIG. 6S, this screen 685 also enables the Doctor/Pharmacist to download complication information by selecting the Download Complications Notes button 687. When this button 687 is selected, the Platform suitably displays the Complications Notes screen 683, as shown in FIG. 6Q, wherein information on complications is presented to the user. Similarly, the Review Device Messages button 688 enables the user (Doctor/Pharmacist) to review messages programmed into the Device and edit and remove messages, as shown in FIG. 6N.

As shown in FIG. 6N, the Messages screen 674 also provides a Messages Selection field 676 in which the user may select a previously recorded message to review in the Message Text field 675. Further, this screen 674 enables the user to Edit 677 messages, Remove Messages 678, Turn On/Off 680 the message feature on a given Device, and Speak 679 new messages.

In alternative embodiment, the Platform may be configured so that a patient can retrieve treatment regimens from the system even if a Device is not available. Such feature enables users who forget to take their Device with them (for example, on a vacation) to call into the system and retrieve treatment information. Similarly, this feature enables Doctors and/or Pharmacies not configured to utilize the system to also retrieve treatment regimen information from the system.

The Cap Locking Features field 655 is also provided on this screen 649 (FIG. 6I). This field 655 is provided for those embodiments of a Device in which a locking cap mechanism is utilized. It is anticipated that this feature, which allows the user to specify when a patient can access a medication, will be very desirable for patients who have a history of abusing prescription medications. Similarly, the Review Threshold Rx Counts button 656 allows a user to review on the Threshold Rx Counts screen 684 (as shown in FIG. 6R) medication thresholds that may be predetermined by Doctors and/or clinical researchers. These thresholds provide benchmarks for measurement of dosage and frequency and are often utilized to wean patients off of addictive medications or to prevent such addictions from occurring.

Figure 6J:
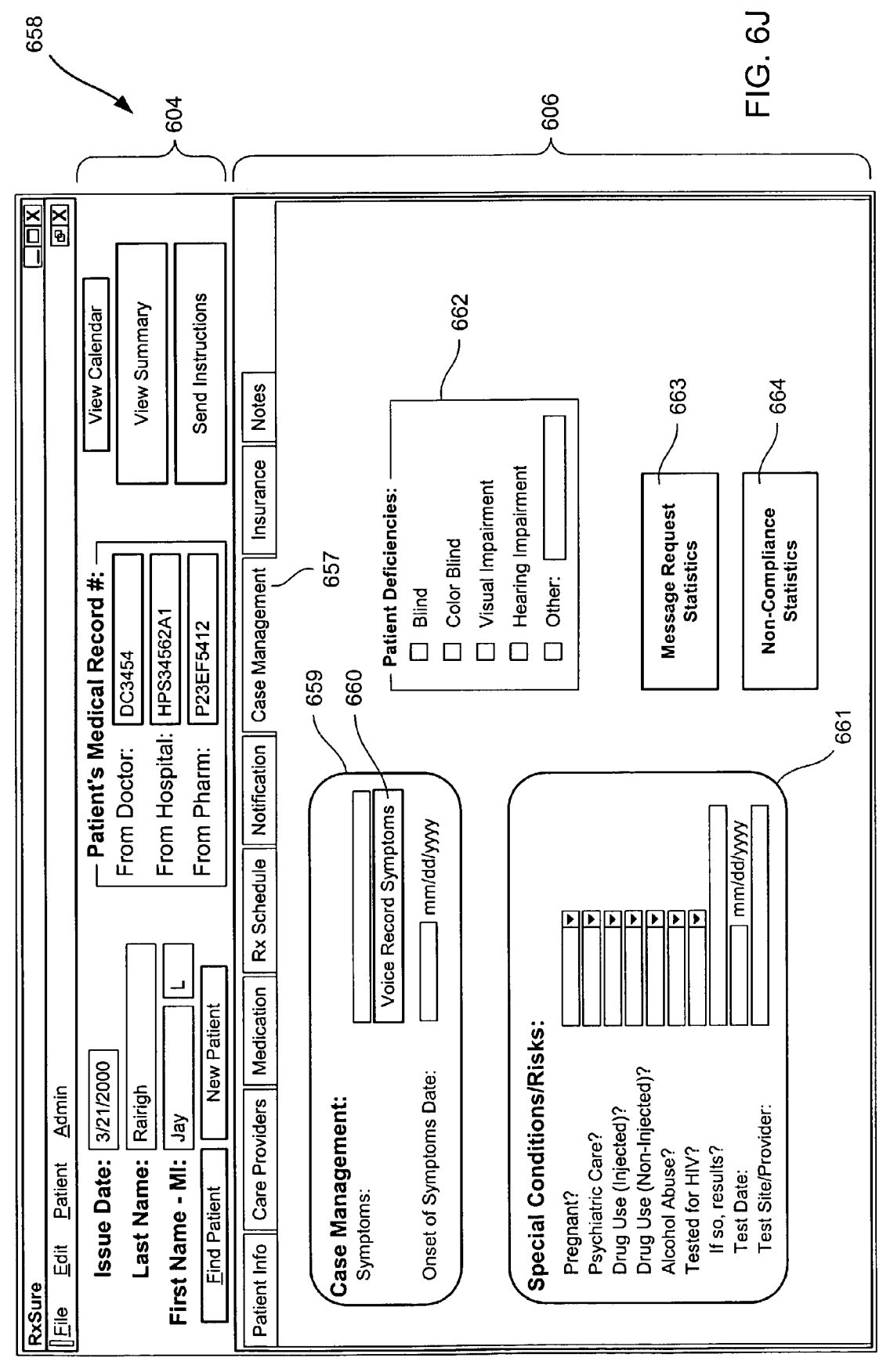

Referring now to FIG. 6J, when the user selects the Case Management tab 657, the Platform presents the Case Management screen 658. As shown, this screen 658 provides a Case Management field 659 in which the Doctor may enter information pertaining to the patient's symptoms and/or physical/medical condition. Upon entry of the any necessary information the Doctor, as desired, may access expert systems, third party databases, on-line periodicals and tutorials, and other information in order to determined the cause (if known in the medical community) of the patient's condition, identify treatment regimens, and access other information.

Additionally, this screen 658 includes the Voice Record Symptoms button 660 which enables the Doctor to record the patient's symptoms orally. Such a feature may be desired, for example, when a second opinion is needed or other consultations are to be performed. Additionally, other buttons can be added which enable the Doctor to attach links to data files containing, for example, medical image files, test results, lab results, consulting opinions and other information. Thus, various embodiments of the present invention may be configured to link or otherwise provide any medical information that is can be presented over a communications network.

Further, this screen 658 provides a Special Conditions/Risks field 661, in which the user may enter information relating to the patient's specific medical condition. Similarly, a Patient Deficiencies field 662 is provided which identifies any physical difficulties the patient may have. This information is preferably utilized in programming the treatment regimen into a Device since, for example, a deaf person generally may not desire to receive an audible signal but does desire to always receive a tactile signal.

The Message Request Statistics button 663 enables the user to determine how often a patient has requested information from the Device and what type of information was requested. One example of such statistics is shown in FIG. 6P. These statistics enable Doctors and Pharmacists to identify problem areas in the patient's use of the Device. For example, a patient who repeatedly requests a given message to be repeated twice, might be doing so because the message was spoken too quickly during the initial recording and is therefore hard to understand. These statistics can also provide the Doctor with additional insights into the patient's non-specified condition (for example, hearing loss, comprehension challenges, or other ailments). Additionally, a Non-Compliance Statistics button 664 is provided and enables the user to determine the patient's compliance history for a previously prescribed treatment regimen.

Figure 6K:
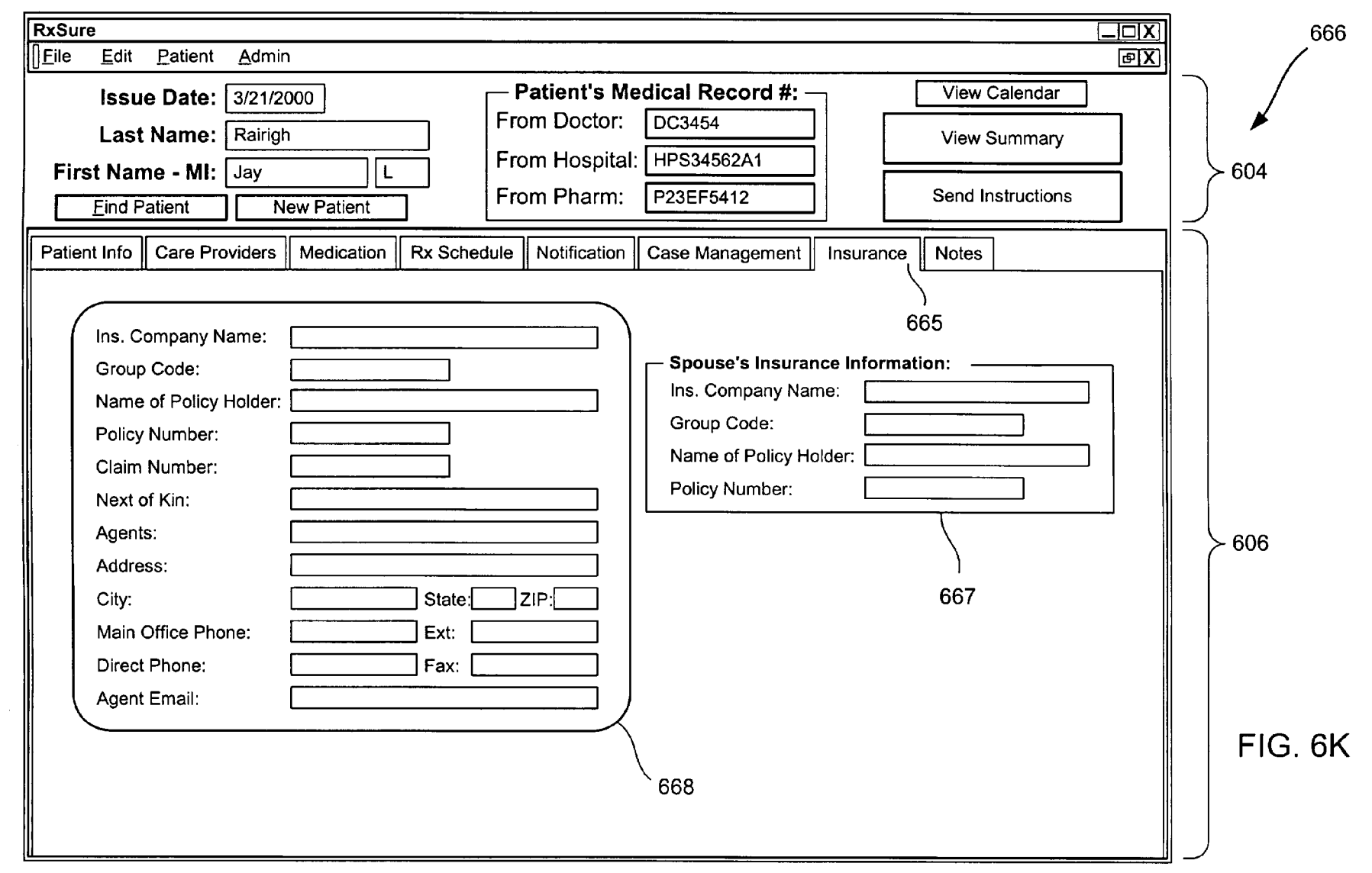

Insurance information for the patient may also be provided to and/or accessed via the system by selecting the Insurance tab 665. Upon selection of this tab 665, the Platform presents the Insurance screen 666 as shown in FIG. 6K. This screen 666 includes an Insurance information field 668 and a Spouse's Insurance Information field 667. Additionally, in alternative embodiments, links to the designated insurance provider are provided (for example, via a pull down menu). Such links enable the user to directly contact the insurance provider for the specific patient.

Figure 6L:
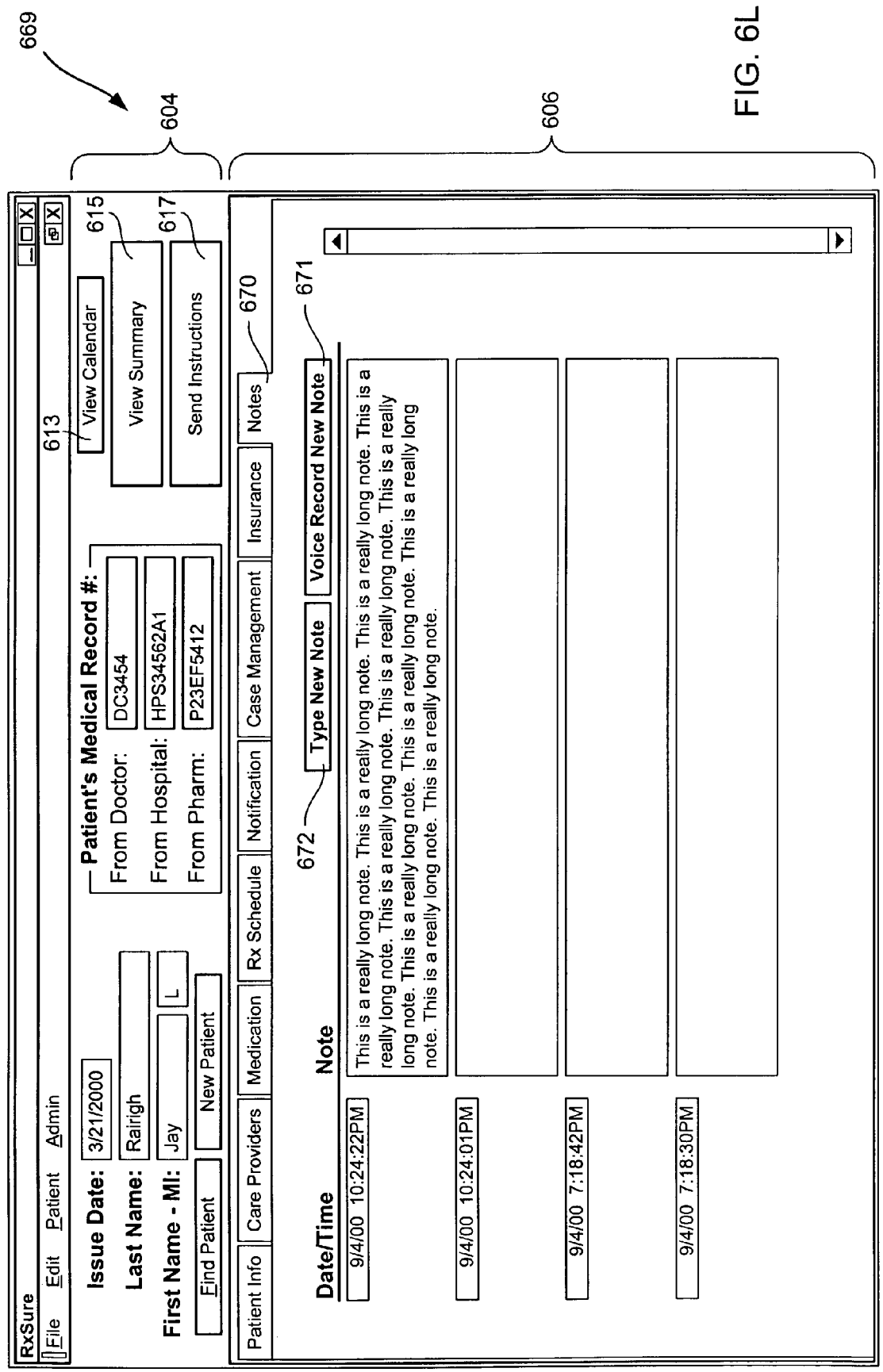
Figure 6N:
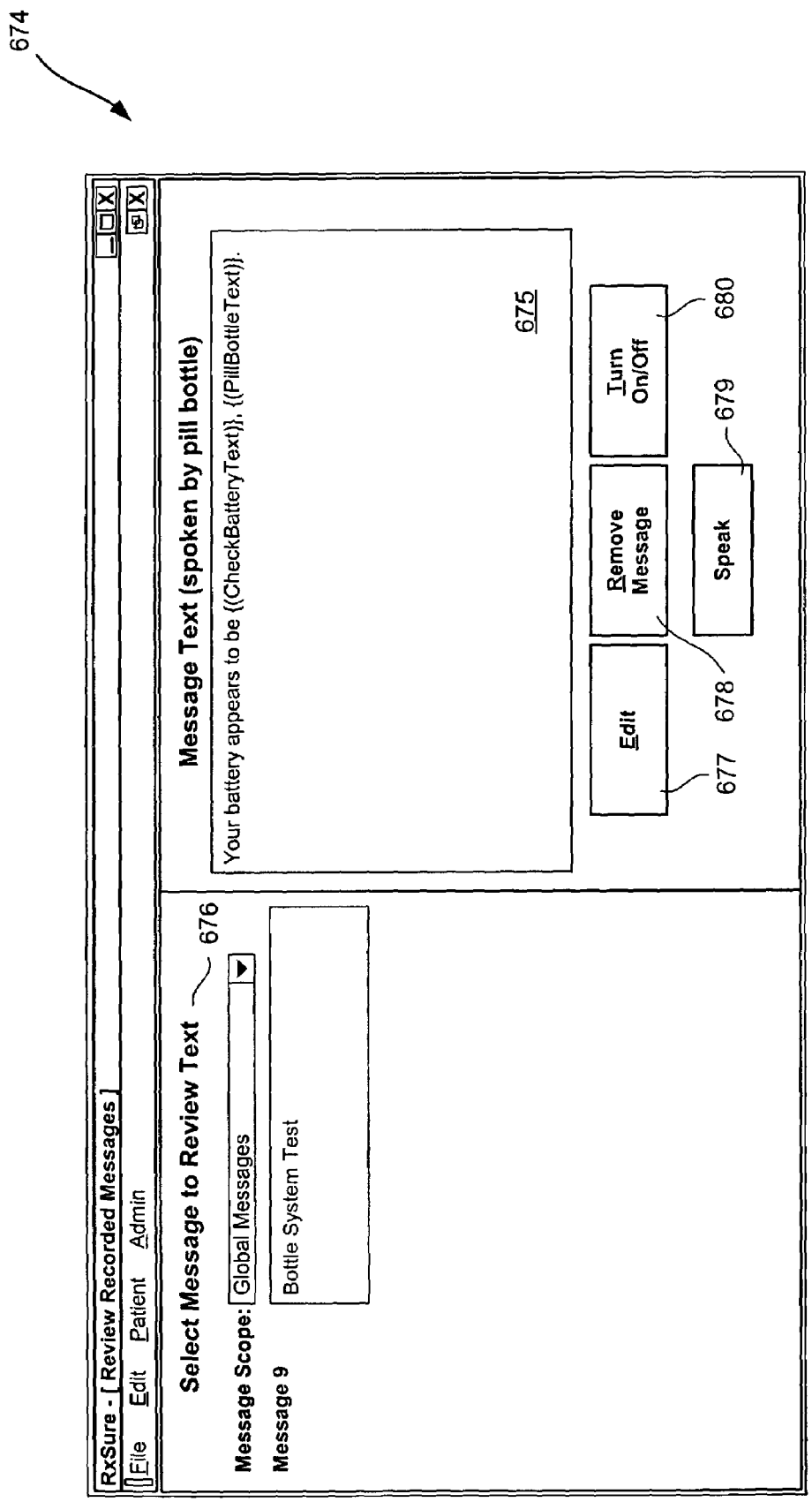
Figure 6S:
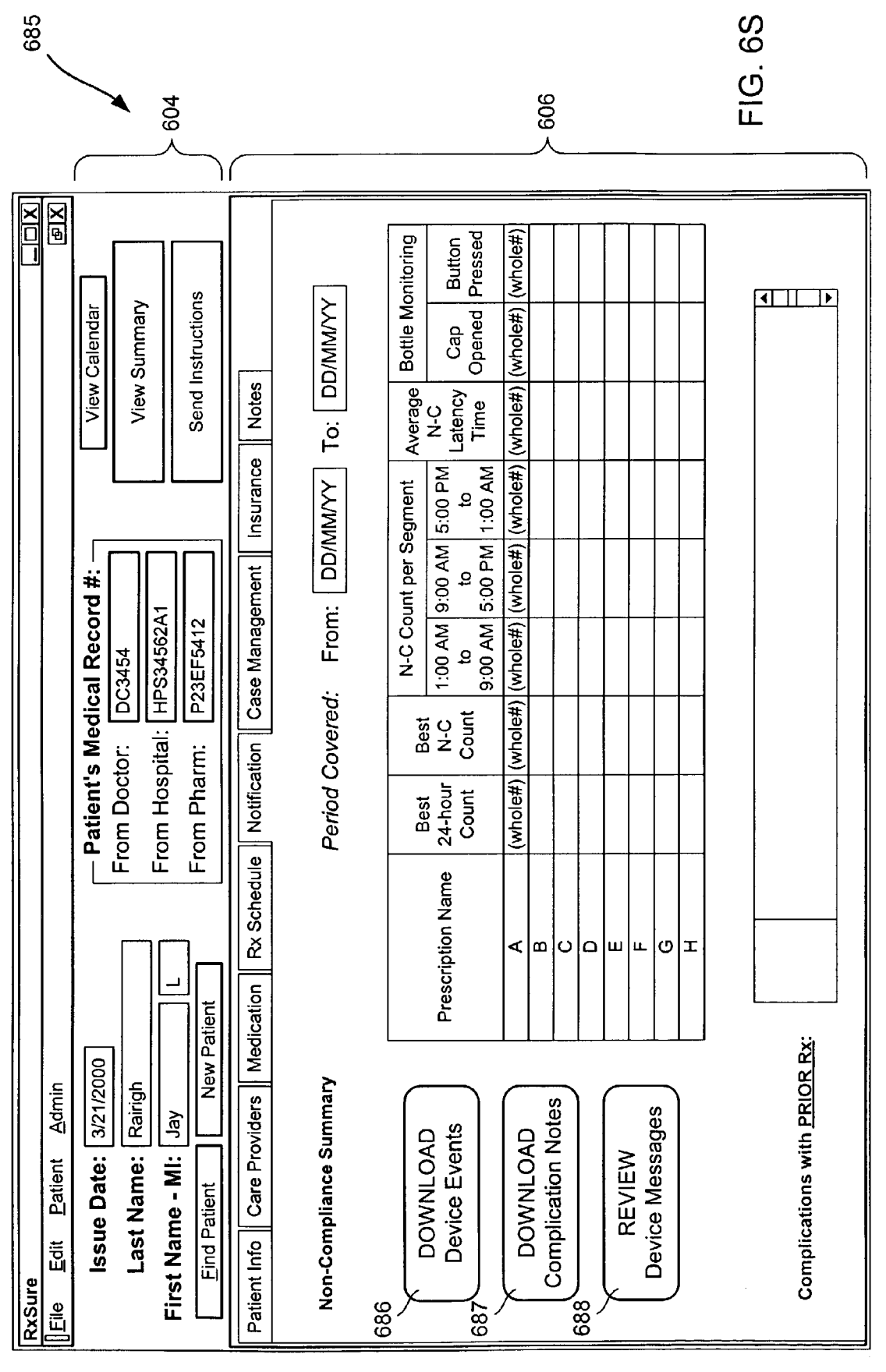

The Platform also includes a Notes screen 669 which is presented upon selection of the Notes tab 670, as shown in FIG. 6L. On this screen 669, notes previously entered into the Platform (and the patient's data file) may be displayed in the detailed information field 606. Additional notes may be added by typing the note (via button 672) and/or selecting the Voice Record New Note button 671 and orally presenting a new note which is then suitably converted to text by voice recognition software. Once a note is entered into the Platform, for one embodiment of the present invention, the note is permanently saved and can not be deleted or erased. Other embodiments, however, may not require notes to be permanently saved. Additionally, the preferred embodiment only allows a Doctor/Pharmacist to enter notes for a given day, and does not allow the Doctor to post-date entries. However, it is to be appreciated that in alternative embodiments, such post-dating and/or modification of notes may be possible.

As mentioned previously, the Platform includes, in the summary field 604, the View Summary button 615. Upon selection of this button 615, the Platform presents a summary page of the treatment regimen(s) prescribed for the patient. This summary includes as little or as much information desired by the user. FIG. 6M provides an example of such a summary in which a Rx schedule for a given patient is provided. Additionally, it is to be appreciated that other time periods may be utilized.

Referring again to FIG. 5A, the process by which a Doctor and or a Pharmacist enters and/or obtains the information necessary to identify a patient and then either prescribe a treatment regimen or actually provide a prescription medication to a patient has been described. Since only authorized users are allowed access to the various screens, features and functions of the Platform, the processes by which a Doctor utilizes the Platform and a Pharmacist utilizes the Platform may vary. FIGS. 5B and 5C illustrate embodiments of the processes which may be utilized by Doctors and Pharmacists, respectively, when interfacing with the Platform after the user and a patient has been identified.

As shown in FIG. 5B, upon identifying the user as a Doctor (Blocks 514 and 516) (regardless of whether the patient is new), the process by which the Doctor utilizes the Platform preferably continues with the Doctor identifying the patient's symptoms (Block 520). As stated previously, the Case Management screen 658 provides data fields in which the Doctor can specify the patient's conditions.

The process may then continue with a determination by the Doctor as to whether expert systems and other information for example a Doctor database 525 or $3^{rd}$ party treatment database 527 are to be consulted in order to assist in the diagnosis of the patient's medical condition. In short, the process queries the Doctor as to whether a diagnosis and course of treatment for the patient's symptoms is known by the Doctor (Block 522). When the diagnosis is not known, the system may be configured to upon request or automatically assist the Doctor with determining the cause(s) of the patient's condition and to provide recommendations for a treatment regimen (Block 524).

The process also may be configured to issue queries as to whether a medication is to be prescribed as a part of the treatment regimen (Block 526). When a medication is to be prescribed, the process flow continues with a query as to whether the Doctor knows the desired medication or whether assistance from an Rx or other database is desired (Block 528). It is to be appreciated that this step commonly will be accomplished by the Doctor. However, prompts and other querying features may be provided in the Platform as needed and/or desired in specific applications.

If the medication to be prescribed is not known by the Doctor and/or the Platform itself, the Platform may be directed to access various Rx databases (Block 525) to determine which medication(s) to prescribe (Block 529) for the patient's given condition. Further, once the medication has been identified (either by the Doctor or via the Platform), a dosage is entered and confirmed (Block 530).

At this point, the Platform, preferably automatically but not necessarily, determines whether the new treatment regimen (which may, but does not have to, include a medication) conflicts with any of the patient's current or past medications and/or conditions (Block 532). The system may accomplish these conflict checks by accessing a third party provided conflicts database (Block 533). When a conflict exists, the Platform generates an alarm which notifies the Doctor of the conflict. The Doctor may select an alternative treatment (Block 534) by accessing, as necessary, other medical databases (Block 535), and/or overriding any conflict alarms. For example, when the risk of a conflict is outweighed by the potential benefit of a medical treatment, a Doctor may decide to override a conflict alarm. In alternative embodiment, the Platform may be configured to require the Doctor to enter a note explaining why a conflict is to be overridden, thereby establishing a record of overrides and the rational therefore.

Once any conflicts have been cleared or overridden, if any, the process preferably continues with a query as to whether a Device has been previously used by the patient (Block 536). If so, the Platform may obtain compliance information (Block 537) from either the Device itself (if available) or from another Doctor's or Pharmacist's compliance database that is accessible via the Platform (Block 539). Such compliance information may be reviewed by the Doctor and corrections in the treatment regimen, when necessary, may be made (Block 538). It is to be appreciated, that when substantial changes are made to a treatment regimen all or part of the process flow of FIG. 5B may need to be repeated, as specified by the Doctor and/or the specific system configuration.

At this point in the process, the Doctor has preferably seen the patient and prescribed a treatment regimen that has been verified as being acceptable for the patient (or one in which any conflict alarms have been overridden). Such treatment regimen may also be entered as a custom therapy into the Platform, if not previously entered (Block 540).

The Doctor may then provide the prescribed treatment regimen to the patient and/or the patient's Pharmacist (Block 542). Further, a notification may be sent to the Doctor identifying that the Pharmacist has received the prescription. The Doctor's Platform may also receive confirmation from the Pharmacist that the patient has received the medication (when necessary) (Block 544) and such information may be entered manually or automatically into the Doctor's database (Block 546) or a centralized database, as particular needs dictate. At this point, the Doctor's processing is accomplished for a specific patient, and processing may then end or proceed with another patient (Block 547-549).

Referring now to FIG. 5A, as shown in Block 518, after the user (who is a Pharmacist) enters an account number and password, and identifies a patient who is requesting the dispensing of a prescribed medication, the process flow preferably continues in FIG. 5C at Block 550.

As shown in FIG. 5C, the Pharmacist process continues when the Pharmacist receives a prescription for a treatment regimen from a patient directly, via a smart card (as discussed previously herein), from a Doctor electronically (Block 550) or otherwise. At this point, the Platform utilized by the Pharmacist (which may, but does not have to be, the same Platform utilized by the Doctor) determines whether the prescription is for a new treatment or an old treatment (Block 552). If the treatment is for a new treatment, the process flow continues (Block 554) with the Pharmacist's Platform obtaining the treatment regimen from either manual input by the Pharmacist, the Doctors' database (Block 553), and/or a third party treatment database (Block 555).

When the prescribed treatment regimen is not for a new treatment, the process flow may continue with a query as to whether the patient is returning a Device containing information for a previously prescribed treatment regimen (Block 556). The determination as to whether a Device is being returned by the patient may also be accomplished when a new treatment regimen and/or a new prescription is being provided by the patient to the Pharmacist, and/or at other appropriate times.

When a Device is being returned by the patient to the Pharmacist, the Platform downloads the compliance information from the device (Block 558). The compliance information may also be obtained from and/or provided to the compliance database (Block 559). At this point, a determination may be made as to whether the compliance information is of such a nature that a Doctor's input is needed before the Pharmacist may provide the prescribed medication and/or treatment regimen to the patient (Block 560). Such a situation may exist, for example, when the patient is abusing prescription medications.

When a Doctor's input and/or direction may be needed, based upon the compliance information recorded by the Device, the process flow may be configured to enter a wait stage until directions and/or approvals from the prescribing Doctor are obtained (Block 561).

Once any compliance information obstacles have been overcome, if any, the processing continues with a query as to whether the prescribed medication is known to the Pharmacist (Block 562). When the prescribed medication is not known to the Pharmacist, the Platform may search for and hopefully find information pertaining to the prescription (Block 563). Such information may be obtained from internal and/or $3^{rd}$ party prescription databases (Block 564), as necessary.

Next, the Pharmacist enters into the Platform the prescription and confirms the dosage of the medication to be provided to the patient (Block 566). As discussed previously during the discussion of the Doctors phase, the Platform performs a conflict check and determines whether the new treatment and/or medication regimen conflicts with other previous and/or current treatment regimens (Block 568, FIG. 5C1). In performing this conflicts check, the Platform uses any available conflicts databases (Block 569) as necessary. Further, when a conflict arises the Platform instructs the Pharmacist to notify the Doctor and wait for an alternative treatment or medication regimen to be provided by the Doctor (Block 570). However, the Platform preferably does not create a conflict alarm when the Doctor has already cleared the same conflict during the prescribing phase of the process. The notification to the Doctor may be provided via the Doctors' database(s) (Block 571) and/or via any other communication links.

Once any conflicts have been cleared by the Doctor, the process flow continues with the Pharmacist confirming the dosage. Third party databases (Block 555) may be utilized (manually or automatically) to confirm the dosage. It is to be appreciated that while the preferred embodiment utilizes a conflict check at both the time of prescribing by the Doctor and the time of dispensing by the Pharmacist, that the process flow may be configured such that neither and/or both conflicts checks are accomplished.

Once the dosage has been confirmed (Block 572), the Pharmacist is now ready to verify the Device operates correctly (Block 573). The Pharmacists may enter into the Device a custom treatment regimen and/or therapy to be provided to the patient (Block 574). The treatment regimen, when it includes a medication, may also be entered into the Device. The Device may then be provided to the patient (Block 576) or returned to the patient (when the Device was previously issued to the patient).

Upon providing the Device to the patient, the Pharmacist desirably may issue a notification to the Doctor that the prescribed medication has been provided to the patient (Block 578). Similarly, an entry may be automatically or manually made into the Pharmacist's database of the medication and/or treatment regimen prescribed and dispensed to the patient (Block 580).

At this point, the prescribing and dispensing of a medication and/or a treatment regimen to the patient is completed. The process may then continue with another patient or terminate (Blocks 582, 584 and 586).

As mentioned previously, the patient's Device 206 (as shown in FIG. 2) is another component of various system embodiments of the present invention. As discussed previously, the Device may utilize a microprocessor or microcontroller to control the notification features and various other functions of the Device. More specifically, the microprocessor may utilize code processes which are stored in the memory storage device 406 (FIG. 4). These several coded processes allow the Device to receive information for up to eight (8) different prescriptions from a host connected to a docking station or other interface device. In various other embodiments, more than eight prescriptions or treatment regimens may also be received. Further, the docking station is typically located at a Pharmacist's office and/or a Doctor's office.

These and/or other coded processes control the various functions of the Device and may utilize information downloaded from the Platform to provide the desired instruction to the patient. The downloaded information may include treatment schedules, drug prescription and dosage information, general messages regarding Pharmacist and/or Doctor contact information, service notification information, Device related status information, and/or other information. These coded processes preferably can also return information pertaining to the patient's compliance with a treatment regimen and/or Device status information.

When the Device is initialized, for example, after having received a new treatment regimen from a Pharmacist, the various registers, counters, I/O controllers, speech synthesizer, and other components are configured. When these and other components of the Device are configured, the configuration information may be routed, as necessary, to the main operating system of the Device (i.e., the main control loop).

In at least one embodiment, the main control loop may be configured to perform a series of actions that evaluate the condition of the Device's various components, schedules, and interfaces, for example, the push button. The main control loop may also direct the performance of various sub-services including, but not limited to, evaluating link wake-up and power mode status, reading and qualifying a current time, evaluating the status of the various buttons provided on the Device (i.e., whether a patient has depressed the button), call finding and active messaging routines, and performing various other status and maintenance tasks.

More specifically, the main control loop may control the sub-service responsible for establishing, maintaining, and monitoring those communications links necessary to transmit information between the Device and the Platform. These processes may include reading and interpreting command requests, sequencing multi-byte message texts, and providing schedule changes to the Device. Such information may be directed, by a sub-service, to appropriate locations in the memory storage device. Further, a sub-service may control the passing of information between the Device and the time keeping chip and between the time keeping chip and the docking station (for example, when a clock/timing synchronization routine is being accomplished).

The main control loop may also facilitate the passing of prescription and/or treatment regimen schedules to the Device over the communications link provided between a pharmacy's Platform and the Device. The prescription schedule information may be provided in a seven day, twenty-four hour format, which generally results in twenty-one bytes of schedule data per each prescribed treatment regiment. However, other formats may also be utilized by the Device. The Device may also be configured to save schedule information, for example, in fixed memory locations which may be pre-allocated in the memory storage device 406. In the preferred embodiment, each prescription schedule is allocated thirty-two bytes of memory. However, larger prescription schedules may be provided when larger memory storage devices are utilized.

Additionally, the main control loop may utilize an events scheduler sub-service to periodically take readings from the internal clock and evaluate whether a treatment regimen event time has arisen, as indicated in a treatment index. More specifically, upon the changing of each hour of a day (or another designated time interval of longer or shorter duration), the events scheduler may be configured to save any unopened prescription status information, format and then compare the current hour and day index to each of the active prescription schedules loaded in the Device, and determine whether an event time has arisen. Further, the events scheduler suitably flags, in the memory storage device, any currently due treatment regimens and returns operations to the main control loop.

Another sub-service process which may be provided in conjunction with the main control loop is the memory storage read/write service. For at least one embodiment, the memory storage device provides 32K by 8 bytes of non-volatile memory which may be accessed over a common two wire serial protocol. The memory storage device read/write service enables a user of a Device (for example, a Pharmacist or a Doctor using a the Platform connected to a docking station) to read and or write specific data to the various data storage locations provided by the memory storage device. In this manner, the user of the Device can access and/or provide specific information pertaining to the patient's compliance with the treatment regimen, treatment regimen instructions, the operation of the Device, and other information.

Another sub-service which may be provided by the main control loop is the momentary button process service. This sub-service provides button related interrupt event status and messages to a patient based upon the depressing and/or momentary holding of the button. More specifically, this service may utilize coded sequences to call a message scheduler that may be configured to maintain sequences of treatment regimen instructions, Device status messages, and other information. Further, this service may provide various button condition indicators including, but not limited to, determining when a double momentary depressing of the button occurs, whether the button has been depressed for a specific time interval, and other button functions as discussed further herein. The operation of the button processes is described in greater detail with reference to FIGS. 7, 10 and 11.

Another sub-service provided by the main control loop is the synthesizer scheduler service. The synthesizer scheduler service stores treatment regimen instructions in the memory storage devices and utilizes an indexing system based upon a first byte of an instruction string message to assign a start location in the memory storage device of the instruction message. Utilizing this indexing scheme, variable length treatment regimen instruction messages may be utilized without wasting storage space in the memory storage device. Such instructions may be specifically tailored to a patient and/or pre-canned instructions obtained, for example, from a third party database.

When the time arises for an instruction message to be communicated to the patient, the main control loop may be configured to identify the location of the desired instruction message by accessing the previously established index. Thus, each message that is to be presented to the patient by the Device to the patient may be saved in the memory storage device and the first byte may be indexed. By utilizing this format of message pointers and variable link messages, the Device may be configured with a fixed linked memory storage Device of 96 bytes. This configuration allows up to 43 messages for both the general and each prescription specific message to be stored and accessed by the Device.

Figure 7:
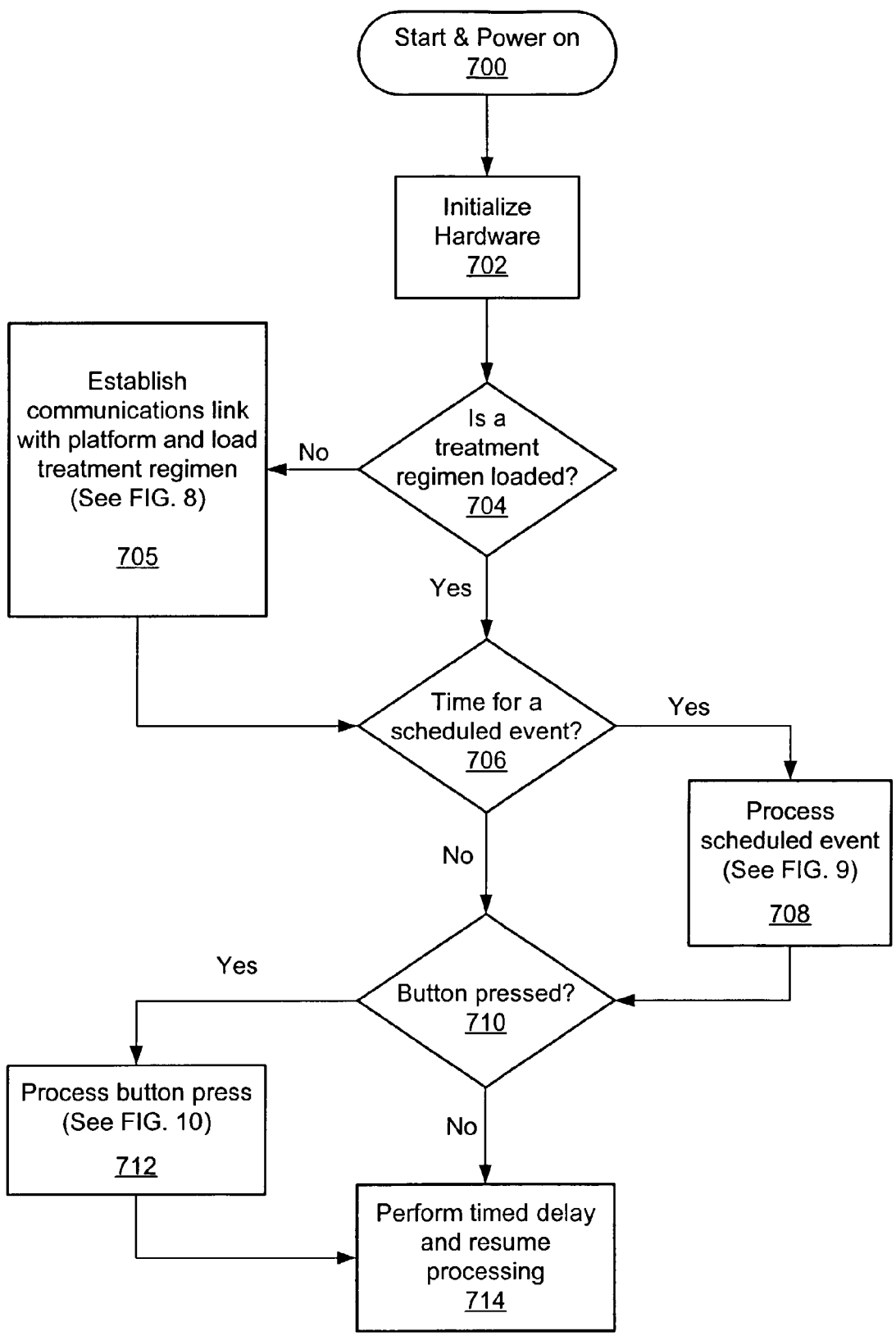
FIG. 7 is a flow chart illustrating the process flow by which the Device operates in its main control loop for at least one embodiment of the present invention.

Referring now to FIG. 7, one embodiment of the process flow of the main control loop is illustrated. As shown, the process flow begins when a start and/or power on sequence occurs (Block 700). At this point, the main control loop initializes the hardware, as previously discussed, including the interface ports, smart cards interface portal, buttons, visual displays, cap sensors, cap solenoids, speakers, clocks, vibrators, storage devices and speech synthesizer, as necessary (Block 702). The process then determines whether a treatment regimen has been loaded into the memory storage device (Block 704).

If a treatment regimen has not been loaded, the Device establishes a communications link with a Platform provided by either a Pharmacist or a Doctor and loads a treatment regimen into the Device (Block 705), once a treatment regimen is available for programming into the Device. One embodiment of the process by which the Device establishes a communications link and loads a treatment regimen is further described with reference to FIG. 8.

Figure 8:
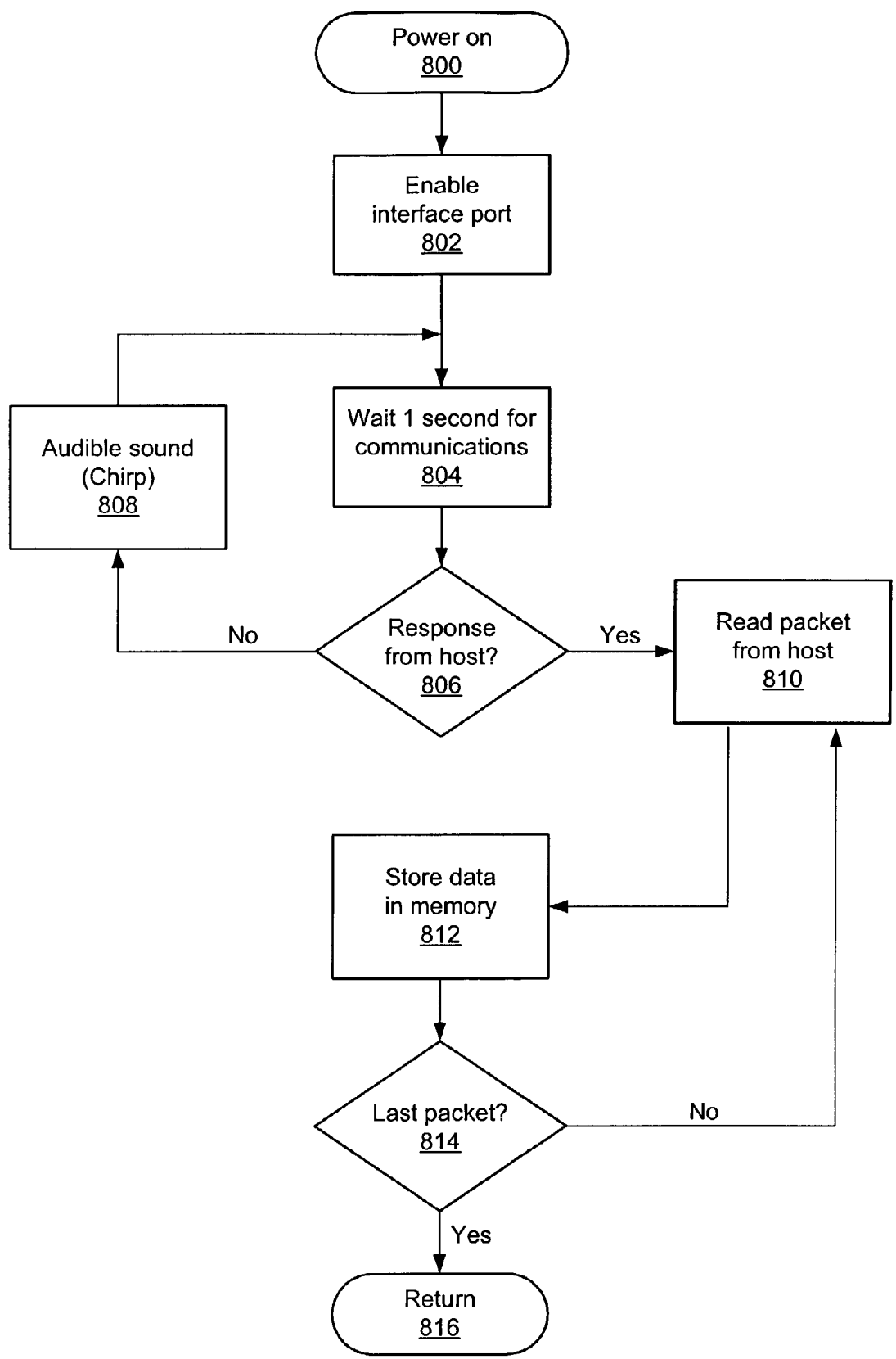
FIG. 8 is a flow chart illustrating the process flow by which the Device loads a treatment regimen from the Platform into the Device for at least one embodiment of the present invention.

As shown in FIG. 8, one embodiment of the process by which the Device loads a treatment regimen begins with a power on event (Block 800). At this point, the Device enables/activates the interface port (for example, an infrared port, Block 802) and/or the smart card reader (when provided). After enabling the interface port, the Device then waits one second for the communications link between the Platform and the Device to be established (Block 804). As discussed previously, the Platform may utilize a docking station to interface with the Device. If a response from the Platform (i.e., the host), does not occur within the pre-determined time interval, preferably one second, an audible alarm is sounded by the Device (as shown in Blocks 806 and 808).

When a response is received from the Platform, the Device reads a data packet provided by the Platform, i.e. the host, (Block 810). This data packet (which may include a treatment regimen instruction) is suitably stored in the memory storage device contained in the Device (Block 812). After receiving a full data packet, the Device determines whether the last packet has been received (Block 814). If the last packet has not been received, the Device repeats the reading of the data packets from the host and the storing of the data packets in the memory storage device until the last data packet has been received and stored (Blocks 810 and 812). At this point, the Device returns to the main control loop as shown (Block 816) in FIG. 7 at Block 706.

After the Device has been loaded with the treatment regimen, the main control loop continues with issuing a query as to whether a scheduled event, as defined by the treatment regimen (or as defined by the internal maintenance procedures associated with the Device) has occurred (Block 706). When a processed scheduled event time occurs, the Device suitably processes the event utilizing the process shown in FIG. 9 (Block 708).

Figure 9:
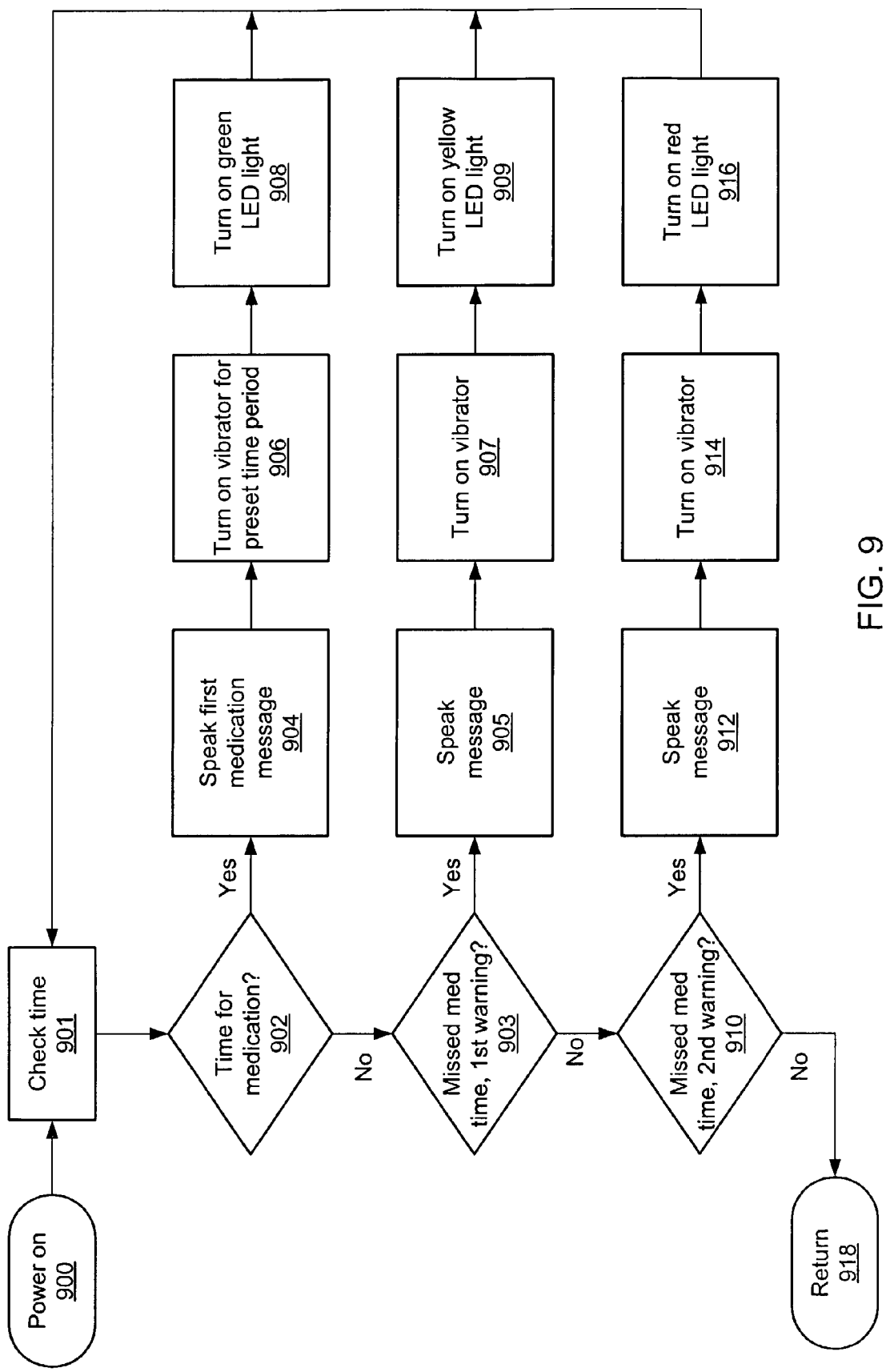
FIG. 9 is a flow chart illustrating the process flow by which the Device processes a scheduled treatment regimen event for at least one embodiment of the present invention.

As shown in FIG. 9, upon receiving a power on or other sequence for the Device to process a scheduled event (Block 900), the processing checks the current time (Block 901) and then determines whether a scheduled event, such as a time for taking a medication, has arisen (Block 902). When a time for taking a medication has arisen, the scheduled event processing routine proceeds with speaking or otherwise suitably providing the first medication and/or treatment regimen message to the patient (Block 904). When configured, the processing may also turn on the vibrator for a predetermined time period (preferably two seconds) (Block 906) and may activate the yellow LED light (Block 908), and/or any other functions specified during the prescribing of the treatment regimen.

When the patient does not respond to the message, vibration and/or green light (i.e., the patient does not access a medication from the Device or otherwise acknowledges the message) within the predefined time limit, the process scheduled event routine continues with issuing a first warning (Block 903). -The process then provides a message to the patient (which may include all or part of the previous message in addition to other instructions) (Block 905). The process may also reactivate the vibrator (Block 907) and/or the yellow LED light (Block 909).

Similarly, when the patient does not respond to the first warning within a predefined time limit, the process scheduled event routine continues with issuing a second warning (Block 910). Similar to the first warning, the second warning includes the functions of speaking or otherwise suitably communicating the first medication message and/or other messages to the patient (Block 912), turning on the vibrator for a predetermined time period (Block 914), and/or turning on a red LED light (Block 916). If the patient has not responded to either of the process scheduled event warnings, the Device returns to the main control loop and determines whether a button has been pressed (Block 918), as shown in Block 710 of FIG. 7.

Figure 10:
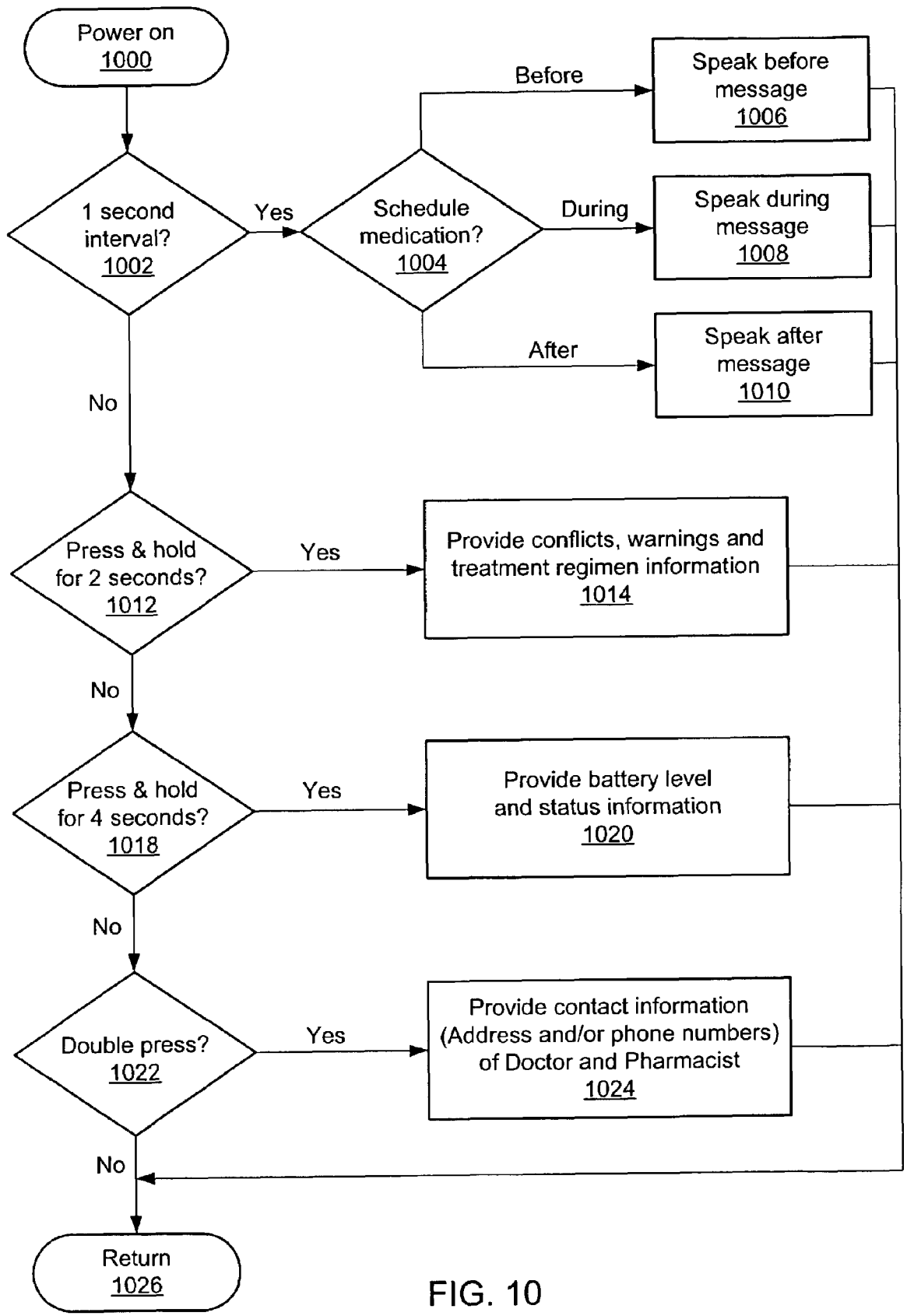
FIG. 10 is a flow chart illustrating the process flow by which the Device processes a button press occurrence for at least one embodiment of the present invention.

When a button has been pressed, the main control loop implements the process button press routine (Block 712). As shown in FIG. 10, the process button press routine begins (Block 1000) with a determination as to whether a button was depressed for a one second interval (Block 1002). When a button is depressed for a one second interval, the Device proceeds with communicating to the patient the medication schedule. Additionally, the Device utilizes the internal clock and the saved medication schedule to determine whether the button was pressed before, during or after a scheduled medication or treatment regime is to be provided (Block 1004). If the button is depressed for one second before a scheduled medication is to be provided, the pre-recorded message provided by the Doctor relating to activities the patient is to perform prior to his scheduled medication time is preferably communicated by the Device to the patient (Block 1006). Similarly, if the button is pressed for a one second interval during a treatment regimen time, instructions are provided to the patient specifically geared towards the taking and/or administering the treatment regimen (Block 1008). Further, if the button is pressed for a one second interval after a scheduled treatment or medication regimen has been administered, the Device communicates instructions provided by the Doctor for the patient to accomplish after the taking of the treatment regimen (Block 1010).

When the button is depressed and held for a two second interval (Block 1012), for example, in response to a notification that it is time for the patient to administer a medication and/or a treatment regimen, the process button press routine preferably continues with providing conflicts, warning and treatment regimen information (Block 1014).

Further, when the button is pressed and held for a four second interval (Block 1018), the Device provides an indication of the battery power level (Block 1020). The battery level indication may include a text message, LED lights, and when equipped with a visual display, an Icon or similar indicator of the battery power status.

Lastly, when the button is double pressed (Block 1022), the Device communicates contact information, for example, addresses and/or phone numbers of Doctors and/or Pharmacists associated with the prescribed treatment regimen (Block 1024). At this point, the processing returns to the main control loop as shown in FIG. 7. Upon which instance, the main control loop performs a timed delay and resumes processing (Block 714). While one embodiment of the present invention is described above as providing specific functions based upon specific presses of a button or other input signal, it is to be appreciated that the present invention is not limited to any specific input devices, input sequences, button sequences or the like and that the present invention may provide different functions for different embodiments of the present invention and that such different functions may be in response to receiving an input signal via methods other than pressing a button.

Figure 11:
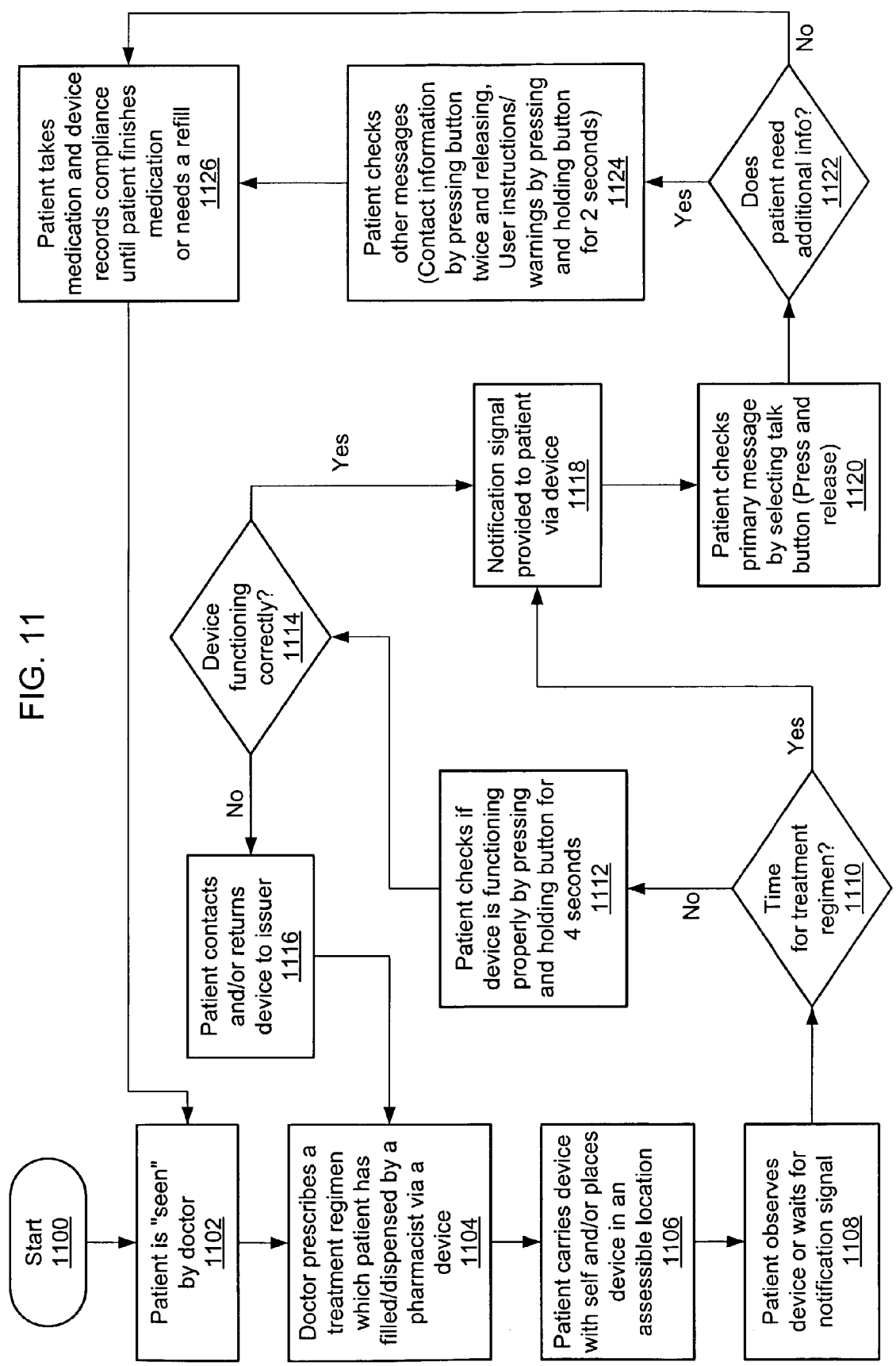
FIG. 11 is a flow chart illustrating the process flow by which a patient interacts with the systems of at least one embodiment of the present invention to receive a treatment regimen.

As shown in FIG. 11, an embodiment of a process by which a patient utilizes the Device to receive a treatment regimen and/or a prescribed medication is depicted. As shown, this process begins when a patient is seen by a Doctor (Block 1102). During the visit by the patient with the Doctor, the Doctor commonly will prescribe a treatment regimen which the patient may have filled and/or dispensed by a Pharmacist utilizing a Device (Block 1104). Thus, at this stage of the process, the Doctor and/or the Pharmacist have utilized any treatment clearance systems necessary and prescribed a treatment regimen which is designed to address the patient's medical condition. This treatment regimen generally includes instructions programmed into the Device, wherein the instructions direct the patient as to how, when, why and where to take a prescribed treatment regimen which may or may not include a prescription medication.

In order to maximize the benefits of utilizing the Device to provide instructions related to a treatment regimen, the patient may carry the Device with them at all times. However, it is to be appreciated that the Device may be configured as a stand-alone unit which is placed in a location accessible to the patient (Block 1106).

When the patient receives and activates a Device, the process may continue with the patient observing the operating status of the Device (including pre-recorded treatment instructions) and/or waiting for a notification signal to occur, before the Device takes any further action (Block 1108). As discussed earlier in relation to the main control loop, the Device may be configured to wait for the time at which a treatment event is scheduled to occur. Until such an event time arises, the Device may query itself as to whether the current time is the designed time for a treatment regimen (Block 1110).

However, the Device does allow the patient to check if the Device is functioning properly by pressing and holding buttons for four seconds, as discussed previously (Block 1112). When the Device is functioning correctly, text messages, audible sound, tactile, and/or visual indicating signals are generated by the Device. If some or all indicating signals are not being correctly generated by the Device, the patient should contact the Pharmacist or Doctor and/or return the Device to the issuer (Blocks 1114 and 1116). Additionally, when the Device is functioning properly, the processing continues with the Device transmitting an appropriate notification signal to the patient (Block 1118).

When the time for a treatment regimen occurs (Block 1110), a notification signal is provided by the Device to the patient (Block 1118). As discussed previously, the notification signal may include a visual signal, for example, a blinking LED light. Further, it is to be appreciated that various other types of identification signals, including vibrations and audible signals, may be utilized by the Device to notify a patient when a time has arisen for a prescribed treatment regimen and/or to notify the patient of the Device status. Upon receipt of the notification signal, the patient may check the primary message by pressing and releasing the "talk" button, i.e., a press and release function (Block 1120). Generally, a simple press and release of the button by the patient will instruct the Device to provide sufficient information for the patient to understand the actions necessary to be taken by the patient in conjunction with the prescribed treatment regimen. However, if the patient does need additional information (Block 1122), the patient may suitably check other messages by pressing and/or holding the button for various time periods, as discussed previously (Block 1124).

Upon receiving all necessary instructions, the patient takes the medication, and the Device records the compliance information in its internal memory storage device. This process flow continues until the patient either finishes the prescribed medication treatment regimen or a refill is needed (Block 1126).

Figure 12A:
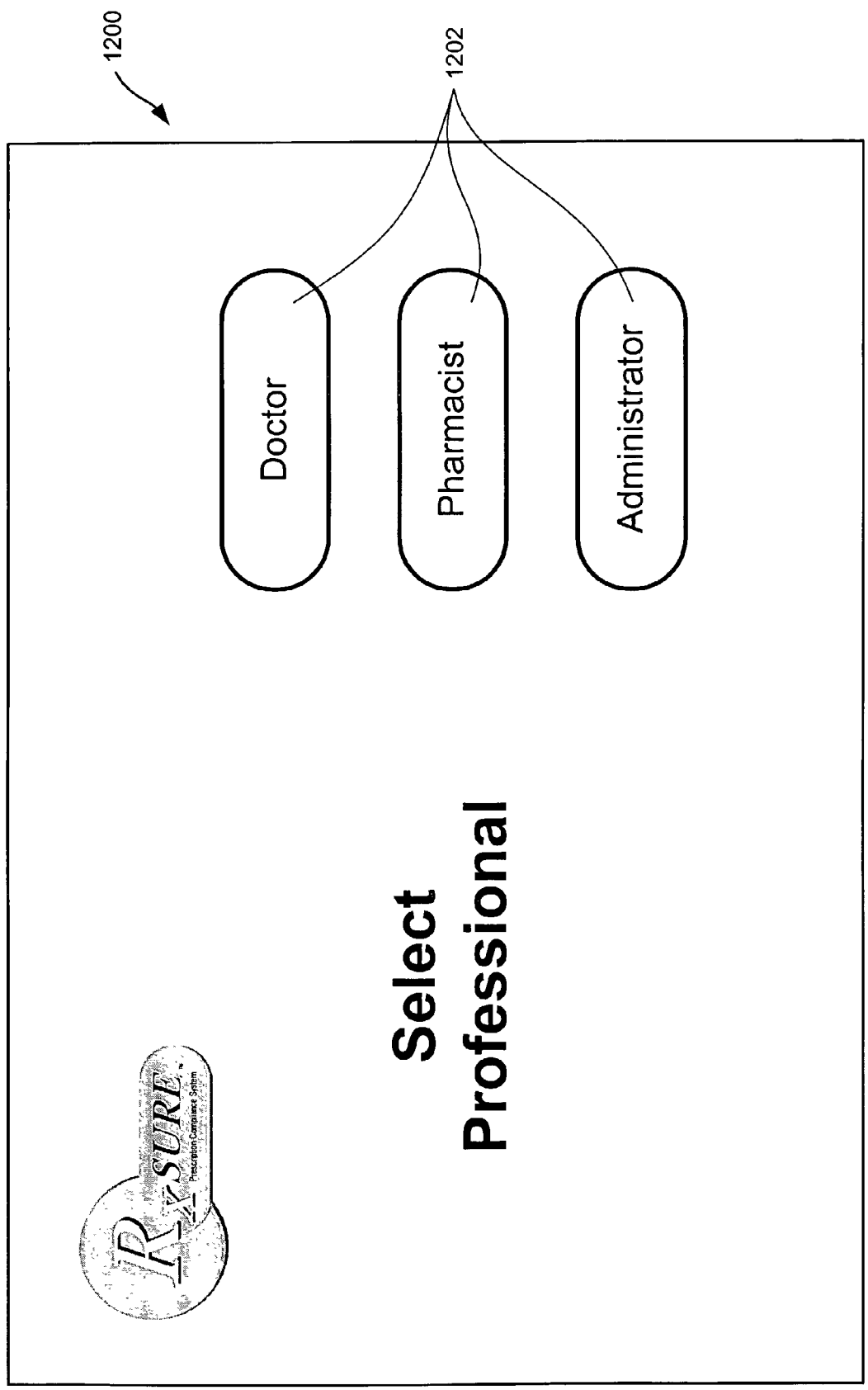
FIG. 12 is a series of screen shots illustrating the interfaces provided by the Platform in another alternate embodiment of the present invention.

Referring now to FIGS. 12A-12X, an exemplary series of screen shots of the Platform are provided which illustrate how a Doctor and/or a Pharmacist may interface with another embodiment of the Platform in order to prescribe a treatment regimen and verify the prescribed treatment is not contraindicated for the patient. As shown, this embodiment of the exemplary series of screen shots are provided by the RxSure™ program. However, other programs, screen shots, and process flows may be utilized without departing from the spirit or scope of the present invention.

Figure 12B:
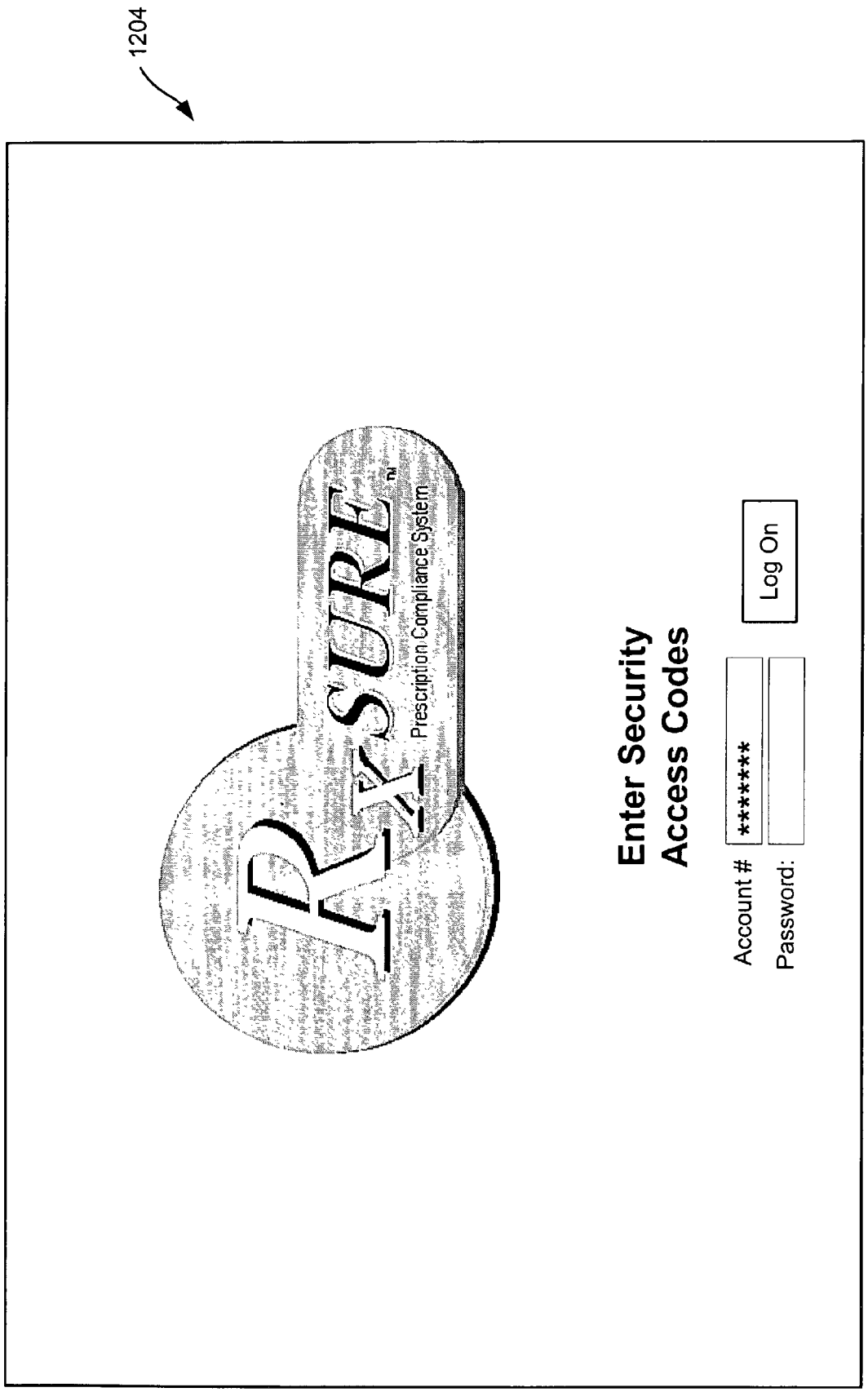

As shown in FIG. 12A, the process, by which a Doctor, a Pharmacist or an Administrator (desiring to add, review, modify, transfer or delete patient records, etc.) interacts with the Platform, begins through an introductory screen 1200 that is used to select a professional's service level 1202 to the specific contents and/or functions of the Platform. Such service levels include access to the content information that relates specifically to the role of the given professional and the tasks they are to perform. One possible means of access to such service levels within Platform is granted based on the successful input, matching and confirmation of pre-programmed security access codes when the Doctor, Pharmacists or Administrator logs onto the Platform as shown on a subsequent access screen 1204 as shown in FIG. 12B.

Security access codes can be an important feature for restricting access to information stored on the Platform and/or functions provided by the Platform, especially in terms of patient confidentiality. Multiple security levels also have a time-saving benefits because different professionals are focused on specific aspects of patient care and generally prefer not spending time searching through all the information stored on the Platform in order to find and address a pertinent issue or a task at hand. In addition, security levels can be used to monitor the actions of a given group to ensure that the professionals are maintaining desires standards of performance. Such means of monitoring includes, but is not limited to, the tracking of specific actions (for example: menu selections, changes in prescription dosages, typed or recorded notations, etc.) made by a Doctor, Pharmacist or Administrator while interacting with the Platform.

Figure 12C:
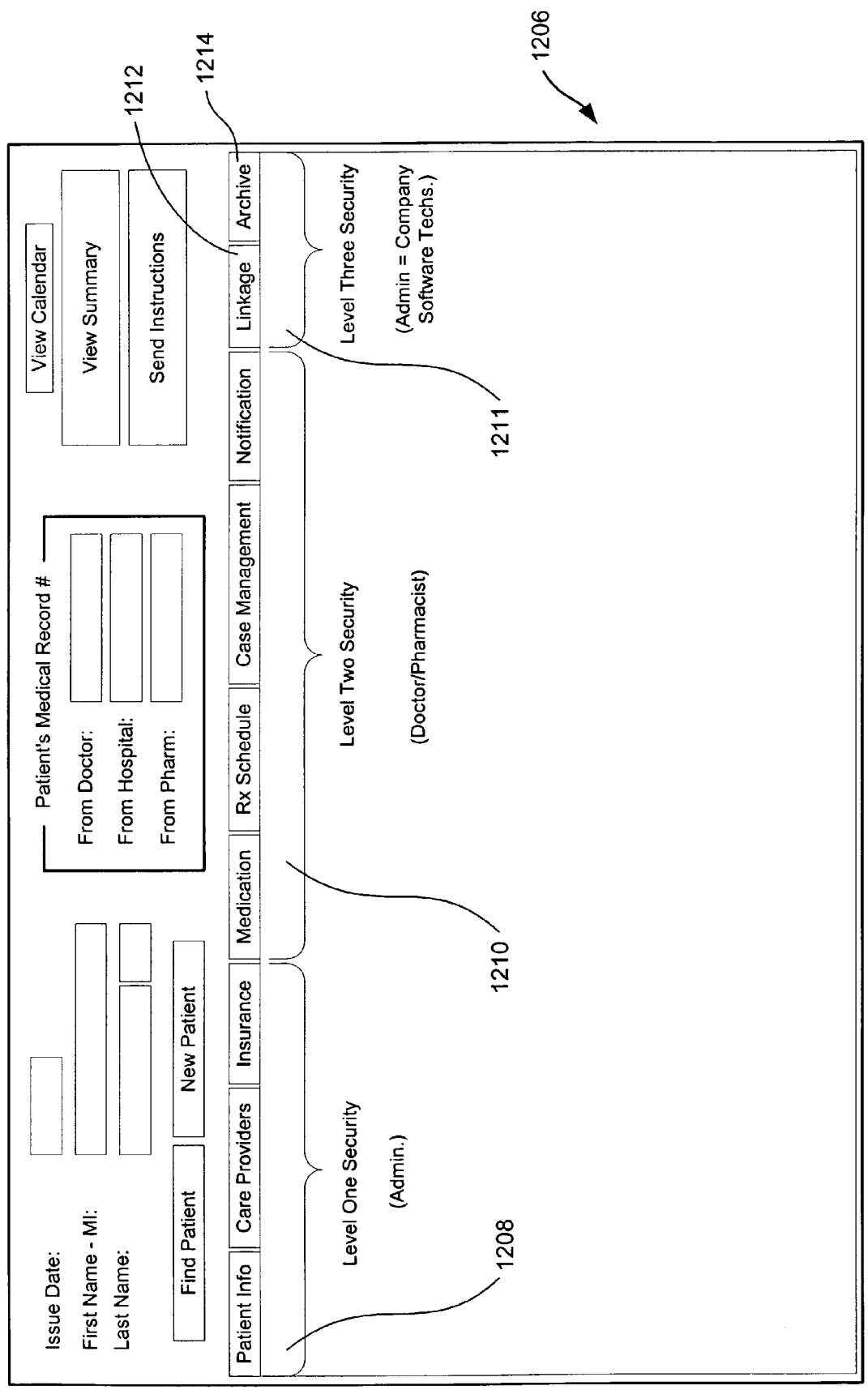

An exemplary set of security access levels, that may be used to limit a Doctor, a Pharmacist or an Administrator's ability to interact with stored information on the Platform, is shown in FIG. 12C. A content tab reference screen 1206 illustrates one such possible grouping of menu screen tabs. More specifically, a level one security grouping 1208 refers to a lower level security ranking that is normally accessed by an Administrator charged with tasks such as retrieving, entering, or updating patient records on the Platform. Such content relates to the general background information on a new or existing patient. A level two security grouping 1210 refers to a higher level security ranking that is normally accessed by a Doctor or Pharmacist charged with tasks such as prescribing, monitoring, or updating patient regimen information stored on the Platform. A security level three grouping 1211 refers to yet an even higher level security ranking that is normally accessed by an Administrator charged with system-related tasks such as programming, monitoring, or updating the operation of the Platform and its content. A further breakdown of this level reveals two possible menu tabs. One such menu tab is a linkage tab 1212 that functions in the same manner as an accounting audit trail, whereby an Administrator can specify what changes have occurred to the Platform's content from a given date as well as track what information is to be captured and stored within the hardware device in a permanent fashion. Another such menu tab is an archive tab 1214 that displays the permanent notation of all content changes to the Platform and/or the hardware device that took place on any given day since one or more corresponding tracking features were activated on the linkage tab 1212. Although screen 1206 only identifies three such security groupings, other levels can be added, combined or removed to suit the specific needs of the users.

Figure 12D:
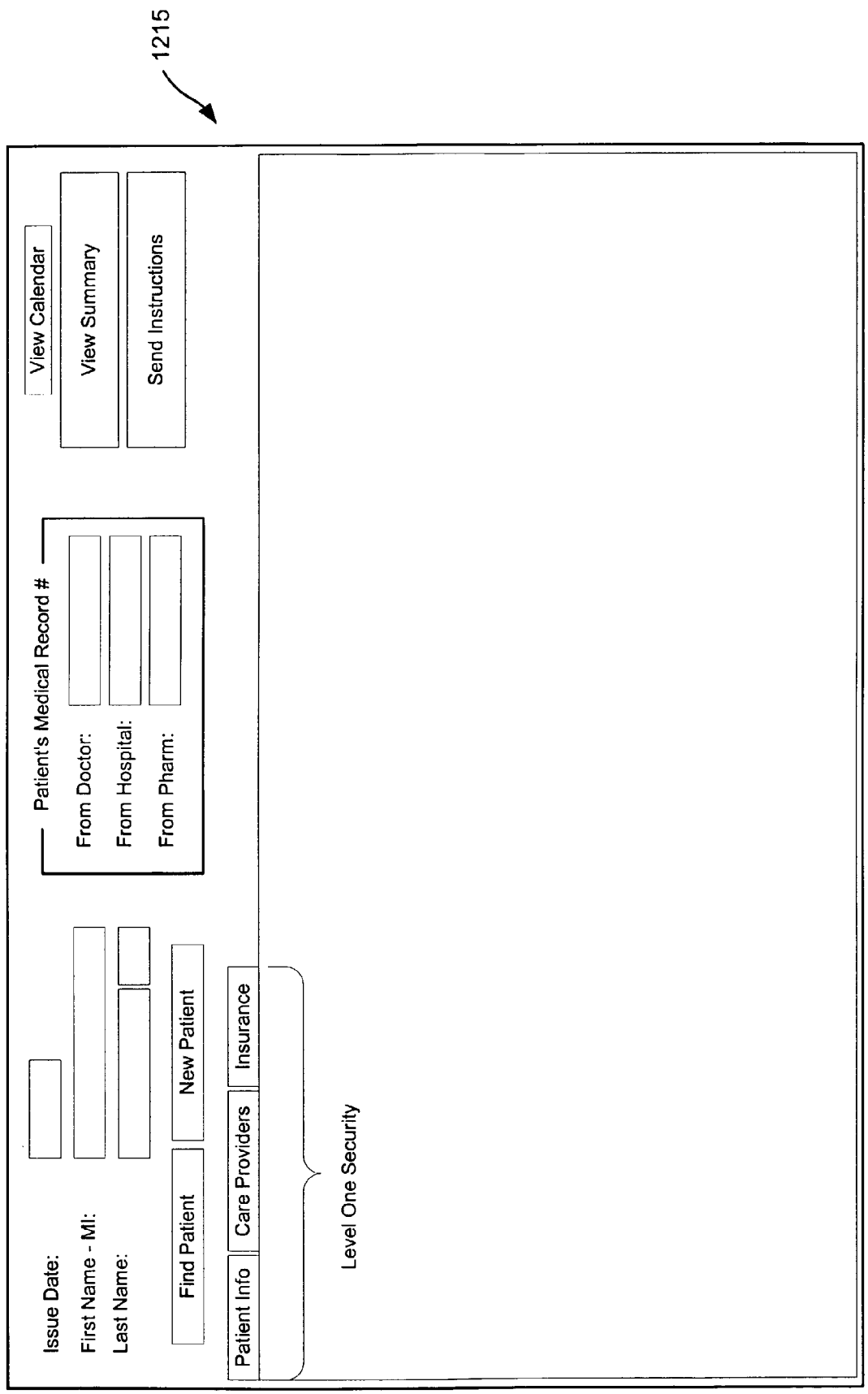

Referring now to FIG. 12D, a content screen 1215 is shown that identifies the menu tabs associated with level one security ranking, and is normally associated with an Administrator who deals with general background information about a given patient. Such tabs include Contact Info, Care Providers and Insurance facts but could include other menu tabs, such as medication, that are entered by the Administrator and provide more detailed information about the patient's past or current list of medications. All other tabs remain hidden from the Administrator based upon the assigned user access level that was entered in the access screen 1204 as shown in FIG. 12B.

Figure 12E:
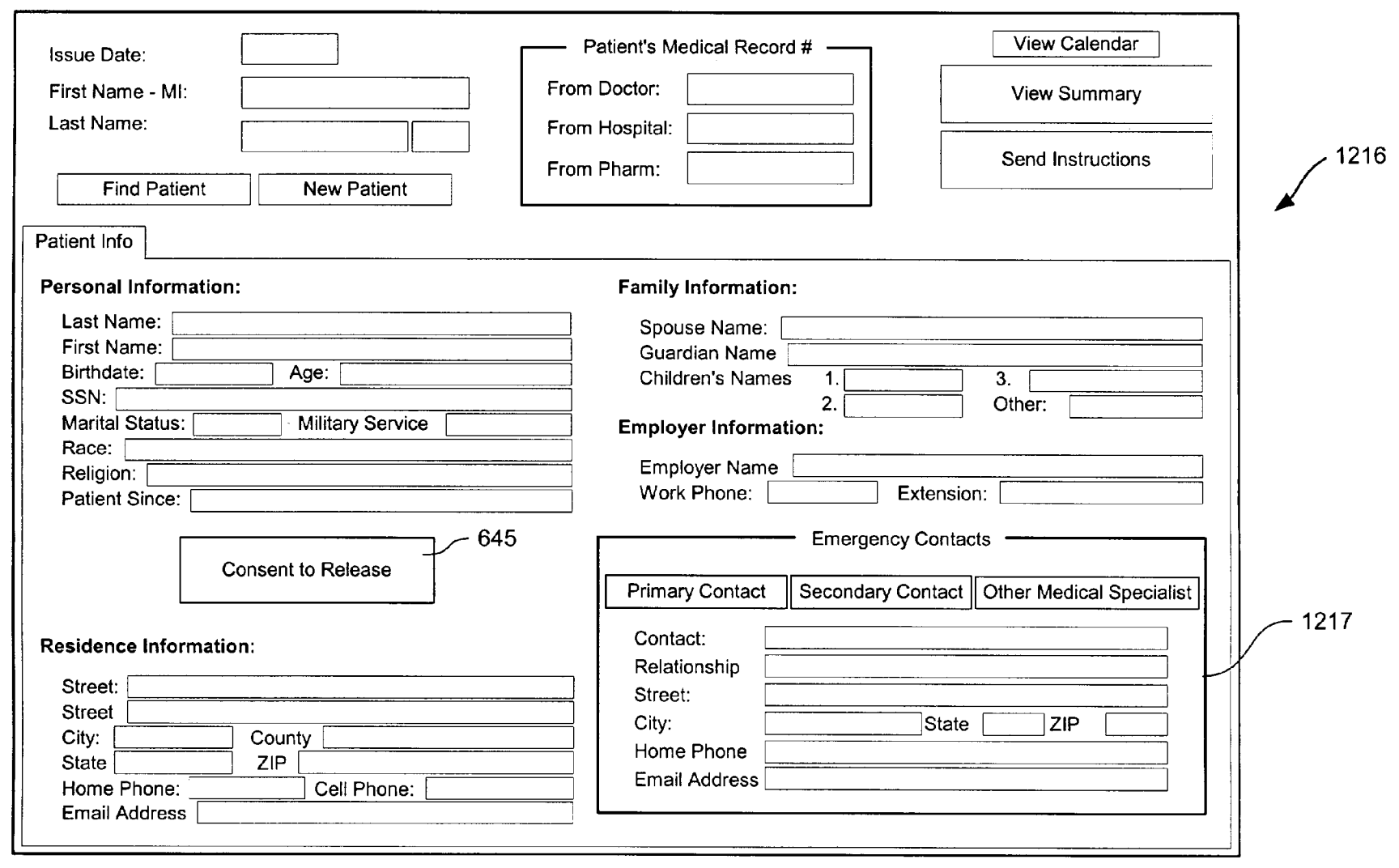

FIG. 12E illustrates an alternative layout of a Patient Info screen 1216 whereby the Consent to Release button 645 has been relocated from the Care Providers tab 644. Such a layout change may prove more intuitive for the user of the Platform who must secure an authorized consent from each patient as part of their required patient information profile. Also, a screen segment 1217 titled Emergency Contacts has been isolated from the other fields and shown with its own set of internal tabs in order to highlight situations where it is beneficial or appropriate to provide multiple contacts and a certain medical specialist for a given patient.

Figure 12F:
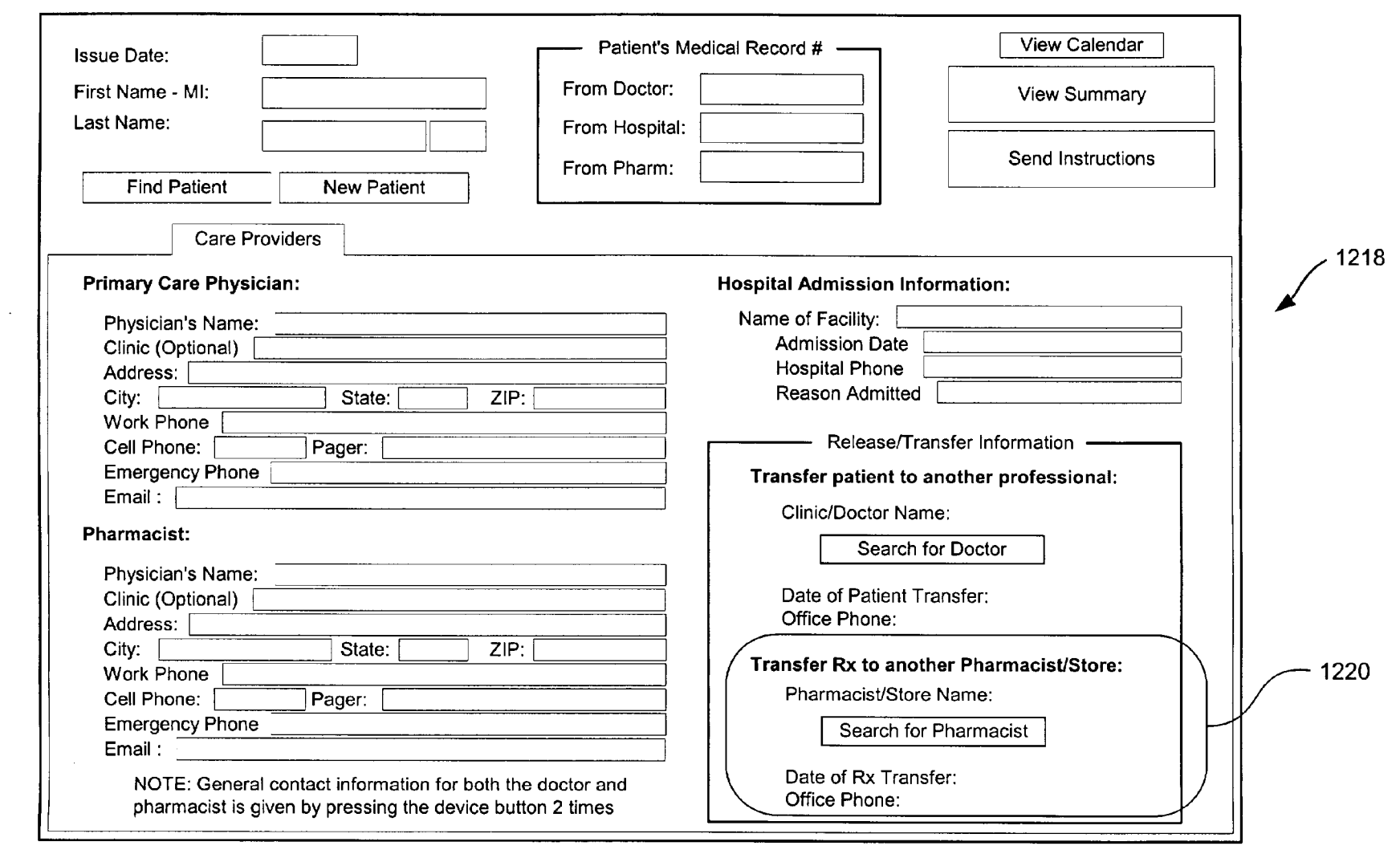

FIG. 12F provides an alternative layout of a Care Providers screen 1218 whereby the release or transfer of information section has been expanded to include a Transfer Rx to another Pharmacist/Store 1220. Such an addition may prove a time savings element whereby a given prescription can be sent electronically through the Platform to a designation location without the need for a telephone call by the Doctor or the patient. As patients visit relatives, vacation, temporarily or permanently relocate, or find more cost-effective sources for their prescription, this feature allows the change to be processed without delays or the need for a new signature by the prescribing physician.

Figure 12G:
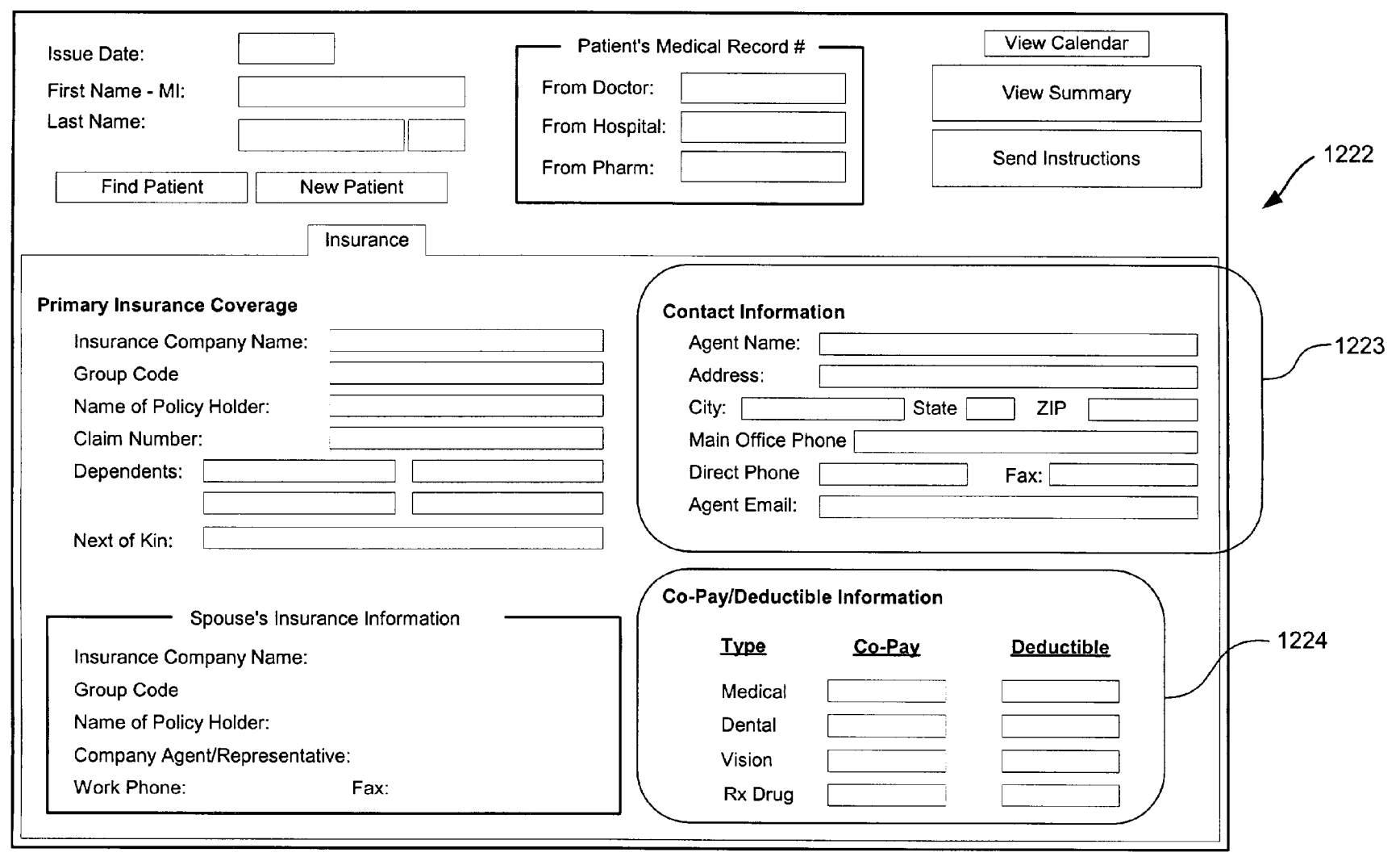

FIG. 12G provides an alternative layout of an Insurance screen 1222 whereby additional information is provided for a more complete profile of the patient. In particular, a Contact Information section 1223 has been broken out from the original Insurance information field 668 (see FIG. 6) to distinguish policy details from the information related to a particular agent. The latter information has the likelihood of change during the life of the coverage. In addition to making it easier for the user of the Platform to find information related to the contact the agent, this alternative layout reflects a separation of data that is likely to change during the life of the particular insurance coverage. Also, a Co-Pay/Deductible section 1224 may include information that is valuable to the Doctor, Pharmacist and/or Administrator who needs an accessible record of co-pay fees that must be collected from the patient at the time of the visit or the amount of the coverage deductible prior to sending out an invoice for services received. A breakdown of the different types of co-payments or deductibles includes, but is not limited to, medical, dental, vision, or prescription drug services or goods.

Figure 12H:
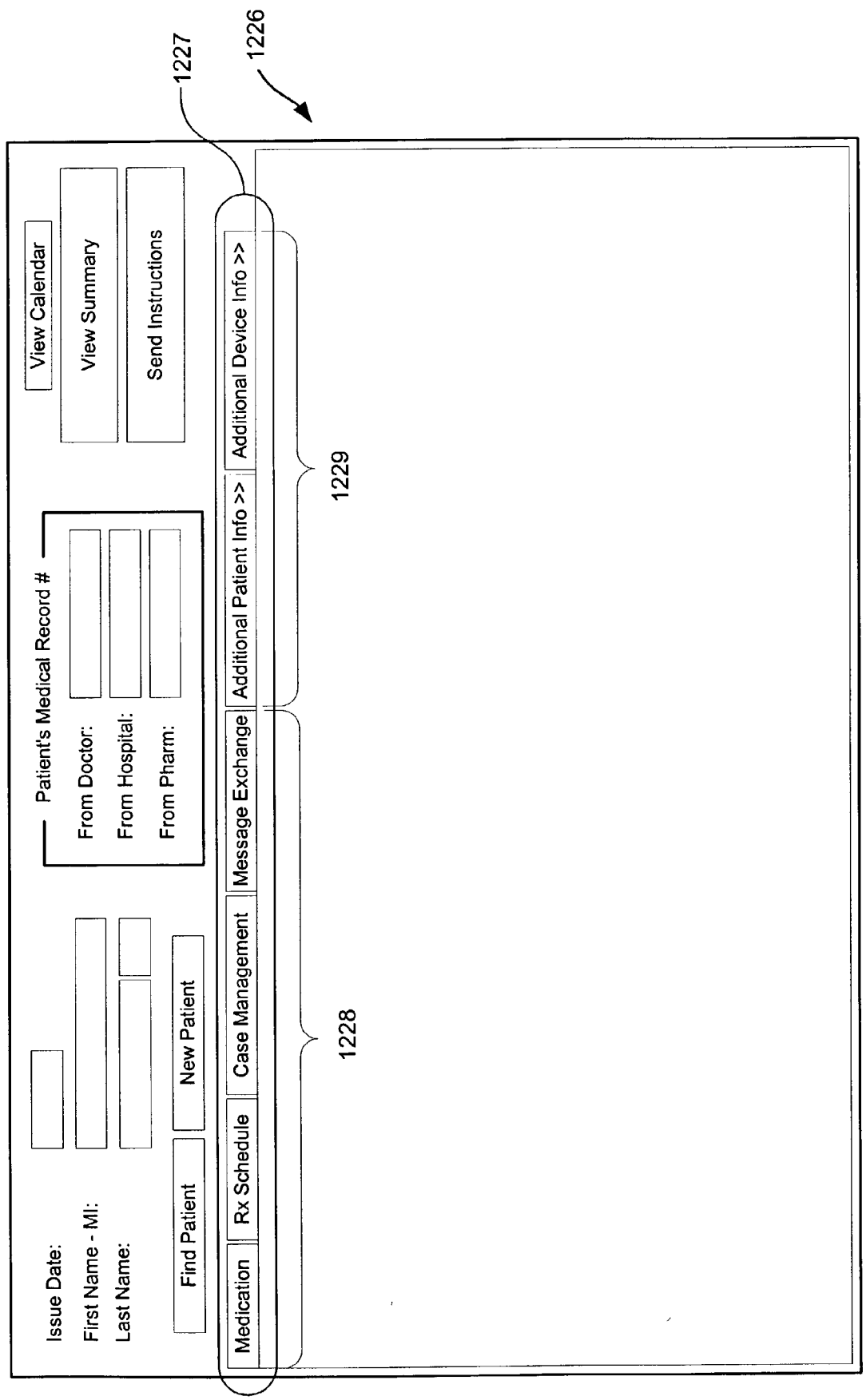

A level two security ranking is normally assigned to Doctors and Pharmacists. As shown in FIG. 12H, such ranking calls for a set of content menu tabs 1227 that are further defined in terms of a tasking function tab 1228 or a forwarding tab 1229. A content screen 1226 is shown that identifies the primary function performed by Doctors and Pharmacists. The tasking function tabs 1228 include, but are not limited to, Medication, Rx Schedules, Case Management, and Message Exchange tabs. The forwarding level tabs 1229 include, but are not limited to, Additional Patient Info and Additional Device Info tabs. More specifically, the forwarding level tabs 1229 have the functional capability to display other content menus, such as the security grouping 1208 for patient background information, that may be of assistance to the Doctor or Pharmacist. All other tabs remain hidden from the Doctor or Pharmacist based upon the assigned user access level that was entered into the screen shown in FIG. 12B.

Figure 12I:
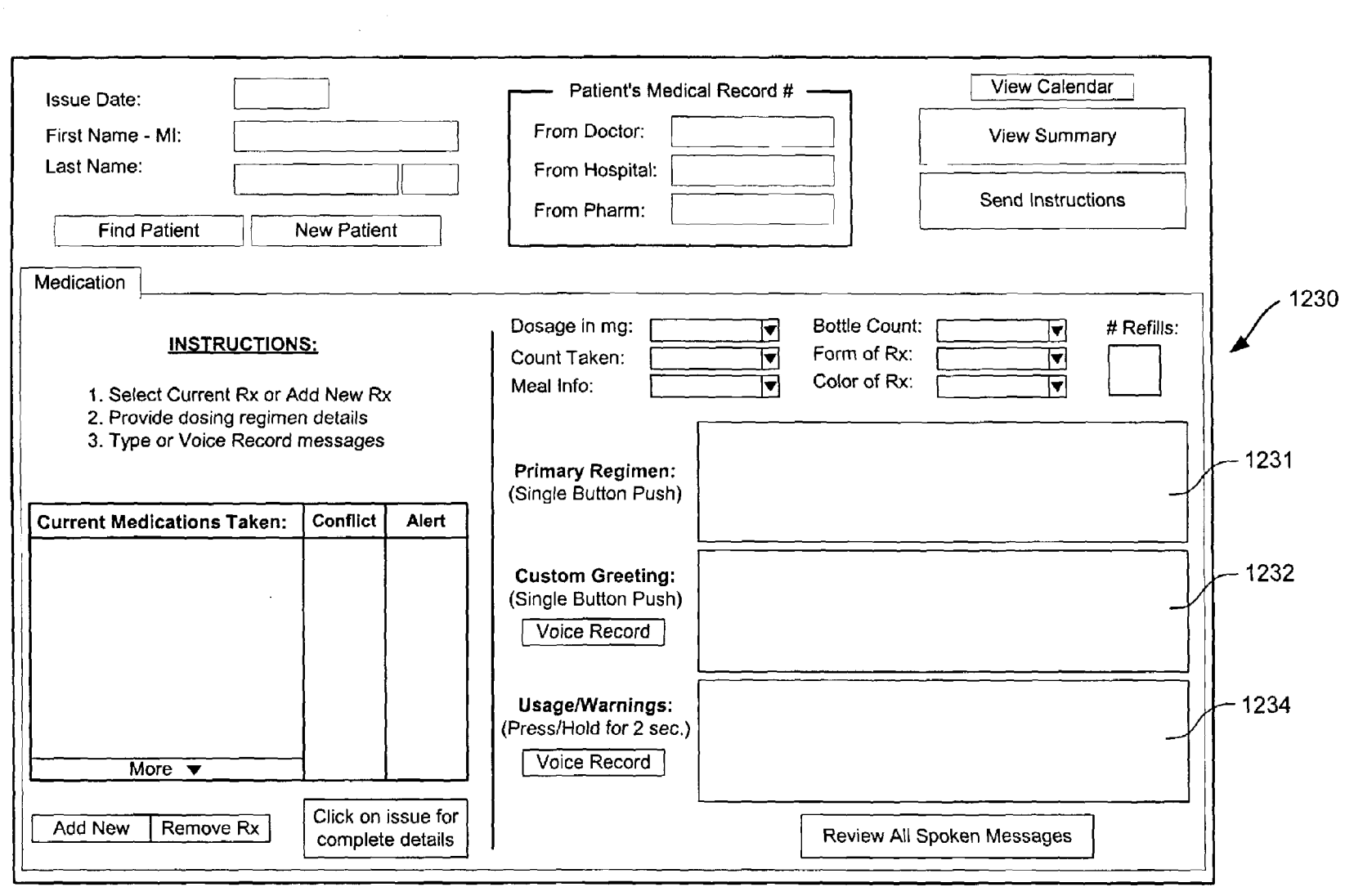

One of the primary screens used by Doctors involves the prescribing of medications. FIG. 12I provides an alternative layout of a Medication screen 1230. This layout provides sufficient space for the Doctor or Pharmacist to enter and review the typed or voice recorded message associated with the current medication to be taken. Such typed or voice recorded messages include a text space for a Primary Regimen 1231, a Custom Greeting 1232, and a Usage/Warning 1234. The Custom Greeting text space 1232 is considered a supplemental message that is attached to and immediately precedes the spoken message content of the Primary Regimen activated by a single push of the Talk button 318 on the hardware device. The Usage/Warning text space 1234 reveals the content of the message that will be spoken by the hardware device when activated by pressing and holding the Talk button 318 on the hardware device for 2 seconds. The purpose of displaying such message content is to provide the Doctor or Pharmacist with the means to quickly review and confirm the spoken instructions delivered by the hardware device in conjunction with the prescribed medication.

Figure 12J:
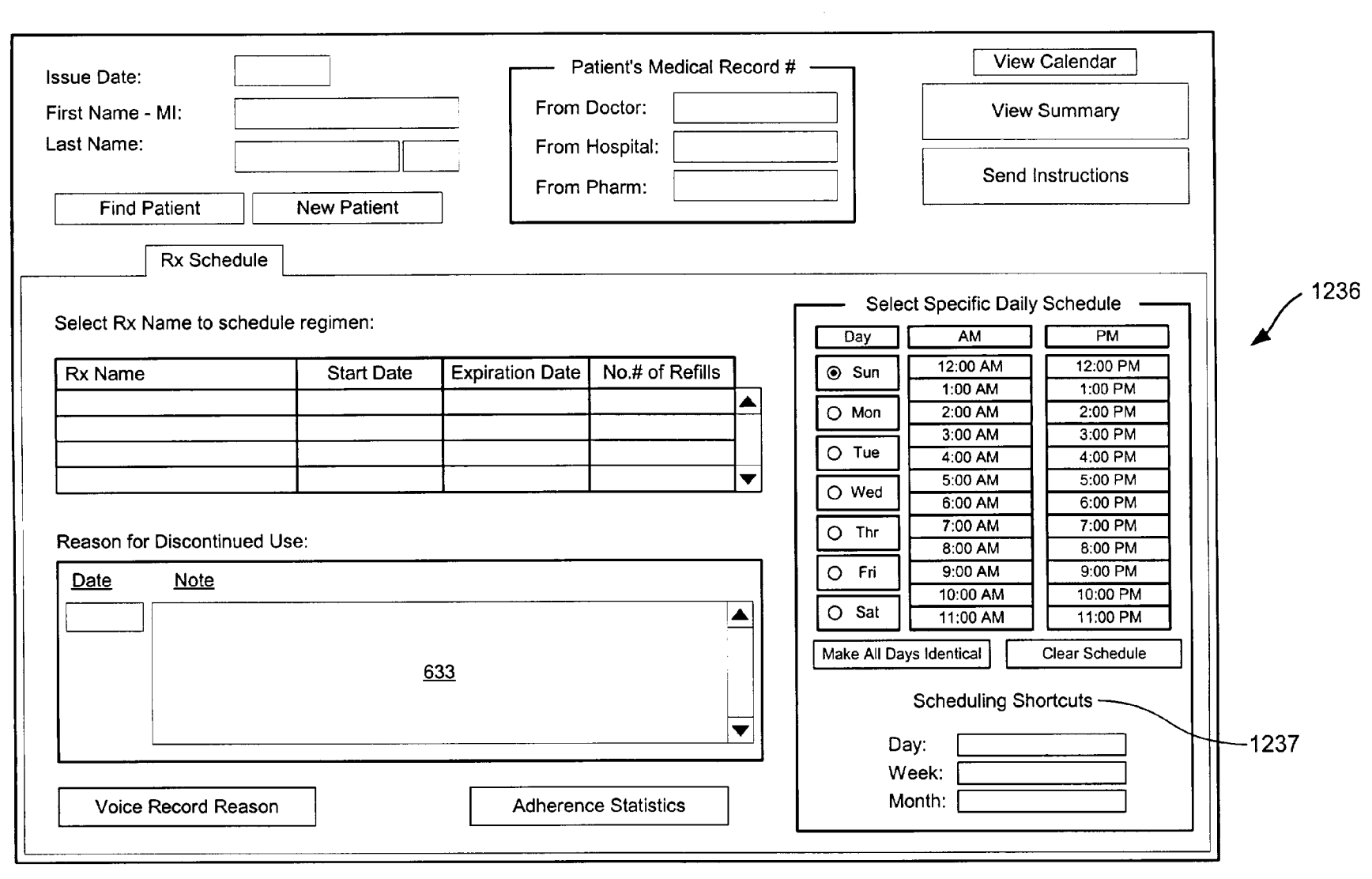

Once the medication has been selected by the Doctor, FIG. 12J provides an alternative layout of an Rx Schedule screen 1236 whereby all content relates specifically to the scheduling of a medication rather than including any dosing-related information such as amount, pill color or form, and meal or special instructions as shown in FIG. 6H. Similarly, the field 633 in which a reason for stopping a medication or treatment regimen has been relocated from the Medication tab 634 in order to emphasize the date and a reason why a particular medication schedule has been discontinued. Another scheduling distinction is created by the use of a Scheduling Shortcuts section 1237 that allows the Doctor to quickly specify the generalized medication regimen using three pull-down menus rather than selecting specific times for each specific day. These pull-down menus are directly linked to the specific schedule based on the Doctor entering a starting location. An example of the use of a generalized schedule is where a Doctor selects "4 times a day" from the day menu, then "every day" beginning "Tuesday" from the week menu, and finally a duration lasting "60 days" from the monthly pull-down menu. Such a shortcut process is further simplified if the "start" and "end" dates are provided when the medication is specified.

Figure 12K:
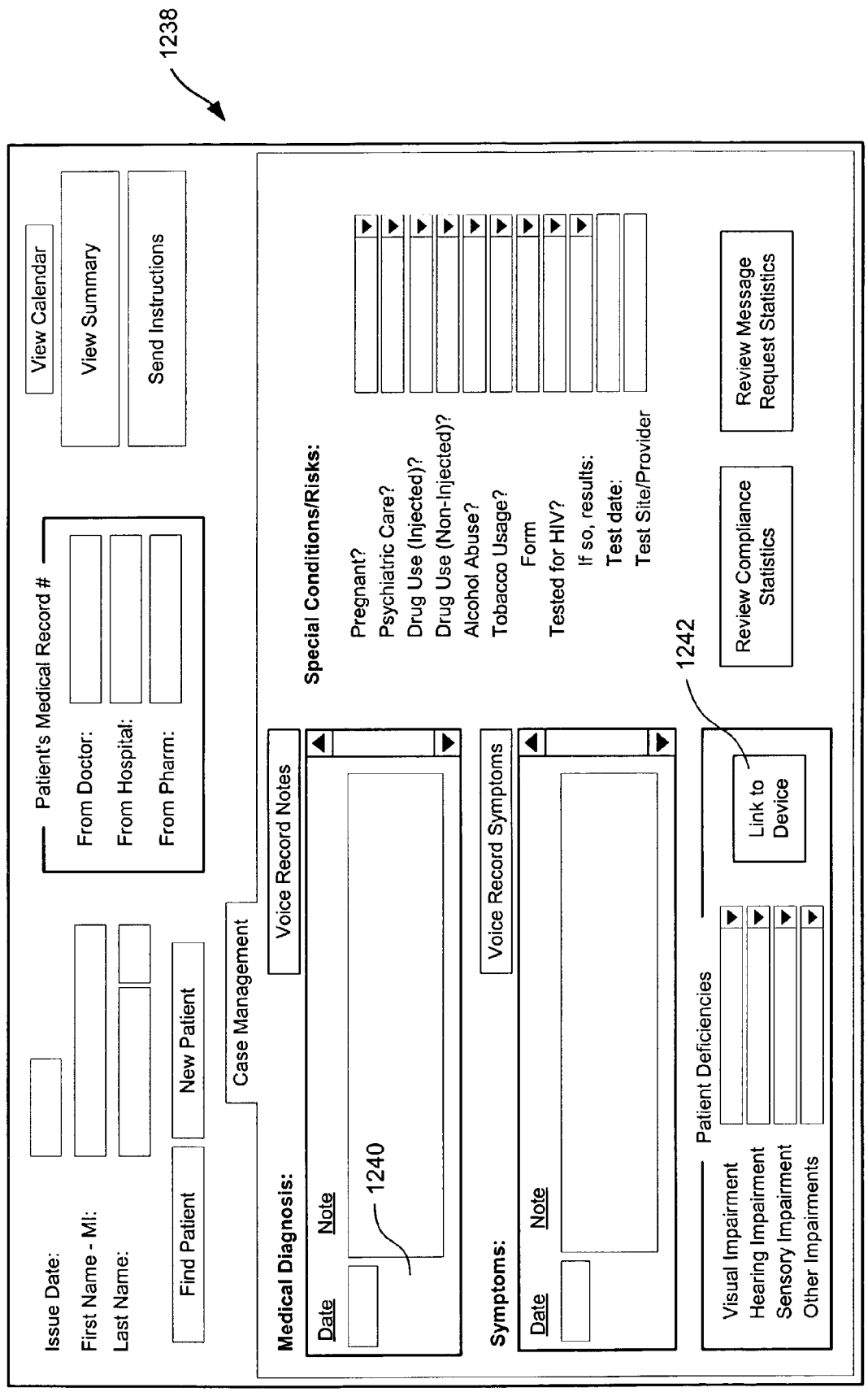

One time saving element for the Doctor relates to the inclusion of a field for pertinent notes about a given patient. FIG. 12K provides an alternative layout of a Case Management screen 1238 that includes a Medical Diagnosis note section 1240. This note section allows the Platform to receive either typed or voice recorded notations and associate them with the entry date. Should Doctors (primary, secondary or referred specialist) or Pharmacists need to review the case of a new or existing patient, all diagnosis details are available in one location and organized by a data stamp. Yet another time saving element is a Link to Device button 1242. This button serves to link patient deficiencies such as hearing or visually impaired with the operations of notification features (i.e., flashing lights, vibrations or audio signals) on the hardware device. In other words, a single menu selection indicating that the patient is blind will turn off the flashing LEDs 310 if the Link to Device button is pressed. Confirmation of a linkage between patient deficiencies and notification signals emitted by the hardware device appears on a Device Control screen 1247 with a Device Alerts section 1248 as shown in FIG. 12M.

Figure 12L:
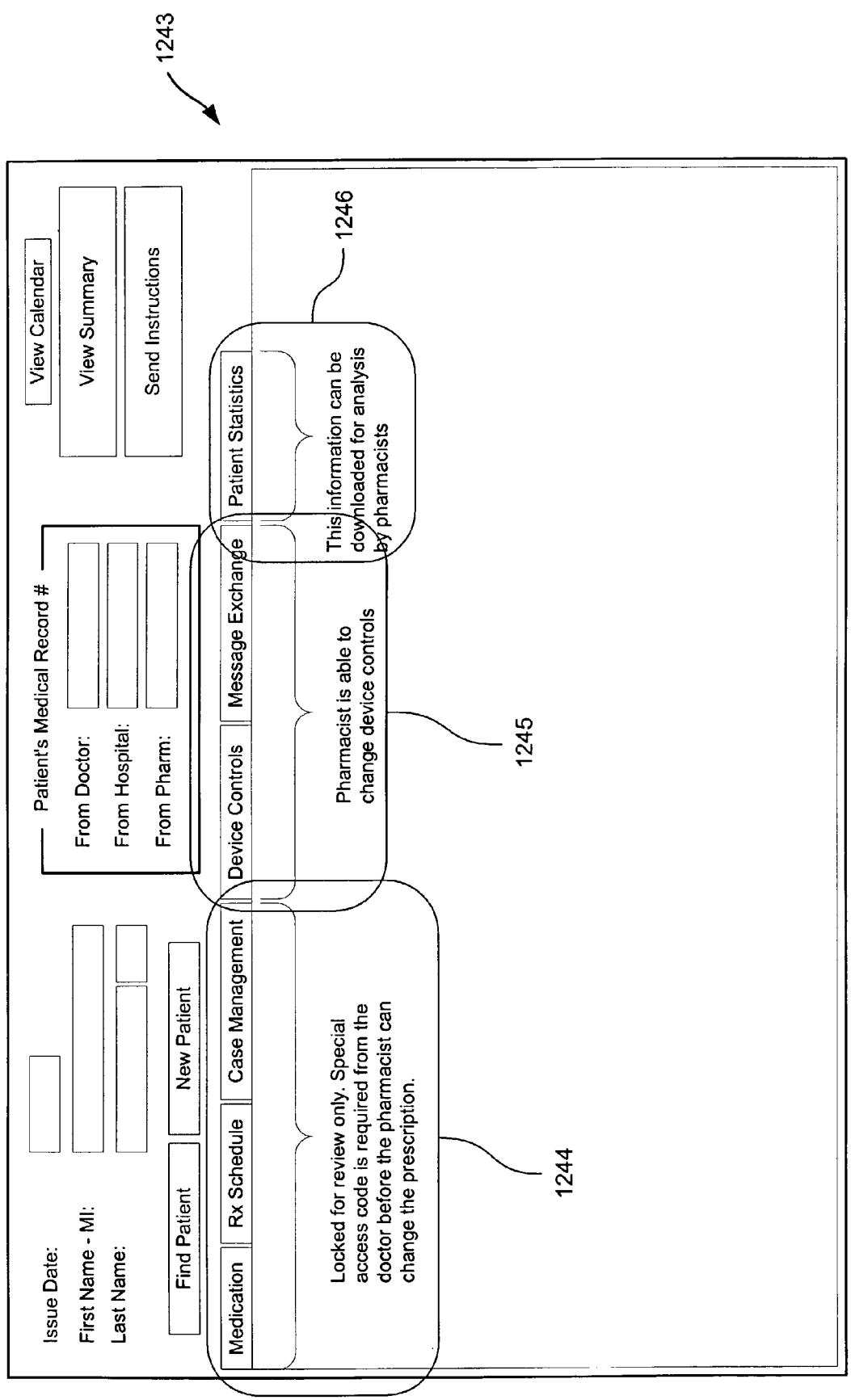

One of the elements associated with this embodiment of the Platform interfaces include, but are not limited to, the ability of the Platform to record and disseminate customized instructions for the patient, the interaction between users on the Platform, and the integration of the Platform with the hardware device. An sample menu screen 1243 illustrating these elements for a Pharmacist is shown in FIG. 12L. In particular, customized instructions from a Doctor can be found in a set of function tabs 1244; interaction between users of the Platform calls for a set of communication tabs 1245 which have been labeled as Message Exchange and Device Controls, and integration of the hardware with the Platform as indicated by a feedback tab 1246, that is also referred to as Patient Statistics. Also, it is important to note that the communication tabs 1245 can include functions such as an electronic mail system or instructions from the Platform that are used to program the hardware device. The feedback tab 1246 may provide statistical information that has been recorded based on actions of the patient (i.e., button presses) and available for downloading from the hardware device to the Platform upon its return for a refill or new prescription instructions.

Recalling FIG. 12M, the content screen 1247 illustrates the features of the Device Controls tab. In general, these features are used to program the hardware device, monitor operations, generate statistics, and allow stored information to be downloaded back to the Platform. A sample set of Default Settings 1249 is shown. These settings can be checked or unchecked to allow the corresponding operation to be performed, recorded and/or printed.

Figure 12N:
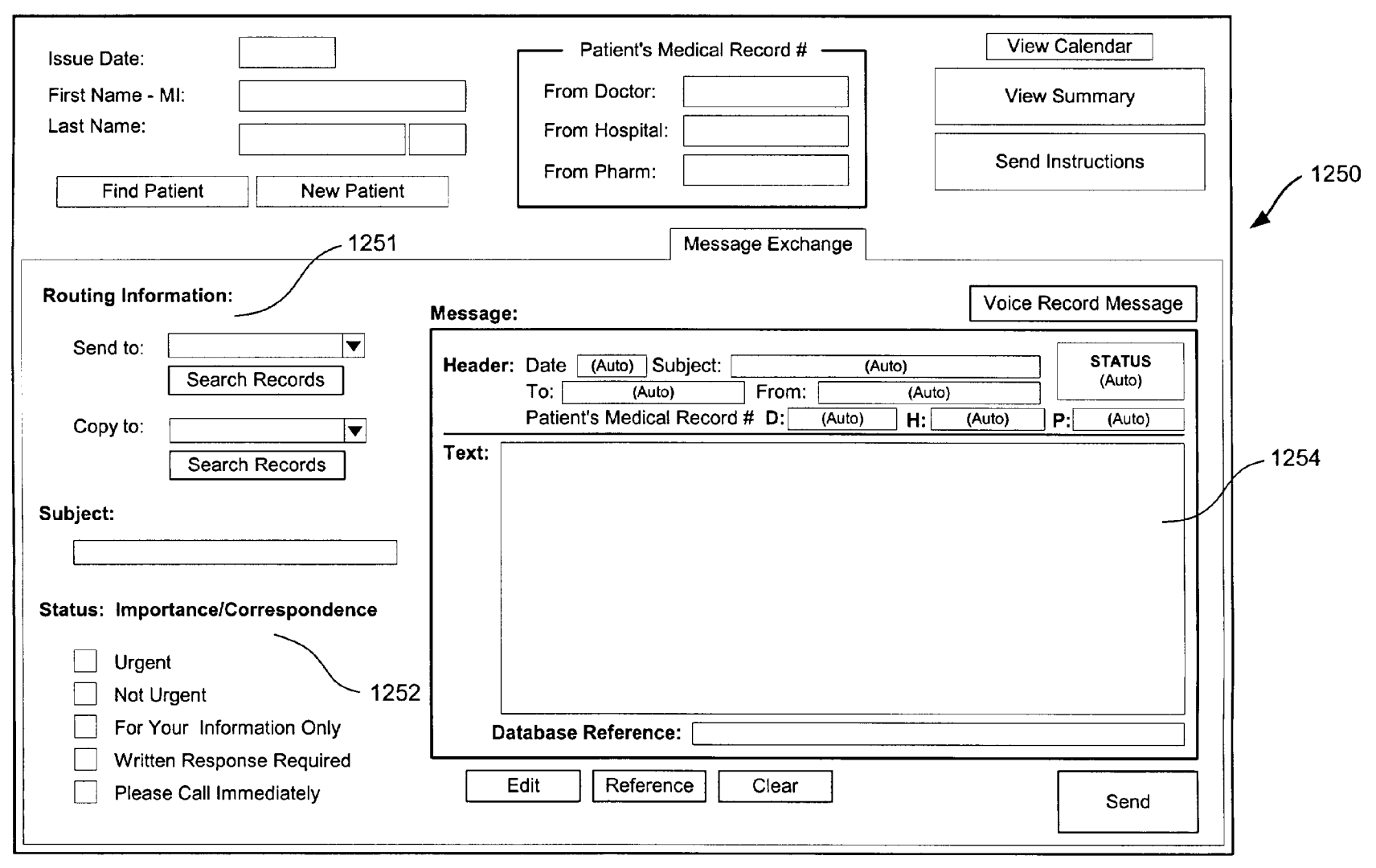

Referring now to FIG. 12N, a content screen 1250 illustrates the important features of an electronic messaging system between the various users of the Platform. Specifically, a user can search, identify and distribute a customized message inserted into the Message field 1254 to a particular receiver(s) using a Routing Information pathway 1251. Such messages can range from, but are not limited to, requests to review a specific alert to notifications of dosage problems to personalized comments about a patient that is being transferred. A Status section 1252 is included to help the receiver classify and/or prioritize the pertinent message received. Such status indicators are attached to the message in order to provide the receiver with a relative level of importance associated with a given message and/or the need for a corresponding action in response to the given message.

Figure 12O:
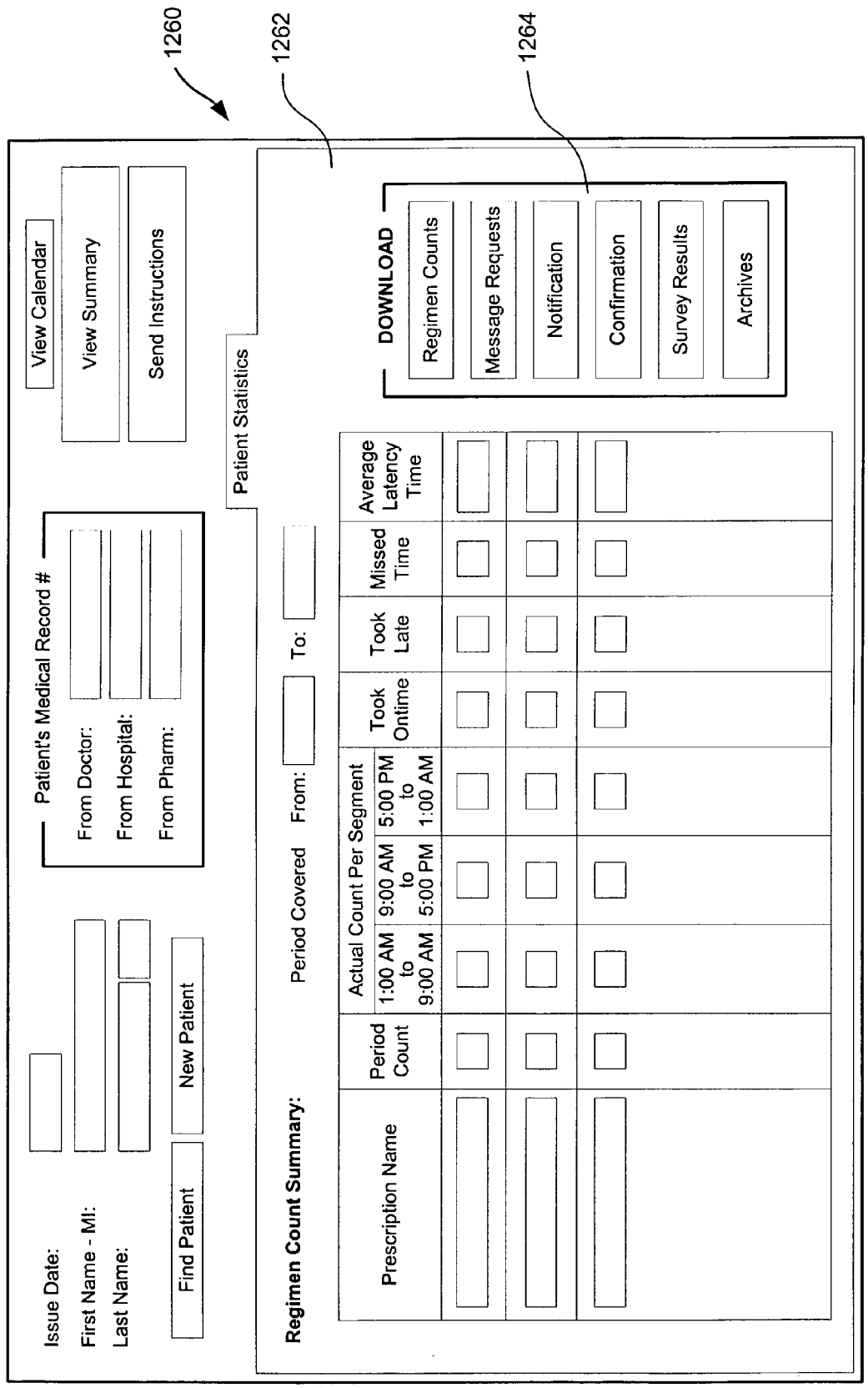

Pharmacists may play a key role in monitoring a patient's compliance to a given regimen as they are charged with dispensing new medication or providing refills of an existing prescription. Referring to a content screen 1260 in FIG. 12O, this monitoring process calls for the use of a series of display formats 1262 viewed on the Patient Statistics tab which are generated by the hardware device in accordance with the patient's actions (i.e., Talk Button presses). In particular, FIG. 12O shows the Regimen Count Summary display which breaks down the time-stamped button presses (i.e., notification of a medication due and confirmation that a medication was taken) into actual counts per segment within a 24-hour period. The contents of such a table may be automatically filled with the statistics that were downloaded from the hardware device to the Platform upon its return from the patient using coded routines, algorithms and standard formulas. Should other statistics be desired, a Download section 1264 uses activation fields to retrieve the corresponding display format that appears on the same Patient Statistics tab. These fields include, but are not limited to, Regimen Counts, Message Requests, Notification, Confirmation, Survey Results, and Archives.

Figure 12P:
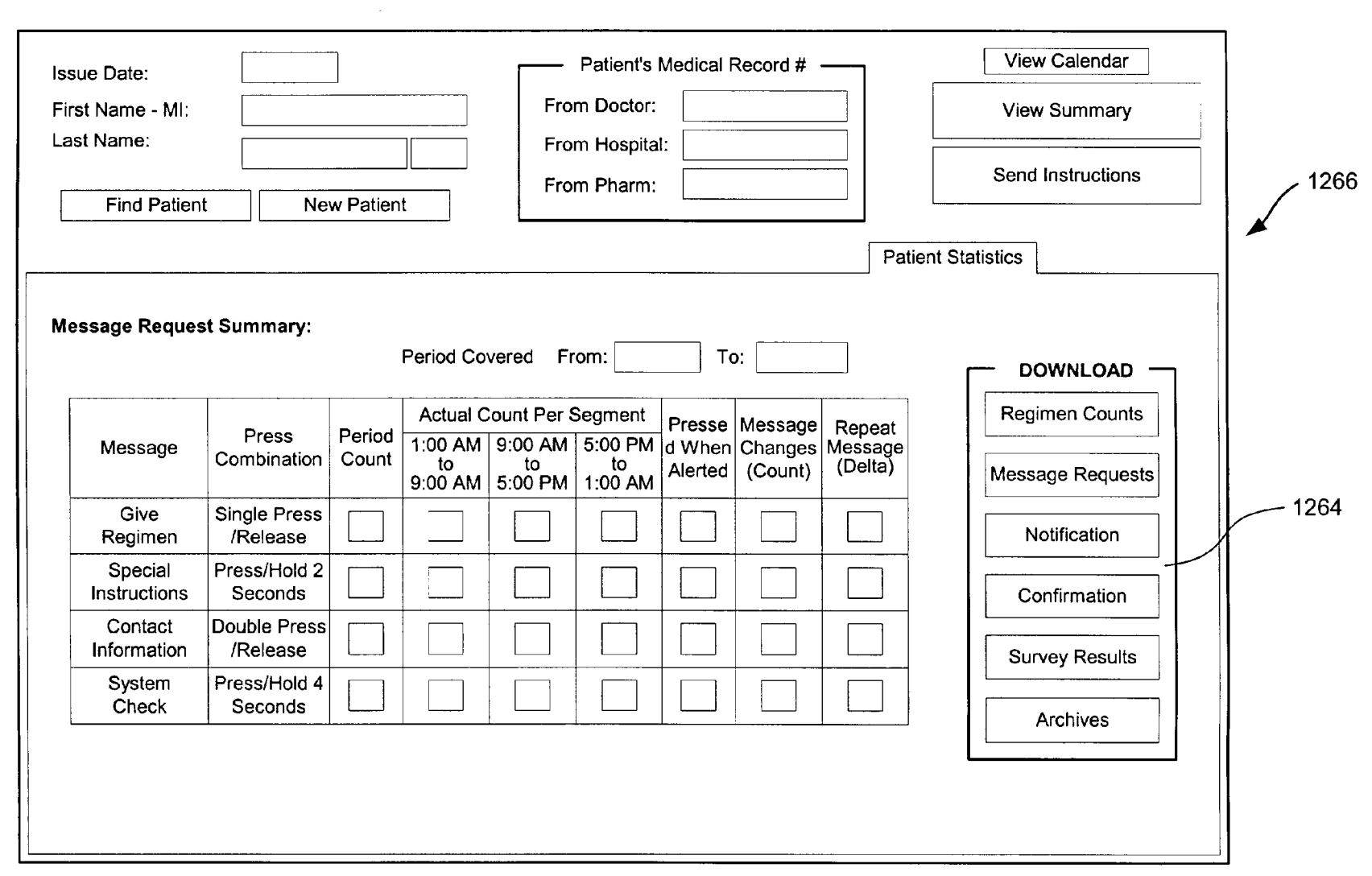

FIG. 12P illustrates a content statistical display 1266 for Message Requests. This display is activated by pressing the corresponding field within the Download section 1264 of the Platform and is associated with the Patient Statistics tab. Although similar to the Regimen Count Summary from FIG. 12O, this table desirably shown how well a patient is able to understands a spoken message based on the number of times the pressing of the Talk Button is repeated. It may also be used to calculate the response time of the patient based on the time differential between a pre-programmed notification signal and the corresponding press to hear the spoken instructions. As before, the contents of such a table my be automatically filled with the statistics that were downloaded from the hardware device to the Platform upon its return from the patient using coded routines, algorithms and standard formulas.

Figure 12Q:
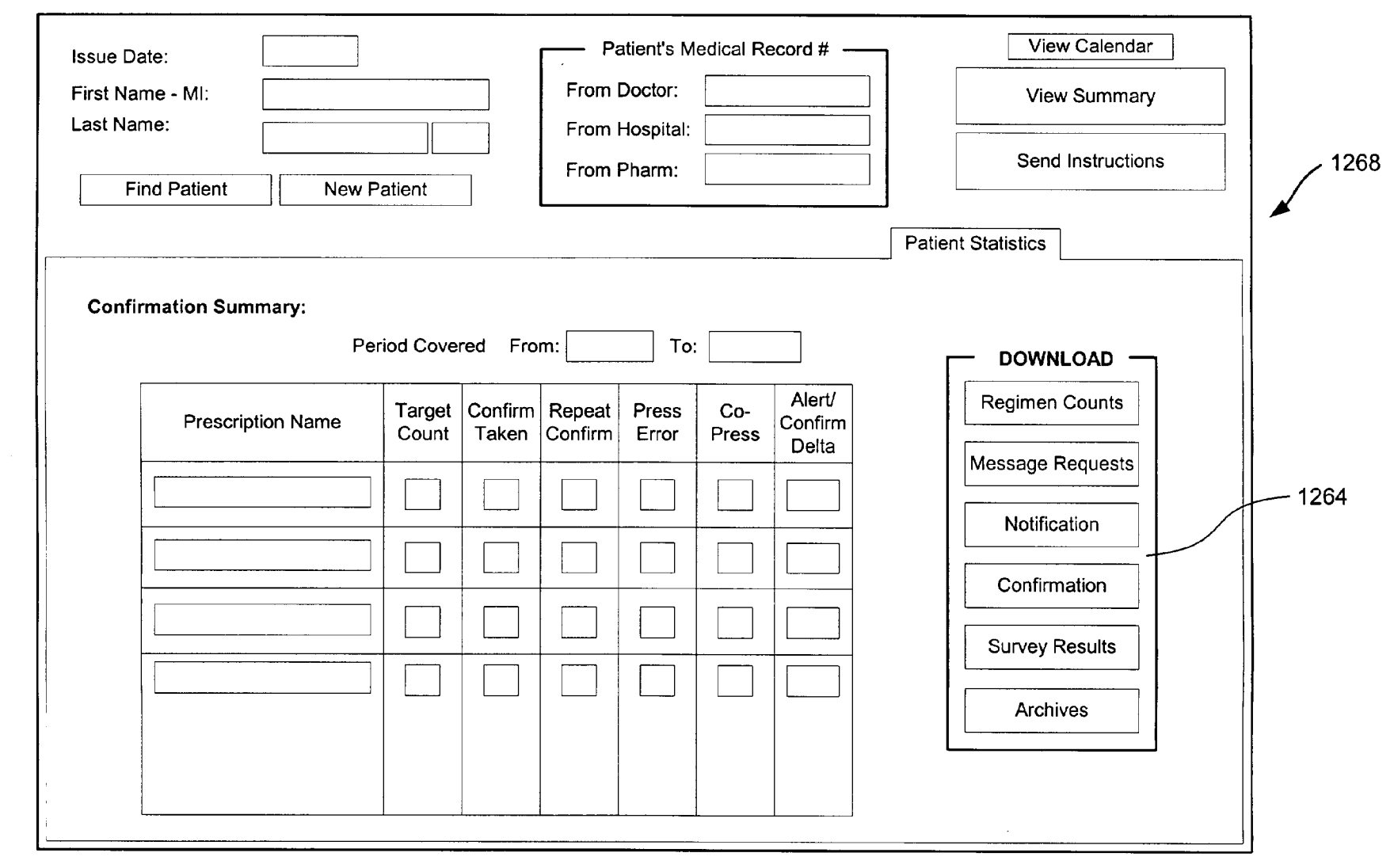

FIG. 12Q illustrates a content statistical display 1268 for Confirmation Summary. This display is activated by pressing the corresponding field within the Download section 1264 of the Platform and is associated with the Patient Statistics tab. The purpose of this table is to determine how often a patient is compliant with a prescribed regimen. The statistical display 1268 for Confirmation Summary calls for the use of a second button located on the hardware device that is activated by the patient to confirm that the medication was taken after being notified by one or more sensory based notification signals or the spoken instructions. The Confirmation Button may be green in color and square in shape in contrast to the Talk Button which may be red in color and round in shape. Although the Confirmation Button is not shown in a figure for this application, it may be used as a "yes" or "no" recording mechanism based on a pre-defined set of press combinations. Such a confirmation button is beneficial for a hardware device that merely informs the patient of a prescribed regimen but does not dispense any actual mediation from within the device. This button, pressed in pre-defined combinations or in conjunction with the Talk Button, may be used to calculate the patient's response time based on the differential between a pre-programmed notification signal and the corresponding press to hear the spoken instructions. It can also be used indicate a patient's understanding of a given alert mechanism. As before, the contents of such a table may be automatically filled with the statistics that were downloaded from the hardware device to the Platform upon its return from the patient using coded routines, algorithms and standard formulas.

Figure 12R:
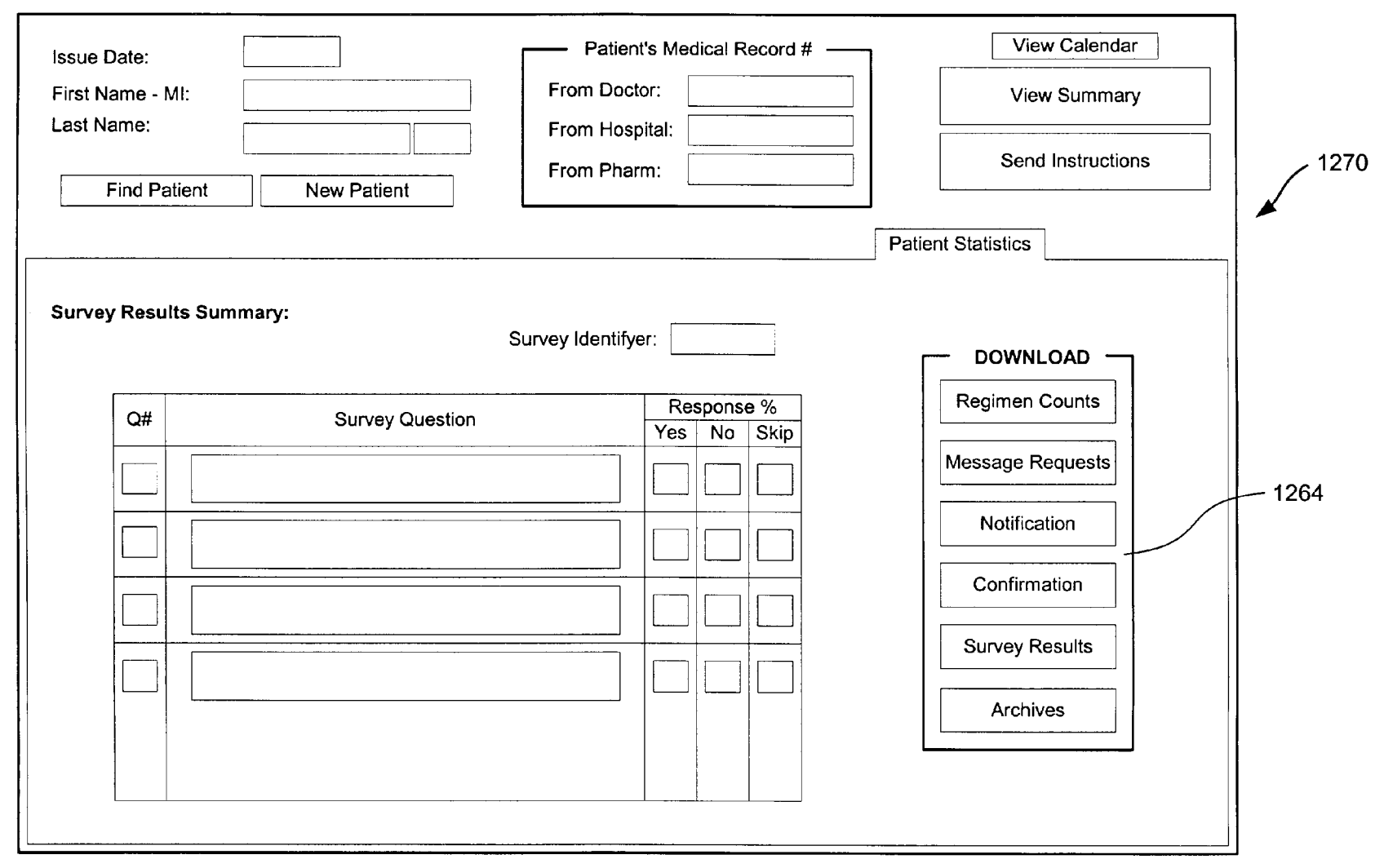

FIG. 12R illustrates a content statistical display 1270 for the Survey Results Summary. This display is activated by pressing the corresponding field within the Download section 1264 of the Platform and is associated with the Patient Statistics tab. The purpose of this table is to display the results of a programmed survey (an example of which is shown in FIG. 12X) whose results are determined by a pre-defined press combination of the Confirmation Button. As before, the contents of such a table may be automatically filled with the statistics that were downloaded from the hardware device to the Platform upon its return from the patient using coded routines, algorithms and standard formulas.

In addition to Pharmacists, Doctors and Administrators may have a need or desire to review a particular set of generated statistics relating to a given patient. These situations are made possible through the use of proper access codes that display the appropriate content tabs. Again, to emphasize Platform flexibility, any pre-established content tabs displayed for a particular recipient can be changed by the system Administrators and tracked for future reference.

Two remaining content tabs may be used to cross-reference the actions taken by different users of the Platform. A Linkage tab 1272, shown in FIG. 12S, and an Archives tab 1276, shown in FIG. 12T, may be used together or separately to create a permanent historical record. The content of the historical record may be determined by checking desired items from a Recorded History section 1274 on the Linkage tab. When activated, all changes made to a patient's record associated with the checked field are permanently entered into a notation section with a corresponding date stamp that can be searched by a specific date, a selected date range or a keyword/phrase search. Such records remain permanent even if the decision to check a given criteria is reversed at a later time. In similar fashion, a Dispenser Tracking section 1273, shown in FIG. 12S, instructs the hardware device as to which items will be tracked.

Figure 12V:
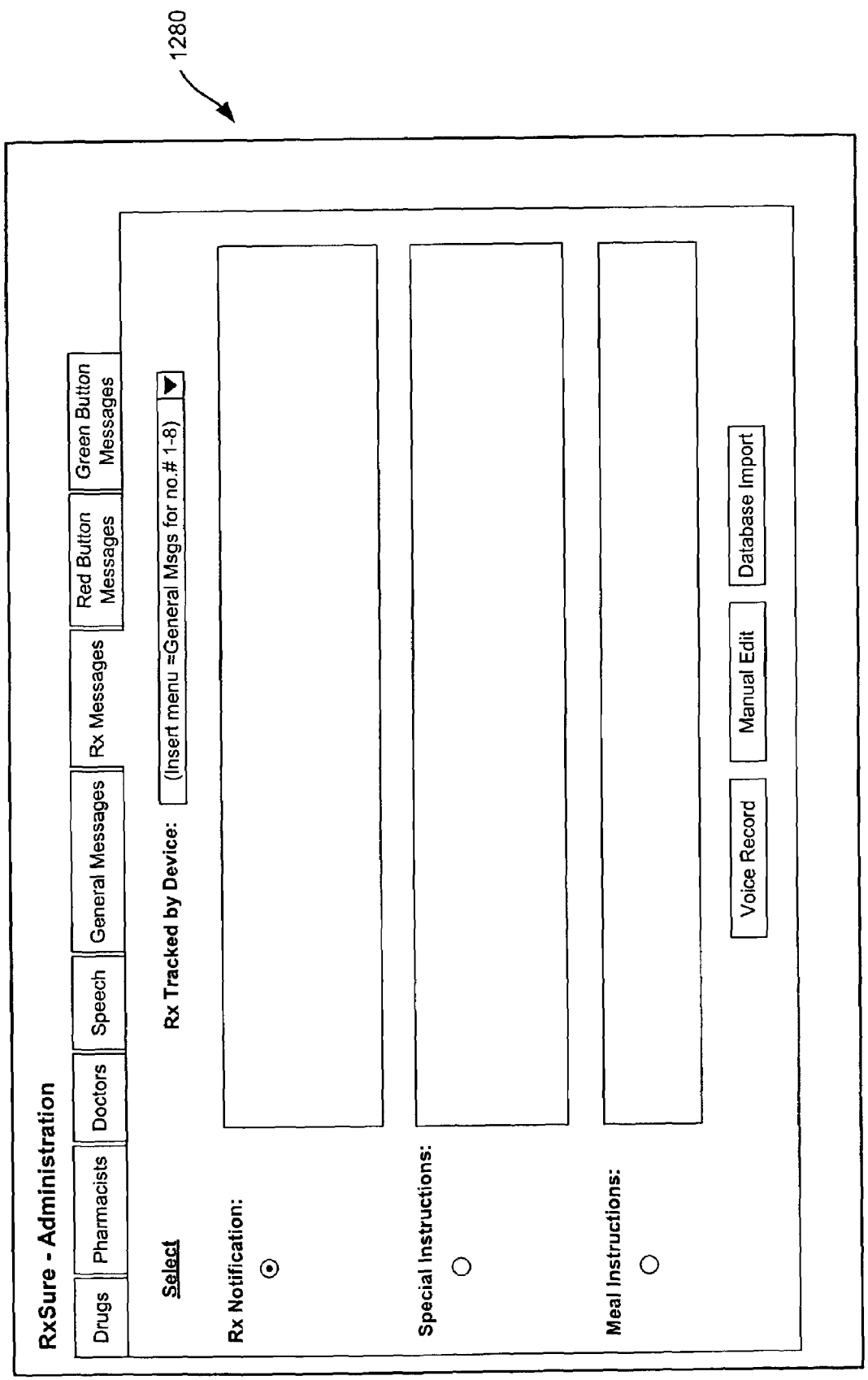

Several administrative functions, with separate callout tabs, help facilitate processes including, but are not limited to, organizing information into tables or displays, coordinating databases, establishing speech parameters, listing or summarizing general and specific messages, and providing means to enter unique messages. In FIG. 12U, an administrative tab 1278 titled "General Messages" illustrates a method of organizing the general messages spoken by the hardware device. Each entry can be edited by typing or voice recording a selected message for pre-programmed insertion into a spoken announcement. In FIG. 12V, an administrative tab 1280 titled "Rx Messages" illustrates the ability to provide an additional text or voice recorded message that corresponds with a selected "General Message" from FIG. 12U. In FIG. 12W, an administrative tab 1284 titled "Red Button Messages" provides the user (typically the system Administrator) with the resulting display of the combined "General Message" and "Specific Message" text that will be outputted by the hardware device. In FIG. 12X, an administrative tab 1288 titled "Green Button Messages" illustrates the ability to design a custom survey spoken by the hardware device. Such a survey may utilize "Yes/No", "True/False", or "Multiple Choice" answers based on the press combination of the green Confirmation Button. Again, the questions, as well as pre-defined answers to the questions, can be entered by typing the text or voice recorded.

Therefore, as discussed previously herein, the present invention provides a system and a process which facilitates the provisioning of specific and individualized instructions to a patient for a treatment regimen. While the present invention has been described in the context of a system and a process it is to be appreciated that the present invention is not limited to the systems and/or processes identified herein and may be modified as individual applications dictate and/or specific embodiments require.

The invention claimed is:

1. An apparatus utilized to provide messages which include instructions related to a treatment regimen for a patient, wherein the treatment regimen is provided to the apparatus via a Platform accessed by at least one of a Doctor and a Pharmacist, comprising:

a microprocessor for controlling the operation of a treatment device and gathering compliance information on the patient's compliance with the treatment regimen;

a storage device, connected to the microprocessor, providing a storage location for a message that includes at least one instruction for administering a treatment regimen to the patient, wherein the message is provided to the apparatus via a Platform accessed by at least one of a Doctor and a Pharmacist;

an internal clock, providing timing signals to the microprocessor;

a speech synthesizer, connected to the microprocessor, for converting a message retrieved from the storage device by the microprocessor from a first format into an audibly perceptible message format for subsequent presentation to the patient, wherein the processor is configured, upon determining based upon a reading from the internal clock that a predetermined time has arisen, to retrieve the message from the storage device and provide the message to the speech synthesizer;

a communications interface, connected to the microprocessor, for providing feedback to at least one of the Doctor and the Pharmacist, the feedback at least partially based on the compliance information; and at least one internal chamber for storing a medication, wherein the medication is at least one element of the treatment regimen and the medication is a prescribed medication or an over-the-counter medication; and a cap configured to restrict access to the internal chamber, wherein the cap is selected from the group consisting of: sliding top opener, sliding side opener, tab opener, pop top, twist top, and a child Proof top, the cap further comprises: a cap sensor which detects when the cap is open, and the microprocessor records in the storage device a record of each opening of the cap and a time indicator when the cap was opened;

wherein the record of each opening of the cap and the time indicator comprise compliance information stored in the storage device, the compliance information being accessible via the Platform for playback and analysis by a Doctor or a Pharmacist.

2. The apparatus of claim 1, wherein the apparatus further comprises:
an amplifier, connected to the speech synthesizer, which amplifies the audibly perceptible message; and
a speaker, connected to the amplifier, which presents the audibly perceptible message to a user.

3. The apparatus of claim 1, wherein the internal chamber is configured to hold a disposable sleeve, wherein the disposable sleeve is configured to store and dispense at least one medication.

4. The apparatus of claim 1, wherein access to the internal chamber is restricted by a locking mechanism.

5. The apparatus of claim 4, wherein the locking mechanism further comprises a solenoid locking mechanism controlled by the microprocessor, wherein access to the internal chamber via the cap is allowed at those times when a treatment regimen calls for the dispensing of a medication from the apparatus, and at all other times, access to the internal chamber is restricted.

6. The apparatus of claim 1, wherein the apparatus further comprises at least one visual indicator of an operating status of the apparatus, selected from the group consisting of: light emitting diode, liquid crystal display, fluorescent, incandescent, and neon.

7. The apparatus of claim 1, wherein the apparatus further comprises a user input interface selected from the group consisting of: Talk button, volume control, alphanumeric keypad, voice command system, and at least one button.

8. The apparatus of claim 7, whereupon inputting a first utilization sequence via the user input interface, the microprocessor retrieves from the storage device a schedule for a medication treatment regimen, compares the schedule to a current reading of the internal clock, and selects a message to be presented to the user based upon whether the current reading is before, during or after a scheduled time for providing a treatment regimen to the patient; whereupon inputting a second utilization sequence via the user input interface, the microprocessor retrieves from the storage device and presents to the user a message providing contact information for at least one of a Doctor and a Pharmacist; and whereupon inputting a third utilization sequence via the user input interface the microprocessor retrieves from the storage device and presents to the user at least one of conflicts, warnings, and treatment regimen information.

9. The apparatus of claim 8, wherein the first utilization sequence, second utilization sequence and third utilization sequence further comprise depressing a Talk button for a pre-determined period of time or a pre-determined number of repetitions.

10. The apparatus of claim 1, wherein the apparatus further comprises:
a holding chamber, connected to the at least one internal chamber, for storing a dosage of a medication to be dispensed to a patient, wherein the holding chamber is accessible to the user; and
a medication transferring device, which transfers medication from the at least one internal chamber to the holding chamber;
whereupon receiving a command from the microprocessor, the medication transferring device transfers a pre-determined dosage of at least one medication from the at least one internal chamber to the holding chamber.

11. The apparatus of claim 10, wherein at least one internal chamber is configured to accept a removable medication dispensing cartridge further comprising:
a spring loaded platform that applies an upward pressure upon a medication contained within the cartridge;
a top, situated above and at the farthest extension of the spring loaded platform;
a first opening, situated near the top, providing access to the medication by the medication transferring device; and
a second opening, situated opposite from and parallel to the first opening, through which a dosage of a medication may be dispensed by the medication transferring device into the holding chamber;
whereupon receiving a command from the microprocessor to extract a medication from the cartridge within the internal chamber, the medication transferring device utilizes the first opening to direct the transfer of a dosage of medication stored in the cartridge through the second opening and into the holding chamber.

12. The apparatus of claim 11, wherein the medication transferring device further comprises a probe driven by a motor and a gear; wherein the operation of the motor is controlled by the microprocessor; and whereupon activation of the motor by the microprocessor, the probe enters through the first opening, makes contact with a dosage of medication, and pushes the dosage of medication through the second opening and into the holding chamber; whereupon the probe returns through the first opening, and the spring loaded platform positions a next dosage opposite the probe for future insertion into the holding chamber.

13. The apparatus of claim 12, wherein the medication transferring device provides a tactile indication signal that a medication is available for dispensing to the patient.

14. The apparatus of claim 11, wherein the cartridge further comprises a first electrical connector, which includes an associated storage device containing information identifying the medication contained within the cartridge; and wherein the apparatus further comprises a second electrical connector, connected to the microprocessor and situated opposite the first electrical connector; wherein information identifying the medication contained within the cartridge is communicated to the microprocessor via the first and second electrical connectors.

15. The apparatus of claim 1, wherein the apparatus further comprises a Platform interface which facilitates bi-directional communications between the apparatus and the Platform, and wherein the Platform interface receives from the Platform, information related to the treatment regimen and provides the information to the storage device for storage.

16. The apparatus of claim 15, wherein the Platform interface further comprises a data port selected from the group consisting of: a serial, a parallel, universal serial bus, infrared, RF, IrDA, Blue Tooth, wireless, Ethernet, RS-232, and a telephone data port.

17. The apparatus of claim 15, wherein the Platform interface further comprises a smart card reader, wherein the smart card reader, under the control of the microprocessor, retrieves from a smart card information related to the treatment regimen, and provides the information to the storage device for storage, wherein the information related to the treatment regimen is stored on the smart card by a Platform accessed by a Doctor or a Pharmacist.

18. The apparatus of claim 1, wherein the first format of the message is a text based format.

19. The apparatus of claim 1, wherein the apparatus further comprises a means for storing a verbal message.

20. The apparatus of claim 19, whereupon the occurrence of the predetermined time, the microprocessor directs the playback of the stored verbal message.

21. A device for providing patient specific prescription medication related treatment information comprising:
   at least one internal chamber for storing a prescription medication;
   a microprocessor for controlling the operation of the device and gathering compliance information on the patient's compliance with the treatment regimen;
   a memory storage device, connected to the microprocessor, for storing at least one message containing patient specific prescription medication related treatment information, wherein the message is associated with a scheduled treatment;
   an internal clock for providing timing signals to the microprocessor;
   a speech synthesizer, connected to the microprocessor, for receiving and converting the message into an audibly perceptible message, wherein the microprocessor is configured to, upon the occurrence of a scheduled treatment time, as determined by a comparison of the treatment schedule and the timing signals provided by the internal clock, recall the message from the memory storage device and provide the message to the speech synthesizer;
   a speaker for presenting the audibly perceptible message to a patient;
   a cap providing access to the prescription medication stored in the at least one internal chamber;
   a Platform interface, connected to the microprocessor, providing an interface between the device and a Platform configured to enable at least one of a Doctor and a Pharmacist to provide the patient specific prescription medication related treatment information to the device and to monitor compliance by the patient with a treatment schedule;
   a communications interface, connected to the microprocessor, for providing feedback to at least one of the Doctor and the Pharmacist, the feedback at least partially based on the compliance information; and
   a cap sensor, connected to the microprocessor, and situated to monitor the position of the cap, whereupon opening of the cap by a user, a cap sensor signal is transmitted to the microprocessor, whereupon the receipt of the cap sensor signal the microprocessor records in the memory storage device the occurrence of the opening of the cap and a time of the opening as compliance information, the compliance information being utilized by at least one of the Doctor and Pharmacist, via the Platform connected to the device via the Platform interface, to verify the patient's compliance with the treatment schedule.

22. The device of claim 21, wherein the memory storage device stores at least one verbal message.

23. The device of claim 22, wherein a stored verbal message is played back to the patient via the speaker.

24. The apparatus of claim 21, wherein the apparatus further comprises:
   a holding chamber, connected to the at least one internal chamber, for storing a dosage of a medication to be dispensed to a patient; and
   a medication transferring device, which transfers medication from the at least one internal chamber to the holding chamber;
   whereupon receiving a command from the microprocessor, the medication transferring device transfers a pre-determined dosage of at least one medication from the at least one internal chamber to the holding chamber.

25. The device of claim 24, wherein the at least one internal chamber is configured to hold a removable medication dispensing cartridge further comprising:
   a spring loaded platform that applies an upward pressure upon a medication contained within the cartridge;
   a top, situated above and at the farthest extension of the spring loaded platform;
   a first opening, situated near the top, providing access to the medication by the medication transferring device; and
   a second opening, situated opposite from and parallel to the first opening, through which a dosage of a medication may be dispensed by the medication transferring device into the holding chamber;
   whereupon receiving a command from the microprocessor to extract a medication from the internal chamber, the medication transferring device utilizes the first opening to direct the transfer of a dosage of medication through the second opening and into the holding chamber.

26. A method for providing instructions to a patient for a treatment regimen provided by a patient accessible device, comprising:
   receiving an indication from a patient regarding a treatment regimen; wherein the indication is provided by depressing a button on the patient accessible device;
   gathering compliance information on the patient's compliance with the treatment regimen;
   retrieving a message, responsive to the indication and containing at least one instruction related to a treatment regimen for a patient, from a memory storage device provided in a patient accessible device;
   converting the message into an audible format;
   presenting the audibly formatted message to the patient via the patient accessible device;
providing feedback to at least one of a Doctor and a Pharmacist, the feedback at least partially based on the compliance information;
   wherein the message was previously provided, at least one of the Doctor and the Pharmacist, to the memory storage device via a Platform connected to the memory storage device
   determining whether a pre-determined time for dispensing a medication to the patient via the patient accessible device has arisen;
   presenting the audibly formatted message to the patient when the pre-determined time has arisen; and
   activating a visual indicator;
   wherein the audibly formatted message presented and the visual indicator activated varies depending upon whether a current time is the same as the pre-determined time for dispensing a medication, a first warning time, or a second warning time;
   monitoring the utilization of the patient accessible device, wherein the utilization of the patient accessible device is monitored by providing a cap and a cap sensor, wherein the cap sensor determines when the cap has been accessed by a user in order to gain access to at least one medication provided by the patient accessible device; and recording each utilization of the patient accessible device by a user;

wherein each recording of each utilization of the patient accessible device provides compliance information utilized by the Doctor and Pharmacist to determine a compliance history for the patient with the treatment regimen.

27. The method of claim 26, wherein the method further comprises unlocking a cap securing access to at least one internal chamber provided in the patient accessible device in which a prescription medication is stored.

28. The method of claim 27, wherein the method further comprises monitoring the cap and recording when the cap is opened and access to the internal chamber is obtained.

29. The method of claim 26, wherein the method further comprises dispensing a medication from an internal chamber into a holding chamber at a scheduled time for providing the medication to the patient, wherein the holding chamber is accessible to the user.

30. The method of claim 29, wherein the scheduled time is provided in a treatment regimen schedule communicated to the device by the Platform via the Platform interface, wherein the treatment regimen schedule is specified to the Platform by at least one of the Doctor and the Pharmacist.

31. The method of claim 26, wherein the method further comprises verifying, via a treatment clearance system connected to the Platform, the treatment regimen is safe for the patient prior to providing the message to the patient accessible device.

32. The method of claim 26, wherein the method further comprises activating a medication transferring device, wherein the medication transferring device dispenses a medication from a first chamber into a holding chamber, the holding chamber being accessible to the patient for removing the dispensed medication from the patient accessible device.

33. The method of claim 26, wherein the determinations of the cap sensor are utilized by the Platform to generate a report indicating the patient's compliance with the treatment regimen.

* * * * *